United States Patent
Burright

(10) Patent No.: US 8,183,219 B2
(45) Date of Patent: May 22, 2012

(54) THERAPEUTING COMPOSITIONS COMPRISING AN RNAI AGENT AND A NEUROTROPHIC FACTOR AND METHODS OF USE THEREOF

(75) Inventor: Eric N. Burright, Eagan, MN (US)

(73) Assignee: Medtronic, Inc., Minneapolis, MN (US)

( * ) Notice: Subject to any disclaimer, the term of this patent is extended or adjusted under 35 U.S.C. 154(b) by 174 days.

(21) Appl. No.: 12/522,153

(22) PCT Filed: Jan. 3, 2008

(86) PCT No.: PCT/US2008/050089
§ 371 (c)(1), (2), (4) Date: Jul. 8, 2009

(87) PCT Pub. No.: WO2008/086079
PCT Pub. Date: Jul. 17, 2008

(65) Prior Publication Data
US 2010/0132060 A1    May 27, 2010

Related U.S. Application Data

(60) Provisional application No. 60/878,371, filed on Jan. 3, 2007.

(51) Int. Cl.
*C12N 15/11* (2006.01)
*A61K 31/70* (2006.01)
*A61K 48/00* (2006.01)
*C07H 21/02* (2006.01)
*C07H 21/04* (2006.01)

(52) U.S. Cl. .................... 514/44; 536/24.1; 536/24.5
(58) Field of Classification Search ............... 536/23.1, 536/24.3, 24.33, 24.5
See application file for complete search history.

(56) References Cited

U.S. PATENT DOCUMENTS
2004/0220132 A1   11/2004   Kaemmerer
2006/0210538 A1   9/2006    Kaplitt et al.
2010/0113351 A1*  5/2010    Burright et al. ............... 514/12

OTHER PUBLICATIONS

Zuccato et al. (Science, 2001 vol. 293:493-498).*
Geraerts et al., "Concise Review; Therapeutic Strategies for Parkinson Disease Based on the Modulation of Adult Neurogenesis"; Stem Cells, Nov. 2, 2006: vol. 25, No. 2; pp. 263-270.

* cited by examiner

*Primary Examiner* — Terra Cotta Gibbs
(74) *Attorney, Agent, or Firm* — Fox Rothschild LLP

(57) ABSTRACT

The invention provides novel combination therapies for treating neurodegenerative disease which comprise a) neurotrophic factors or suitable fragments thereof and b) agents capable of causing inhibition of a gene responsible for the neurodegenerative disease. The invention provides novel nucleic acid sequences, methods, and systems suitable for applications of these combination therapies.

25 Claims, 2 Drawing Sheets

THERAPEUTING COMPOSITIONS COMPRISING AN RNAI AGENT AND A NEUROTROPHIC FACTOR AND METHODS OF USE THEREOF

CROSS REFERENCE TO RELATED APPLICATION

The present application is a 35 U.S.C. §371 National Phase application of International Application Serial No. PCT/US2008/50089 filed Jan. 3, 2008, which claims priority under 35 U.S.C. §119 to a U.S. Provisional application 60/878,371 filed on Jan. 3, 2007. The disclosures of which are incorporated herein by reference in their entirety.

FIELD OF THE INVENTION

The instant invention is most closely related to using RNA inhibition for treatment of neurodegenerative diseases.

BACKGROUND

Neurodegenerative disorders (NDs) are a group of related human maladies that share a common pathophysiological feature, the progressive degeneration of selective neuronal populations over the course of time. Despite significant progress in elucidating the genetic causes underlying these disparate disorders, relatively little is known about the biochemical mechanisms that cause the selective neuronal degeneration common to all of them.

One of these diseases, Huntington's Disease (HD), leads to loss of striatal neurons, resulting in both physical and mental disabilities. Symptoms usually appear between the ages of 30 and 50 but can begin as early as 2 and as old as 80. People with Huntington's Disease require care from health professionals of many stripes, including general practitioners, neurologists, social workers, home health aides, psychologists, physical therapists, and speech/language pathologists.

Huntington's Disease Society of America estimates that approximately a quarter of a million Americans have Huntington's Disease or are at risk of inheriting the HD mutation. The cost of caring for patients with neurodegenerative diseases is enormous. For example, combined with the expense of long-term care and the impact of lost productivity, the cost of Huntington's Disease and related disorders is estimated at 2.5 billion dollars.

With the number of individuals affected with neurodegenerative disorders and the costs associated with caring for these individuals, there is a dire need for novel therapies that prevent and treat these conditions.

SUMMARY OF INVENTION

This invention addresses this need by providing, in a first aspect, a first nucleic acid sequence comprising: a second nucleic acid sequence encoding a neurotrophic factor or a functional fragment thereof; and a third nucleic acid sequence encoding an RNAi agent capable of inhibiting expression of a gene that, when in mutant form, is responsible for a neurodegenerative disease. In this aspect, the first nucleic acid sequence is preferably included within a vector, which in one embodiment may be a viral vector, such as an AAV vector.

In yet another set of embodiments, the first sequence may comprise the first or the second promoters, which regulate the expression of the second nucleic acid sequence and the third nucleic acid sequence, respectively.

In different non-limiting embodiments of the invention, the neurodegenerative disease is HD, Parkinson's Disease (PD), Alzheimer's Disease (AD) or amyotrophic lateral sclerosis (ALS) where the HD gene, the alpha-synuclein gene, the BACE1 gene, or the SOD1 gene and the neurotrophic factors BDNF or GDNF, GDNF, NGF, and IGF-1 or VEGF, are targeted for HD, PD, AD, or ALS therapies, respectively.

In a second aspect, the invention provides a method of treating a neurodegenerative disease in a patient comprising administering to said patient: an RNAi agent capable of inhibiting expression of a gene involved in the neurodegenerative disease process; and at least one of a neurotrophic factor or a functional fragment thereof.

In a third aspect, the invention provides a method of treating a neurodegenerative disease in a patient comprising: administering to said patient a first nucleic acid sequence of any embodiment of the first aspect of the invention.

In another embodiment, the methods according to the second and the third aspects of the invention may further optionally comprise mapping an area containing a neuron affected with the neurodegenerative disease, which may comprise Alzheimer's disease, Parkinson's disease, amyotrophic lateral sclerosis, or Huntington's disease.

In a fourth aspect, the invention provides a system for treating a live patient with a neurodegenerative disease comprising: a) a means for mapping a location of a neuron affected with the neurodegenerative disease within the brain of said live patient; b) an intracranial access device providing physical access to an area adjacent to the neuron; and c) at least one of the first nucleic acid sequences of any embodiment of the first aspect of the invention or the RNAi agent of any embodiment of the second aspect of the invention and the neurotrophic factor any embodiment of the second aspect of the invention.

In different embodiments of the invention, the system further comprises a means for mapping the neuron. In different embodiments of the invention, the neurodegenerative disease may comprise Alzheimer's disease, Parkinson's disease, amyotrophic lateral sclerosis, or Huntington's disease.

DETAILED DESCRIPTION OF PREFERRED EMBODIMENTS

Figure 1:
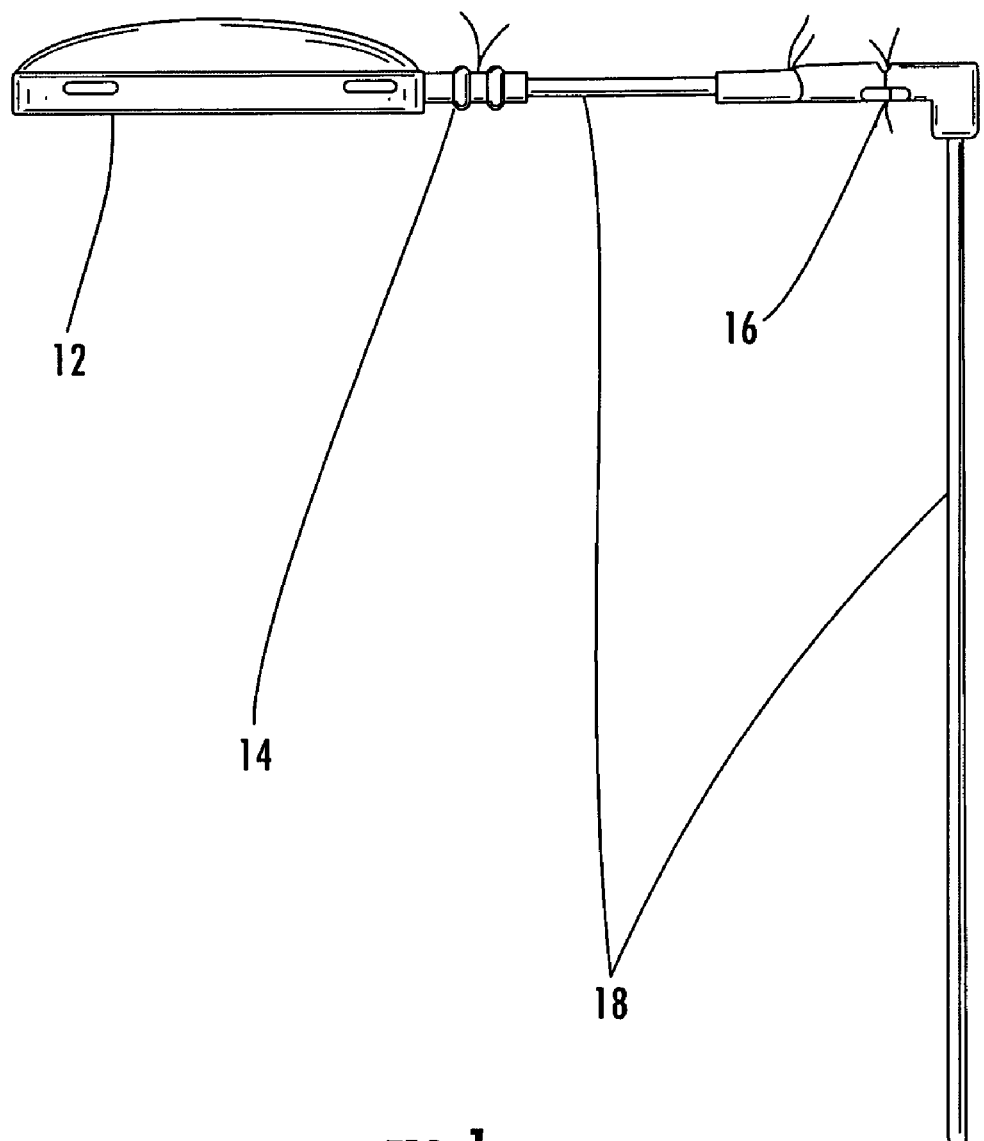
FIG. 1 and FIG. 2 both provide a schematic illustration of the Model 8506 investigational device suitable for different embodiments of the system of the instant invention.

In general, this invention is drawn to novel compositions, methods and systems for treating neurodegenerative disorders which combine RNAi therapy and neurotrophic factor supplementation.

The methods of the present invention utilize routine techniques in the field of molecular biology. Basic texts disclosing general molecular biology methods include Sambrook et al., *Molecular Cloning, A Laboratory Manual* (3d ed. 2001) and Ausubel et al., *Current Protocols in Molecular Biology* (1994).

Definitions

In order to better describe the instant invention, the following non-limiting definitions are provided:

The term "RNA interference agent" or "RNAi agent" refers to ribonucleic acid sequences, modified ribonucleic acid sequences, or DNA sequences encoding said ribonucleic acid sequences, which cause RNA interference and thus decrease expression of the target gene. In different embodiments, the RNAi agent includes, without limitations, shRNAs, siRNAs, miRNAs, and DNA-RNA hybrids. In certain embodiments, the RNAi agent may be modified as described in detail below.

The term "small interfering RNA" or "siRNA" refers to a double-stranded RNA molecule wherein each strand is between about 15 and about 30 bases of ribonucleic acid in length, and the two strands have a region of complementarity such that the two strands hybridize or "base pair" together through the annealing of complementary bases (Adenine to Uracil, and Guanine to Cytosine). For some siRNA molecules, the two strands hybridize together in a manner such that there is an overhang of non-annealed bases at the 5' or 3' ends of the strand. For other siRNA molecules, the two strands hybridize together such that each base of one strand is paired with a base of the other strand. For some siRNA molecules, the two strands may not be 100% complementary but may have some bases that do not hybridize due to a mismatch. For some siRNA molecules, the RNA bases may be chemically modified or additional chemical moieties may be conjugated to one or more ends of one or more of the strands.

The term "shRNA" refers to a "short, hairpin" RNA molecule comprised of a single strand of RNA bases that self-hybridizes in a hairpin structure. The RNA molecule is comprised of a stem region of RNA bases that hybridize together to form a double-stranded region, and a loop region of RNA bases that form the bend of the hairpin. The term "shRNA" also refers to a DNA molecule from which a short, hairpin RNA molecule may be transcribed in vitro or in vivo.

The term "functional fragment" of a protein refers to a fragment of that protein which at least partially retains the protein's function of interest. Thus, in different embodiments, the functional fragments of GDNF, BDNF, NGF, IGF-1, and VEGF at least partially retain neuroprotective properties of the respective proteins.

The term "involved in" as applied to genes involved in neurodegenerative diseases refers to genes which are responsible for the neurodegenerative diseases (e.g., IT15 and HD) or involved in a process or cellular pathway that contributes to a neurodegenerative disease process (e.g., BACE1 and AD).

The term "treating" or "treatment" refers to executing a protocol, which may include administering one or more drugs to a patient (human or otherwise), in an effort to alleviate signs or symptoms of a neurodegenerative disease. Alleviation can occur prior to signs or symptoms of the disease appearing, as well as after their appearance. Thus, "treating" or "treatment" includes "preventing" or "prevention" of disease. In addition, "treating" or "treatment" does not require complete alleviation of signs or symptoms, does not require a cure, and specifically includes protocols which have only a marginal effect on the patient.

The terms "patient" and "subject" refer to a biological system to which a treatment can be administered. A biological system can include, for example, an organ, a tissue, or a multi-cellular organism. The terms "patient" and "subject" are used interchangeably throughout this disclosure and include, without limitations, humans.

The term "practitioner" refers to a person or persons who practice the methods and systems of the instant invention on the patient. The term includes, without limitations, doctors, nurses, and scientists.

The term "promoter element" or "promoter" or "regulatory region" refers to a DNA sequence capable of being bound by an RNA polymerase in a cell (e.g., directly or through other promoter-bound proteins or substances) and allowing for the initiation transcription of a coding or non-coding RNA sequence. A promoter sequence is, in general, bounded at its 3' terminus by the transcription initiation site and extends upstream (5' direction) to include the minimum number of bases or elements necessary to initiate transcription at any level. Within the promoter sequence may be found a transcription initiation site (conveniently defined, for example, by mapping with nuclease S1), as well as protein binding domains (consensus sequences) responsible for the binding of RNA polymerase. The term "promoter" may further optionally include other expression control sequences, including enhancer and repressor sequences.

The term "in operable combination," "in operable order," or "operably linked" refers to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The terms "penetration enhancer," "cell penetration enhancer," and "cellular uptake enhancer" include single compounds as well as compositions comprising a plurality of compounds, wherein the combination of those compounds improves targeted delivery and/or cellular uptake of a cargo, such as a neurotrophic factor or an RNAi agent.

Expansions of CAG trinucleotide repeats (CAG repeats) in coding regions of human genes cause numerous disorders by generating proteins with elongated polyglutamine (polyQ) stretches. This group of disorders includes by way of example Dystrophia myotonica, Spinocerebellar ataxia type 1, Spinocerebellar ataxia type 2, Spinocerebellar ataxia type 3, Spinocerebellar ataxia type 6, Spinocerebellar ataxia type 7, Spinocerebellar ataxia type 8, Spinocerebellar ataxia type 17, Huntington disease-like 2, Spinal and bulbar muscular atrophy, Huntington disease, Dentatorubral-pallidoluysian atrophy, Oculopharyngeal dystrophy, Congenital central hypoventilation syndrome, Infantile spasms, Synpolydactyl), Cleidocranial dysplasia, Holoprosencephaly, Hand-foot-genital syndrome, Type II blephorophimosis, ptosis, and epicanthus inversus syndrome. (Wanker E. E. (2000) *Biol. Chem.*, 381:937-942; Gusella J. F. and MacDonald, M. E. (2000) *Nature Rev. Neurosci.*, 1:109-115; and Usdin K. and Grabczyk, E. (2000) *Cell. Mol. Life. Sci.*, 57:914-931).

A further problem of these neurodegenerative diseases is that their prevalence continues to increase, thus creating a serious public health problem.

Recent studies have pointed to alpha-synuclein (Parkinson's disease), beta-amyloid-cleaving enzyme 1 (BACE1 (including variants thereof, e.g. variants A, B, C, and D)) (Alzheimer's disease), huntingtin (Huntington's disease), and ataxin1 (Spinocerebellar Ataxia Type 1) as major factors in the pathogenesis of each of these diseases, respectively.

Additional non-limiting examples of the neurodegenerative diseases are shown in Table 1.

TABLE 1

| Triplet Repeat Expansion Disorders | | | | |
|---|---|---|---|---|
| Disease | Symptoms | Gene | Locus | Protein |
| Non-coding repeats | | | | |
| Dystrophia myotonica 1 | Weakness, Myotonia | DMPK | 19q13 | Dystrophia myotonica Protein kinase |

TABLE 1-continued

Triplet Repeat Expansion Disorders

| Disease | Symptoms | Gene | Locus | Protein |
|---|---|---|---|---|
| Spinocerebellar ataxia 8 | Ataxia | Antisense to KLHL1 | 13q21 | Undetermined |
| Huntington disease-like2 | Chorea, dementia | JPH3 | 16q24.3 | Junctophilin 3 |
| Polyglutamine disorders | | | | |
| Spinal and bulbar muscular atrophy | Weakness | AR | Xq13-q21 | Androgen receptor |
| Huntington disease | Chorea, dementia | IT15 | 4P16.3 | Huntingtin |
| Dentatorubral-pallidoluysian atrophy | Ataxia, myoclonic epilepsy, dementia | DRPLA | 12p13.31 | Atrophin 1 |
| Spinocerebellar ataxia 1 | Ataxia | SCA1 | 6p23 | Ataxin 1 |
| Spinocerebellar ataxia 2 | Ataxia | SCA2 | 12q24.1 | Ataxin 2 |
| Spinocerebellar ataxia 3 | Ataxia | SCA3/MJD | 14q32.1 | Ataxin 3 |
| Spinocerebellar ataxia 6 | Ataxia | CACNA1A | 19p13 | $a_{1A}$-voltage-dependent calcium channel subunit |
| Spinocerebellar ataxia 7 | Ataxia | SCA7 | 3p12-p13 | Ataxin 7 |
| Spinocerebellar ataxia 17 | Ataxia | TBP | 6q27 | TATA box binding protein |
| Polyalanine disorders* | | | | |
| Oculopharyngeal dystrophy | Weakness | PABPN1 | 14q11.2-q13 | Poly(A)-binding protein 2 |
| Congenital central hypoventilation syndrome | Respiratory difficulties | PHOX2B | 4p12 | Paired-like homeobox 2B |
| Infantile spasms | Mental retardation, epilepsy | ARX | Xp22.13 | Aristaless-related homeobox, X-linked |
| Synpolydactyly | Limb malformation | HOXD13 | 2q31-q32 | Homeobox D13 |

*Polyalanine expansions have also been reported among mutations in other genes, including RUNX2 (runt-related transcription factor 2) in cleidocranial dysplasia, ZIC2 (Zic family member 2) in holoprosencephaly HOXA13 (homeobox A13) in hand-foot-genital syndrome, and FOXL2 (forkhead box L2) in type II blepharophimosis, ptosis, and epicanthus inversus syndrome. Small aspartic acid repeat expansions have been reported among other mutations in the COMP (cartilage oligomeric mat4rix protein) gene in patients with multiple epiphyseal dysplasia.

For purposes of illustration only, Huntington's disease (HD) will be discussed herein. The gene responsible for HD contains an expanded and unstable CAG trinucleotide repeat (Huntington's Disease Collaborative Research Group, 1993 Cell 72:971-983). The HD gene (also referred to as "huntingtin gene" or "IT15 gene"), which encodes huntingtin, a 350-kDa protein whose functions have not been fully elucidated, is located on the human chromosome 4 and consists of 67 exons. The disease-causing mutation is a CAG repeat expansion located within exon 1 of the HD gene (HD exon1). The CAG repeat is translated into a polyQ stretch. The disease manifests itself when the polyQ stretch exceeds the critical length of 37 glutamines (pathological threshold), whereas 8-35 glutamine residues in huntingtin are tolerated by neuronal cells. Experimental evidence has been presented that huntingtin fragments with polyQ tracts in the pathological range (more than 37 glutamines) but not in the normal range (20-32 glutamines) form high molecular weight protein aggregates with a fibrillar morphology in vitro and in cell culture model systems (Scherzinger et al. (1999) Proc. Natl. Acad. Sci. USA, 96:4604-4609; and Waelter et al., (2001) Mol. Biol. Cell, 12:1393-1407). In addition, inclusions with aggregated N-terminally truncated huntingtin protein were detected in HD transgenic mice carrying a CAG repeat expansion of 115-156 units and in HD patient brains (Davies et al., (1997) Cell, 90:537-548; and DiFiglia et al., (1997) Science, 277:1990-1993), suggesting that the process of aggregate formation may be important for the progression of HD. However, the mechanisms by which the elongated polyQ sequences in huntingtin cause dysfunction and neurodegeneration are not yet understood (Scherzinger et al., (1999); Tobin A. J. and Signer, E. R. (2000) Trends Cell Biol., 10:531-536; and Perutz M. F. (1999) Glutamine repeats and neurodegenerative diseases: molecular aspects. Trends Biochem. Sci., 24:58-63).

It is known that patients are able to survive and live healthy lives with only one functioning copy of the IT15 gene. Moreover, patients with expanded CAG repeats are born with no apparent defects while huntingtin-null mice exhibit embryonic lethality. These and other data suggest that huntingtin is neuroprotective in brain cells exposed to various apoptotic stimuli. Cattaneo et al., Nature Reviews 6: 919-930 (2005).

Additional data link huntingtin to brain-derived neurotrophic factor (BDNF), which is especially important for the survival of striatal neurons. Id. It has been shown that wildtype huntingtin but not huntingtin with expanded number of glutamine repeats increases transcription of BDNF gene.

In addition to regulating transcription of the BDNF gene, it was found that wildtype huntingtin increases but mutant huntingtin represses axonal transport of BDNF. Id. Thus, one mechanism of Huntington's disease progression is due to decreased transcription and trafficking of BDNF.

Previous studies report that gene delivery of BDNF or GDNF (glial cell derived neurotrophic factor) is neuroprotective in a model of quinolinic acid model of Huntington's disease. Kells et al., *Mol. Ther.* 9(5): 682-688 (2004). However, the treatment with neurotrophic factor (e.g., BDNF) gene delivery may not be efficient since the mutant huntingtin would inhibit expression and appropriate trafficking of BDNF. In addition, mutant huntingtin has been shown to down-regulate expression of the receptor for BDNF, TrkB (Gines et al., 2006 European J Neurosci 23:649-658).

Thus, the inventors propose a therapy for Huntington's disease which comprises a treatment with a combination of RNAi agent and neurotrophic factor and systems, methods, and compositions associated therewith.

The compositions, methods, and systems of the invention according to any embodiment of any of the aspects of the invention may be used whether the RNAi agent is allele-specific or not allele-specific (i.e., whether it selectively reduces expression of a specific allele of the gene causing the neurodegenerative disease). However, since patients with only one functioning copy of the IT15 gene can live healthy lives, it appears that one functioning copy of the IT15 gene is sufficient to maintain a level and appropriate trafficking of BDNF which is effective for neuroprotection. Accordingly, in one embodiment, the RNAi agent is not allele-specific. However, the invention does not exclude the use of the methods, compositions, and systems for treatment of the neurodegenerative diseases, wherein the RNAi agent is allele-specific.

In one aspect, the invention provides a first nucleic acid sequence comprising: a second nucleic acid sequence encoding a neurotrophic factor or a functional fragment thereof; and a third nucleic acid sequence encoding an RNAi agent capable of inhibiting expression of a gene involved in a neurodegenerative disease.

The second nucleic acid sequence comprises in one embodiment a cDNA encoding a neurotrophic factor or a functional fragment thereof. Among suitable neurotrophic factors are, without limitations, BDNF, GDNF, NGF, VEGF, and IGF-1.

As mentioned above, the first nucleic acid sequence further includes a third nucleic acid sequence which comprises an RNAi agent capable of inhibiting expression of a gene responsible for a neurodegenerative disease. In preferred embodiments, the RNAi agents comprise sequences which are a sufficient length and/or stably interact with their complementary substrate sequences. In this and other embodiments of the invention, a wide variety of genes may be selected for preparing the RNAi agent for the third nucleic acid sequence. The suitable examples include, without limitation, IT15, DRPLA, SCA1, SCA2, SCA3/MJD, CACNA1A, SCA7, TBP, PABPN1, PHOX2B, ARX, HOXD13, BACE1, SOD-1, and APP.

In one embodiment, the gene involved in the neurodegenerative disease is the IT15 gene and the RNAi agent comprises a sequence selected from the sequences shown in Table 2.

TABLE 2

Non-limiting examples of sequences suitable for RNAi agents which can be used for IT15, BACE1, a-synuclein, or SOD1 inhibition.

| SEQ ID NO: | Target Gene | siRNA Sequence | Accession # | Position within Accession # |
|---|---|---|---|---|
| 1 | IT15 | TGACAGCAGTGTTGATAAA | NM_002111 | 2071-2089 |
| 2 | IT15 | AAGAACGAGTGCTCAATAA | NM_002111 | 2862-2880 |
| 3 | IT15 | TTTATGAACTGACGTTACA | NM_002111 | 1221-1239 |
| 4 | IT15 | GGAGTATTGTGGAACTTAT | NM_002111 | 1404-1422 |
| 5 | IT15 | GAGTATTGTGGAACTTATA | NM_002111 | 1405-1423 |
| 6 | IT15 | AGACCGTGTGAATCATTGT | NM_002111 | 442-460 |
| 7 | IT15 | GGTTACAGCTCGAGCTCTA | NM_002111 | 645-663 |
| 8 | IT15 | GGTTTTGTTAAAGGCCTTC | NM_002111 | 898-916 |
| 9 | IT15 | TGACAGCAGTGTTGATAAATTTGTGTT | NM_002111 | 2071-2097 |
| 10 | IT15 | AAGAACGAGTGCTCAATAATGTTGTCA | NM_002111 | 2862-2888 |
| 11 | IT15 | TTTATGAACTGACGTTACATCATACAC | NM_002111 | 1221-1247 |
| 12 | IT15 | GGAGTATTGTGGAACTTATAGCTGGAG | NM_002111 | 1404-1430 |
| 13 | IT15 | GAGTATTGTGGAACTTATAGCTGGAGG | NM_002111 | 1405-1431 |
| 14 | IT15 | AGACCGTGTGAATCATTGTCTGACAAT | NM_002111 | 442-468 |
| 15 | IT15 | GGTTTTGTTAAAGGCCTTCATAGCGAA | NM_002111 | 898-924 |
| 42 | BACE1 | AAGGGTGTGTATGTGCCCTAC | NM_012104 | 837-857 |
| 43 | BACE1 | AATTGGCTTTGCTGTCAGCGC | NM_012104 | 1697-1717 |

TABLE 2-continued

Non-limiting examples of sequences suitable for RNAi agents which can be used for IT15, BACE1, a-synuclein, or SOD1 inhibition.

| SEQ ID NO: | Target Gene | siRNA Sequence | Accession # | Position within Accession # |
|---|---|---|---|---|
| 44 | BACE1 | AAGACTGTGGCTACAACATTC | NM_012104 | 1783-1803 |
| 45 | BACE1 | AAGGCTGCCTGGAGAAAGGAT | NM_012104 | 3308-3328 |
| 46 | BACE1 | CACTGAATCGGACAAGTTCTT | NM_012104 | 950-970 |
| 47 | BACE1 | CATGATCATTGGTGGTATCGA | NM_012104 | 1163-1183 |
| 48 | BACE1 | CATCCTTCCTCAGCAATACCT | NM_012104 | 1541-1561 |
| 49 | BACE1 | CAGACGCTCAACATCCTGGTG | NM_012104 | 717-737 |
| 50 | a-synuclein | CTACGAACCTGAAGCCTAA | NM_007308 | 334-352 |
| 51 | a-synuclein | TCAAGACTACGAACCTGAA | NM_007308 | 811-829 |
| 52 | a-synuclein | CATTAGCCATGGATGTATT | NM_007308 | 6-24 |
| 53 | a-synuclein | ACGAACCTGAAGCCTAAGA | NM_007308 | 336-354 |
| 54 | a-synuclein | GTACAAGTGCTCAGTTCCA | NM_007308 | 405-423 |
| 55 | a-synuclein | GCTTCAATCTACGATGTTA | NM_007308 | 589-607 |
| 56 | a-synuclein | CTAAGTGACTACCACTTAT | NM_007308 | 625-643 |
| 57 | a-synuclein | GTTCAGAAGTTGTTAGTGA | NM_007308 | 676-694 |
| 58 | a-synuclein | AGTTGTTAGTGATTTGCTA | NM_007308 | 683-701 |
| 59 | a-synuclein | GACGTATTGTGAAATTTGT | NM_007308 | 755-773 |
| 60 | SOD1 | TCATCAATTTCGAGCAGAA | NM_000454 | 201-219 |
| 61 | SOD1 | TGAGTTTGGAGATAATACA | NM_000454 | 295-313 |
| 62 | SOD1 | TGGCCGATGTGTCTATTGA | NM_000454 | 432-450 |
| 63 | SOD1 | CGATGTGTCTATTGAAGAT | NM_000454 | 436-454 |
| 64 | SOD1 | GCATTAAAGGACTGACTGA | NM_000454 | 252-270 |
| 65 | SOD1 | TCGTTTGGCTTGTGGTGTA | NM_000454 | 577-595 |
| 66 | SOD1 | AATTTCGAGCAGAAGGAAAGT | NM_000454 | 206-226 |
| 67 | SOD1 | AAGCATTAAAGGACTGACTGA | NM_000454 | 250-270 |
| 68 | SOD1 | AATGTGACTGCTGACAAAGAT | NM_000454 | 407-427 |
| 69 | SOD1 | AAGATTCTGTGATCTCACTCT | NM_000454 | 450-470 |

In another embodiment, the gene involved in the neurodegenerative disease is the BACE1 gene. In another embodiment, the gene involved in the neurodegenerative disease is the alpha-synuclein gene. In yet another embodiment, the gene involved in the neurodegenerative disease is SOD1 gene. RNAi agents for these genes are particularly preferred for combinations with NGF, GDNF, and IGF-1 or VEGF, respectively, but other combinations are also possible, such as an RNAi agent capable of inhibiting expression of the IT15 gene and GDNF.

A person of the ordinary skill in the art will appreciate that the invention is not limited to the RNAi agents comprising any one of SEQ. IDs NO. 1-15 and that other RNAi agents are also suitable for the compositions, systems, and methods of the instant invention.

In one embodiment, the RNAi agent is in a form of an siRNA molecule. The siRNA molecules targeted to desired sequence can be designed based on criteria well known in the art (see e.g., Elbashir et al., *EMBO J.* 20:6877 (2001)). For example, the target segment of the target mRNA preferably should begin with AA (most preferred), TA, GA, or CA; the GC ratio of the siRNA molecule preferably should be 45-55%; the siRNA molecule preferably should not contain three of the same nucleotides in a row; the siRNA molecule preferably should not contain seven mixed G/Cs in a row; the siRNA molecule preferably should comprise two nucleotide overhangs (preferably TT) at each 3' terminus; the target segment preferably should be in the ORF region of the target mRNA and preferably should be at least 75 by after the initiation ATG and at least 75 by before the stop codon; and the target segment preferably should not contain more than 16-17 contiguous base pairs of homology to other coding sequences. The length of one strand of siRNA should be between 16 and 30 bases. Thus in different embodiment, the length of one strand of siRNA is 17, 18, 19, 20, 21, 22, 23, 24, 25, 26, 27, 28, or 29 nucleotides long.

Based on some or all of these criteria, siRNA molecules targeted to desired sequences can be designed by one of skill in the art using the aforementioned criteria or other known criteria (e.g., Gilmore et al., *J. Drug Targeting* 12:315 (2004); Reynolds et al., *Nature Biotechnol.* 22:326 (2004); Ui-Tei et al., *Nucleic Acids Res.* 32:936 (2004)). Such criteria are available in various web-based program formats useful for designing and optimizing siRNA molecules (e.g., siDESIGN Center at Dharmacon; BLOCK-iT RNAi Designer at Invitrogen; siRNA Selector at Wistar Insitute; siRNA Selection Program at Whitehead Institute; siRNA Design at Integrated DNA Technologies; siRNA Target Finder at Ambion; and siRNA Target Finder at Genscript).

Short hairpin RNA (shRNA) molecules fold back on themselves to produce the requisite double-stranded portion (Yu et al., *Proc. Natl. Acad. Sci. USA* 99:6047 (2002)). Such single-stranded RNA molecules can be produced using DNA templates (e.g., Yu et al., *Proc. Natl. Acad. Sci. USA* 99:6047 (2002)). In view of the length criteria for the siRNA, the length of the shRNA should be adjusted accordingly.

It is not necessary that the second and the third nucleic acid sequences be joined immediately adjacent each other. In different embodiments of the invention, spacers may be used between the second and the third nucleic acid sequences. The spacers may be as short as 1 nucleotide, as long as 3,000 nucleotides, or any length between these two numbers. In one embodiment, the second and the third nucleic acid sequences are separated by 200 to 1000 nucleotides.

Further, the order of the second and the third sequences is not important. Thus, in one set of the embodiments, the second nucleic acid sequence is upstream of the third nucleic acid sequence. In another set of embodiments, the second nucleic acid sequence is downstream of the third nucleic acid sequence.

A person of the ordinary skill in the art will appreciate that in any of the embodiments disclosed above or below, the first nucleic acid sequence may further optionally comprise one or more promoters. For example, the first nucleic acid sequence may include a first promoter which is operably linked to the second nucleic acid sequence. In another embodiment, the first nucleic acid sequence may also comprise a second promoter which is operably linked to the third nucleic acid sequence. It would be understood by a person of the ordinary skill in the art that the first nucleic acid sequence may comprise only the first promoter, or only the second promoter, or both the first and the second promoters in different embodiments of the invention.

Suitable examples of the first and the second promoters may independently include promoters which may be constitutively active or tissue-specific. Promoters for eukaryotic RNA polymerase I (pol I), RNA polymerase II (pol II), or RNA polymerase III (pol III) may be used to direct transcription of the second and third nucleic acid sequences as is known and appreciated in the art. Several investigators have demonstrated that RNA molecules can be expressed from such promoters can function in mammalian cells (e.g. Kashani-Sabet et al., 1992, Antisense Res. Dev., 2, 3-15; Ojwang et al., 1992, Proc. Natl. Acad. Sci. USA, 89, 10802-6; Chen et al., 1992, Nucleic Acids Res., 20, 4581-9; Yu et al., 1993, Proc. Natl. Acad. Sci. USA, 90, 6340-4; L'Huillier et al., 1992, EMBO J, 11, 4411-8; Lisziewicz et al., 1993, Proc. Natl. Acad. Sci. U.S.A, 90, 8000-4; Thompson et al., 1995, Nucleic Acids Res., 23, 2259; Sullenger & Cech, 1993, Science, 262, 1566). In one embodiment, the suitable promoters include constitutive RNA polymerase II promoters (e.g., cytomegalovirus (CMV) promoter, the SV40 early promoter region, the promoter contained in the 3' long terminal repeat of Rous sarcoma virus (RSV), the herpes thymidine kinase (TK) promoter, and the chicken beta-actin promoter), cardiac-tissue-specific RNA polymerase II promoters (e.g., the ventricular myosin light chain 2 (MLC-2v) promoter, and the sodium-calcium exchanger gene H1 promoter (NCX1H1)), and RNA polymerase III promoters (e.g., U6, H1, 7SK and 7SL). A non-limiting example of a tissue-specific promoter is neuron-specific enolase promoter. It has been shown that 1.8 kb rat neuron-specific enolase promoter in combination with woodchuck posttranscriptional regulatory element is sufficient for expression of gene-delivered BDNF in rat brain. Kells et al., 2005).

In another embodiment, transcription units may be used. More specifically, transcription units such as the ones derived from genes encoding U6 small nuclear (snRNA), transfer RNA (tRNA), and adenovirus VA RNA are useful in generating high concentrations of desired RNA molecules such as small interfering RNA in cells (Thompson et al., supra; Couture and Stinchcomb, 1996, supra; Noonberg et al., 1994, Nucleic Acid Res., 22, 2830; Noonberg et al., U.S. Pat. No. 5,624,803; Good et al., 1997, Gene Ther., 4, 45; Beigelman et al., International PCT Publication No. WO 96118736; all of these publications are incorporated by reference herein). The above small interfering RNA transcription units can be incorporated into a variety of vectors for introduction into mammalian cells, including but not restricted to, plasmid DNA vectors, viral DNA vectors (such as adenovirus or adeno-associated virus vectors), or viral RNA vectors (such as retroviral or alphavirus vectors).

The first nucleic acid sequence may further comprise additional functional sequences, such as an internal ribosomal entry site (IRES) and sequences that terminate transcription.

The first nucleic acid sequence according to any of the embodiments of the instant aspect of the invention may be delivered as a naked sequence or, preferably, included within a vector, which may be either a plasmid vector or a viral vector. It is also possible that non-viral vectors, such as plasmid DNA delivered alone or complexed with liposomal compounds or polyethyleneamine, may be used to deliver the first nucleic acid sequence to neurons in the brain.

Although numerous expression vectors can be used to express siRNA molecules and the neurotrophic factor molecules in cells (Dorsett and Tuschl, *Nat. Rev. Drug Discov.* 3:318 (2004)), viral expression vectors are preferred, particularly those that efficiently transduce brain cells (e.g., alphaviral, lentiviral, retroviral, adenoviral, adeno-associated viral (AAV)) (Williams and Koch, *Annu. Rev. Physiol.* 66:49 (2004); del Monte and Hajjar, *J. Physiol.* 546.1:49 (2003). Both adenoviral and AAV vectors have been shown to be effective at delivering transgenes (including transgenes directed to diseases) into brain. See, e.g., Kells (2005), Machida et al., *Biochem. Biophys. Res. Commun.*, 343(1): 190-7 (2006).

The method of constructing the first nucleic acid sequence and the appropriate vector constructs are well known in the art. These methods include, without limitation, any combinations of PCR and/or RT-PCR, endonuclease restriction, ligation, and subcloning. Further, mRNA, cDNA, and, if needed, amino acid sequences of any and all full molecules (e.g., IT15 gene (SEQ. ID. NO. 16), BACE1 gene (SEQ. ID. NOs. 17-20 for transcript variants A, B, C, and D, respectively), alpha synuclein gene (SEQ. ID. NOs. 21 and 22 for transcript variants NACP140 and NACP112, respectively), SOD-1 gene (SEQ. ID. NO. 23), BDNF (SEQ. ID. NOs. 24-29 for transcript variants 1-6, respectively), GDNF (SEQ. ID. NOs. 30-32 for transcript variants 1-3, respectively), NGF (SEQ. ID. NO. 33), IGF-1 (SEQ. ID. NO. 34), VEGF (SEQ. ID. NOs. 35-41 for transcript variants 1-7, respectively), etc.) are well known in the art and available from GenBank. Exemplary sequences are also provided in the "Sequence Listing" section accompanying the instant disclosure.

Shorter nucleic acid sequences, e.g., the third nucleic acid sequence may be produced by multiple methods. There are currently five methods for producing siRNA: chemical synthesis, in vitro transcription, preparation of siRNA population by digestion, in vivo expression of hairpin siRNA from an expression vector, and in vivo expression of siRNA from a PCR-derived expression cassette. All these methods may be used for the instant invention.

Examples of additional sequences suitable for the RNAi agents are shown in Table 2 above. SEQ. ID. NOs. 42, 43, 44, 45, 46, 47, 48, and 49 relate to suppressing BACE1 mRNA; SEQ. ID. NOs. 50, 51, 52, 53, 54, 55, 56, 57, 58 and 59 relate to suppressing α-synuclein mRNA; and SEQ. ID NOs. 60, 61, 62, 63, 64, 65, 66, 67, 68, and 69 relate to suppressing SOD1 mRNA.

Accordingly, a person of the ordinary skill in the art will not be burdened with undue experimentation while producing nucleic acid sequences and proteins or fragments thereof which are claimed or disclosed in the instant invention.

When the appropriate constructs are prepared (including, without limitation, vectors containing the first nucleic acid sequence, vectors containing only RNAi agent, or vectors containing nucleic acid sequence of the neurotrophic factor or the functional fragment thereof), these components can be produced at a large scale.

For example, the vectors containing the RNAi agent (including the vectors containing the first nucleic acid sequence) can be produced in large quantities by using packaging cell strains such as those described in J. M. Coffin, S. H. Hughes & H. E. Varmus (eds.), Retroviruses, Cold Spring Harbor Laboratory Press. Other methods for producing retroviruses and for infecting cells in vitro or in vivo are described in Current Protocols in Molecular Biology, Ausubel, F. M. et al. (eds.) Greene Publishing Associates, (1989), Sections 9.10-9.14.

Further, if it is a protein which is used for the therapy according to any of the methods of the instant invention (e.g., for using the neurotrophic factor or the functional fragment thereof in a form of protein), expression systems may be used. In that method, the vector containing the nucleic acid sequence encoding the protein of interest or the functional fragment thereof is later introduced to host cells. The choice of the host cell system depends largely on the type of the vector and the type of the promoter. In general, the host cells include, without limitations, prokaryotic, yeast, insect, and mammal cells.

Further, depending on the type of the host cell, the codons of the nucleic acid sequences encoding the amino acid sequences of the instant invention can be selected for optimal expression in prokaryotic or eukaryotic systems. Host-vector systems include but are not limited to the following: bacteria transformed with bacteriophage DNA, plasmid DNA, or cosmid DNA; microorganisms such as yeast containing yeast vectors; mammalian cell systems infected with virus (e.g., vaccinia virus, adenovirus, etc.); and insect cell systems infected with virus (e.g., baculovirus). The expression elements of these vectors vary in their strength and specificities. Depending upon the host-vector system utilized, any one of a number of suitable transcription and translation elements can be used.

In another set of embodiments, the invention provides a variety of formulations which can be used in combination with the compositions, methods and systems of the instant invention as described both above and below.

For example, in one embodiment of the present invention, the composition comprising the RNAi agent or precursors or derivatives thereof is formulated in accordance with standard procedure as a pharmaceutical formulation adapted for delivered administration to human beings and other mammals. Typically, formulations for intravenous administration are solutions in sterile isotonic aqueous buffer.

Where necessary, the formulation may also include a solubilizing agent and a local anesthetic to ameliorate any pain at the site of the injection. Generally, the ingredients are supplied either separately or mixed together in unit dosage form, for example, as a dry lyophilized powder or water free concentrate in a hermetically sealed container such as an ampule or sachette indicating the quantity of active agent. Where the formulation is to be administered by infusion, it can be dispensed with an infusion bottle containing sterile pharmaceutical grade water or saline. Where the formulation is administered by injection, an ampule of sterile water for injection or saline can be provided so that the ingredients may be mixed prior to administration.

In cases other than intravenous administration, the formulation can contain minor amounts of wetting or emulsifying agents or pH-buffering agents. The formulation can be a liquid solution, suspension, emulsion, gel, polymer, or sustained-release formulation. The formulation can further include traditional binders and carriers, as would be known in the art. Formulations can include standard carriers such as pharmaceutical grades of mannitol, lactose, starch, magnesium stearate, sodium saccharide, cellulose, magnesium carbonate, etc., inert carriers having well established functionality in the manufacture of pharmaceuticals. Various delivery systems are known and can be used to administer a therapeutic of the present invention including encapsulation in liposomes, microparticles, microcapsules, and the like. Thus, in one embodiment, the RNAi agents of the invention are added directly, or can be complexed with cationic lipids, packaged within liposomes, packaged within viral vectors, or otherwise delivered to target cells or tissues.

In a second aspect, the invention provides a method of treating a patient affected with a neurodegenerative disease comprising: administering to said patient an RNAi agent capable of inhibiting expression of a gene responsible for a neurodegenerative disease and at least one of a neurotrophic factor or a functional fragment thereof.

According to different embodiments of this aspect of the invention, the RNAi agent, including RNAi agents comprising any one of SEQ. ID. NOs. 1-15 and 42-69, may be delivered within a vector or as a vectorless, or naked, nucleic acid, including DNA-RNA hybrids. If the RNAi agent is administered in a naked form, it may be chemically modified (e.g., the RNAi agent may include one or more modified nucleotides) for improving its stability and increasing its penetration into the neurons. The RNAi agent suitable for this aspect of the invention can comprise modified nucleotides at various locations, whether in base-paired position or non-base-paired position, including the loop, if the RNAi agent is an shRNA, or the overhang positions. The modified nucleotides may be located either on the sense or the antisense part of the RNAi agent.

For example, in one embodiment, the pyrimidine nucleotides in the sense region of the RNAi agent are 2'-O-methylpyrimidine nucleotides or 2'-deoxy-2'-fluoro pyrimidine nucleotides and the purine nucleotides present in the sense region are 2'-deoxy purine nucleotides. In another embodiment, the pyrimidine nucleotides in the sense region are 2'-deoxy-2'-fluoro pyrimidine nucleotides and the purine nucleotides present in the sense region are 2'-O-methyl purine nucleotides. In another embodiment, the pyrimidine nucleotides in the sense region are 2'-deoxy-2'-fluoro pyrimidine nucleotides and the purine nucleotides present in the sense region are 2'-deoxy purine nucleotides.

Additional non-limiting examples of chemical modification of the nucleotides in the RNAi agent include 2'-O-trifluoromethyl nucleotides, 2'-O-ethyl-trifluoromethoxy nucleotides, or 2'-O-difluoromethoxy-ethoxy nucleotides. The RNAi agent can also comprise at least one modified internucleotidic linkage, such as a phosphorothioate linkage. In one embodiment, the 2'-deoxy-2'-fluoronucleotides are present at specifically selected locations in the RNAi agent that are sensitive to cleavage by ribonucleases, such as locations having pyrimidine nucleotides.

In a further set of embodiments, the RNAi agent may be chemically modified on a 3' end, a 5' end, or both the 3' end and the 5' end. These terminal modifications protect the nucleic acid molecule from exonuclease degradation and may help in delivery and/or localization within a cell. Examples of moieties suitable for the modification of the 5' end of the RNAi agent include, without limitations, glyceryl, inverted deoxy abasic residue (moiety); 4',5'-methylene nucleotide; 1-(beta-D-erythrofuranosyl)nucleotide, 4'-thio nucleotide; carbocyclic nucleotide; 1,5-anhydrohexitol nucleotide; L-nucleotides; alpha-nucleotides; modified base nucleotide; phosphorodithioate linkage; threo-pentofuranosyl nucleotide; acyclic 3',4'-seco nucleotide; acyclic 3,4-dihydroxybutyl nucleotide; acyclic 3,5-dihydroxypentyl nucleotide, 3'-3'-inverted nucleotide moiety; 3'-3'-inverted abasic moiety; 3'-2'-inverted nucleotide moiety; 3'-2'-inverted abasic moiety; 1,4-butanediol phosphate; 3'-phosphoramidate; hexylphosphate; aminohexyl phosphate; 3'-phosphate; 3'-phosphorothioate; phosphorodithioate; or bridging or non-bridging methylphosphonate moiety.

Non-limiting examples of the moieties suitable for modification of the 3'-end of the RNAi agent include glyceryl, inverted deoxy abasic residue (moiety), 4',5'-methylene nucleotide; 1-(beta-D-erythrofuranosyl)nucleotide; 4'-thio nucleotide, carbocyclic nucleotide; 5'-amino-alkyl phosphate; 1,3-diamino-2-propyl phosphate; 3-aminopropyl phosphate; 6-aminohexyl phosphate; 1,2-aminododecyl phosphate; hydroxypropyl phosphate; 1,5-anhydrohexitol nucleotide; L-nucleotide; alpha-nucleotide; modified base nucleotide; phosphorodithioate; threo-pentofuranosyl nucleotide; acyclic 3',4'-seco nucleotide; 3,4-dihydroxybutyl nucleotide; 3,5-dihydroxypentyl nucleotide, 5'-5'-inverted nucleotide moiety; 5'-5'-inverted abasic moiety; 5'-phosphoramidate; 5'-phosphorothioate; 1,4-butanediol phosphate; 5'-amino; bridging and/or non-bridging 5'-phosphoramidate, phosphorothioate and/or phosphorodithioate, bridging or non bridging methylphosphonate and 5'-mercapto moieties.

Yet additional suitable modifications of the RNAi agent are described in details in U.S. patent application Ser. No. 11/450,856, filed on Jun. 9, 2006 (McSwiggen), which is incorporated herein by reference to the extent it is not inconsistent with the instant disclosure.

The RNAi agent, whether in the naked form or included within the first nucleic acid sequence according to any embodiment of the first aspect of the invention, may be delivered by intravenous, intranasal, intraocular, intraperitoneal, intracranial, or intrathecal injection. Preferably, the RNAi agent is in a formulation, which is preferably composed according to any of the embodiments described above.

The neurotrophic factor or the functional fragment thereof may be delivered to the patient in the form of another nucleic acid construct (e.g., another vector, using plasmid and viral vectors suitable for the first nucleic acid, as described above) or in the form of a protein. In a preferred embodiment, the neurotrophic factor or the fragment thereof is delivered in the form of protein. Again, the protein may be in the form of a formulation, which is preferably composed according to any of the embodiments described above.

Thus, at least four combinations are possible in this aspect of the invention. These combinations include: (a) delivery of the RNAi agent within a vector and delivery of the neurotrophic factor or a functional fragment thereof within the same or a different vector; (b) delivery of the RNAi agent within a vector and delivery of the neurotrophic factor or a functional fragment thereof in a form of protein; (c) delivery of the RNAi agent (whether chemically modified or unmodified) in a vectorless form and delivery of the neurotrophic factor or a functional fragment thereof within a vector; and (d) delivery of the RNAi agent (whether chemically modified or unmodified) in a vectorless form and delivery of the neurotrophic factor or a functional fragment thereof in a form of protein.

A person of the ordinary skill in the art will appreciate that the neurotrophic factor or the functional fragment thereof and the RNAi agent may be delivered to the patient simultaneously or independently of each other, by the same or by a different delivery route.

The third aspect of the invention provides a method of treating a patient with a neurodegenerative disease comprising: administering to said patient a first nucleic acid sequence of any one of the embodiments of the first aspect, as disclosed above.

In general, the amount of the therapeutic agent(s) according to any embodiment of the methods the present invention which will be effective in the treatment of a particular disorder will depend on the nature of the disorder, and can be determined by standard clinical techniques, well established in the administration of therapeutics. The precise dose to be employed in the formulation will also depend on the route of administration, and the seriousness of the disease, and should be decided according to the judgment of the practitioner and the patient's needs.

In a set of embodiments, where the RNAi agent is included within a viral vector (including the vectors comprising the first nucleic acid sequence), suitable dose ranges for intracranial administration are generally about $10^3$ to $10^{15}$ infectious units of viral vector per microliter delivered in 1 to 3000 microliters of single injection volume. Additional amounts of infectious units of vector per micro liter would generally contain about $10^4$, $10^5$, $10^6$, $10^7$, $10^8$, $10^9$, $10^{10}$, $10^{11}$, $10^{12}$, $10^{13}$, $10^{14}$ infectious units of viral vector delivered in about 10, 50, 100, 200, 500, 1000, or 2000 microliters. Effective doses may be extrapolated from dose-responsive curves derived from in vitro or in vivo test systems.

The practitioner may also chemically modify the neurotrophic factors in the form of protein. Such modifications may be helpful for such properties as the ability of the therapy (either in the form of nucleic acid sequence or in the form of protein) to get through the blood-brain barrier (BBB) or to get through the cell membrane.

A suitable non-limiting example of a penetration enhancer is polyethylene glycol, or PEG. A receptor-specific monoclonal antibody (mAb) directed at a BBB receptor, such as the insulin receptor or transferrin receptor (TfR), may be attached to PEG strands and thus transport PEG through the BBB.

Similarly to the nucleic acid sequences, the proteins of the instant invention (e.g., the neurotrophic factor or the fragment thereof, including, without limitation, BDNF, GDNF, NGF, IGF-1, and VEGF) may be delivered as a formulation according to the guidelines known in the art. Exemplary components of suitable formulations have been described in connection with the nucleic acid sequence formulations. The same components would be suitable for the protein formulations.

A person of the ordinary skill in the art will understand and appreciate that the methods of the second and the third aspect of the invention may be combined: thus the patient will receive the neurotrophic factor or the functional fragment thereof in the form of a protein, the RNAi agent (either in a naked form or in a vector), and a vector comprising the first nucleic acid sequence. Any combination of these two compounds may be delivered simultaneously, or these compounds may be delivered at different times. A person of the ordinary skill in the art will also appreciate that these compounds may be delivered by different routes which may be independently selected from intracranial, intravenous, intranasal, intraocular, and intrathecal delivery routes. In one embodiment, the RNAi agents or combinations of the RNAi agents and neurotrophic factors can be locally administered to relevant tissues ex vivo, or in vivo through injection, infusion pump or stent, with or without their incorporation in biopolymers.

In a fourth aspect, the invention provides a system which is suitable for practicing the methods according to the second and the third aspects of the invention, where at least one compound is delivered intracranially. Generally, the system comprises: a) a means for mapping the location of a neuron within the brain of the live patient; b) an intracranial access device providing fluid access to the neuron; and c) the therapy.

A person of the ordinary skill in the art will appreciate that in one set of embodiments, the therapy comprises the first nucleic acid sequence according to any of the embodiments described above. In another set of embodiments, the therapy comprises the RNAi agent and/or the neurotrophic factor.

A person of the ordinary skill in the art will further appreciate that multiple stents or catheters, preferably catheters having access ports, can be implanted in a given patient for a complete therapy. In a preferred embodiment, there is at least one port and catheter system per cerebral or cerebellar hemisphere and perhaps several. Once the implantations are performed by a practitioner, the practitioner (who may be the same or different from the practitioner who implanted the catheters) can perform a course of therapy according to the methods described in the second and the third aspects of the invention over a period of weeks to months, along with monitoring for therapeutic effect over time. The devices can remain implanted for several months or years for a full course of therapy. After confirmation of therapeutic efficacy, the access ports might optionally be explanted, and the catheters can be sealed and abandoned or explanted as well. The device material should not interfere with magnetic resonance imaging, and, of course, the access port and catheter materials and any surface coatings must be compatible with the compounds which are delivered through these devices, including, in different embodiments, the nucleic acid sequences, including the naked RNAi agent, the vector comprising the RNA agent, and/or the proteins including the neurotrophic factors or the functional fragments thereof.

In one preferred embodiment, the delivery is through the use of implanted, indwelling, intraparenchymal catheters that provide a means for directly injecting small volumes of fluid containing AAV or other vectors into local brain tissue. The proximal end of these catheters may be connected to an implanted, intracerebral access port surgically affixed to the patient's cranium or to an implanted drug pump located in the patient's torso.

Figure 2:
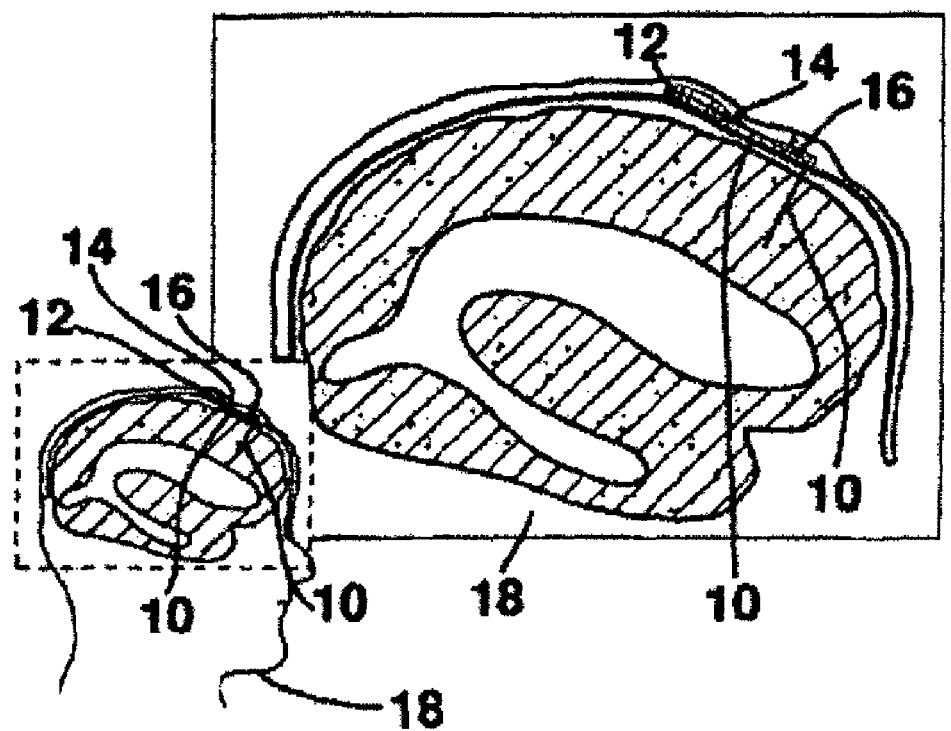

Examples of the delivery devices within the scope of the present invention include the Model 8506 investigational device (by Medtronic, Inc. of Minneapolis, Minn.), which can be implanted subcutaneously on the cranium and provides an access port through which therapeutic agents may be delivered to the brain. Delivery occurs through a stereotactically implanted polyurethane catheter. The Model 8506 is schematically depicted in FIGS. 1 and 2. Two models of catheters that can function with the Model 8506 access port include the Model 8770 ventricular catheter by Medtronic, Inc., for delivery to the intracerebral ventricles, which is disclosed in U.S. Pat. No. 6,093,180, incorporated herein by reference, and the IPA1 catheter by Medtronic, Inc., for delivery to the brain tissue itself (i.e., intraparenchymal delivery), disclosed in U.S. Ser. Nos. 09/540,444 and 09/625,751, which are incorporated herein by reference. The latter catheter has multiple outlets on its distal end to deliver the therapeutic agent to multiple sites along the catheter path.

In addition to the aforementioned device, the delivery of the components of the therapies described above (including, without limitations, the RNAi agent, the first nucleic acid sequence, whether naked or within the vector, the neurotrophic factor or the functional fragment thereof) according to the embodiments described previously in accordance with the present invention can be accomplished with a wide variety of devices, including but not limited to U.S. Pat. Nos. 5,735,814, 5,814,014, and 6,042,579, all of which are incorporated herein by reference. Using the teachings of the present invention those of skill in the art will recognize that these and other devices and systems may be suitable for delivery of the therapies according to any of the embodiments of the first, the second, and the third aspects of the invention for the treatment of neurodegenerative diseases in accordance with the present invention.

In an additional set of embodiments suitable for practicing the methods according to any of the embodiments of the instant invention, the system further comprises a pump, which may be worn on a patient's clothing (e.g., on a belt or in a pocket) or implanted outside the brain. The pump is preferably coupled to a proximal end of the catheter, and operating the pump delivers the predetermined dosage of the therapeutic (e.g., the RNAi agent, the first nucleic acid sequence, whether naked or within the vector, the neurotrophic factor) through the discharge portion of the catheter.

In another set of embodiments for delivering the compositions of any of the embodiments disclosed above according to the methods of any embodiment of the invention disclosed above, the intracranial access device is a guide cannula. The cannula is preferably attached to the intracranial access port and preferably sealed on the distal end (the end outside of the patient's skull) or both the distal end and the proximal end. The cannula may be manufactured from a tissue-compatible material (e.g., a material which is not toxic at physiological conditions and degradation of which at physiological conditions does not result in toxic residues), and, in one embodiment, a proximate end of the cannula is formed with tissue-compatible material having antibacterial properties.

When the practitioner desires to administer the treatment, he may insert the catheter into the cannula, as disclosed above, and deliver the therapy, such as a therapy according to any one of the embodiments described above.

In yet another embodiment, the cannula is functionally connected with a syringe, such as a microsyringe, comprising a catheter for insertion into the guide tube; a flow regulator through which the biologic, chemical, or pharmaceutical agent is released at a predetermined rate; a delivery chamber containing a predetermined amount of fluid volume and biologic, chemical, or pharmaceutical agent to be injected into the brain tissue; and a second chamber (separate from the first chamber) containing a septum that acts as a piston or plunger to deliver the material through the catheter. The second chamber may be filled with hydraulic fluid, oil, gas, air, or any other suitable substance capable of providing controlled pressures for releasing the biologic, chemical, or pharmaceutical agent into the brain tissue. A non-limiting example of a suitable microsyringe has been disclosed in a co-pending application Ser. No. 11/562,282, (Kaemmerer), filed Nov. 21, 2006.

Generally, neurons affected with Huntington's disease reside in striatum, neurons affected with Alzheimer's disease reside in nucleus basalis of Meynart and the cerebral cortex, and neurons affected with Parkinson's disease reside in the substantia nigra. Thus, in different embodiments depending on the disease, the catheter or other intracranial access device delivers the therapies according to the methods of the instant invention to nucleus basalis of Meynart and the cerebral cortex, striatum, and/or the substantia nigra.

The location of a neuron or neurons affected with a neurodegenerative disease (e.g., Huntington's, Alzheimer's, Parkinson's) may be mapped by many methods. For example, for some applications, it can be mapped by stereotactical or gross anatomical atlases. In other embodiments, when the precise location of the targeted area is crucial, other mapping means may be used in addition to stereotactical or gross anatomical atlases. Such mapping means include, without limitation, Positron Emission Tomography and Single Photon Emission Computed Tomography (PET and SPECT, respectively), pharmacological Magnetic Resonance Imaging (phMRI), functional MRI (fMRI), and contrast-enhanced computerized tomography (CT) scan.

In another embodiment, computer-aided atlas-based functional neurosurgery methodology can be used to accurately and precisely inject the deoxyribonucleic acid of the present invention. Such methodologies permit three-dimensional display and real-time manipulation of cerebral structures. Neurosurgical planning with mutually preregistered multiple brain atlases in all three orthogonal orientations is therefore possible and permits increased accuracy of target definition for treatment injection or implantation, reduced time of the surgical procedure by decreasing the number of tracts, and facilitates planning of more sophisticated trajectories. See, e.g., Nowinski, W. L. et al., Computer-Aided Stereotactic Functional Neurosurgery Enhanced by the Use of the Multiple Brain Atlas Database, IEEE Trans Med Imaging 19(1); 62-69:2000.

Further, in 2001, Medtronic, Inc. introduced a "mapping means" device, termed the Medtronic NT StealthStation® Treon™, into the marketplace. This medical system further refines the computerized technologies of multi-dimensional imaging and navigation to enable neurosurgeons to precisely plan, re-plan, and visualize a procedure as it proceeds deep within the brain for treating neurological disorders in a living human patient.

Certain embodiments of the invention will now be discussed in the following non-limiting prophetic example.

Prophetic Example 1

Overview

Combined RNAi and neurotrophic factor-based therapies have potential to treat a number of neurodegenerative diseases. This co-therapy can be achieved using a variety of strategies ranging from a single injection of virus encoding both therapeutic agents to life long infusions of the RNAi agent and the neurotrophic factor. Various combinations of acute and chronic methods of nucleic acid and/or protein factor delivery can be utilized.

Description of Transgenic Mice:

A number of transgenic animal models of HD have been developed that express full length or truncated portions of the HD gene containing expanded CAG repeat tracts. Many of these models demonstrate progressive motor deficits and/or neuropathologic alterations of reminiscent of HD (Bates and Gonitel, *Mol. Biotech.* 2006, 32:147, Wang and Qin, *Acta Pharmacologica Sinica.* 2006, 27(10):1287). Evaluation of combined RNAi and neurotrophic factor-based therapies can be performed in models that express mutant forms of the human HD gene as long as the sequences targeted by the siRNA of interest are present in the mutant transgene. For example, the BAC-HD mice developed by William Yang express the full length mutant HD protein (Htt) from the endogenous human Htt locus contained on a bacterial artificial chromosome (BAC) transferred to the mice (Gray et al. *Soc. Neurosci. Conf.* 2007, 765.10). The BAC-HD transgenic animals display many of the phenotypic features seen in adult-onset HD, including progressive and robust motor deficits, late onset hyperactivity, selective neuropathology restricted to the cortex and striatum, and a characteristic pattern of mhtt aggregation.

Experimental Protocol:

Study aim: To determine the behavioral and patho-histological alterations following delivery of an anti-HD RNAi and BDNF combination therapy to the striatum of BAC-HD mice.

A non-limiting example of the experimental design for accessing the effect of the combination treatment of the instant invention is illustrated in Table 3.

TABLE 3

Experimental groups: (n = 12, same sex ratio across treatment groups)

| Mice | Treatment | Comments |
|---|---|---|
| Wildtype FVB | Surgery and PBS injection | Wildtype FVB control |
| BAC-HD (FVB) | Surgery and PBS injection | BAC-HD FVB control |
| BAC-HD (FVB) | AAV-shRNA#5 (SEQ. ID. NO. 4) | Efficacy of anti-HD shRNA |
| BAC-HD (FVB) | AAV-shRNA#1 (SEQ. ID. NO. 1) | Efficacy of anti-HD shRNA |
| BAC-HD (FVB) | AAV-control shRNA | Control for shRNA |
| BAC-HD (FVB) | AAV-BDNF-GFP | Benefit from BDNF only |
| BAC-HD (FVB) | AAV-BDNF-GFP + AAV-shRNA#5 | Combined benefit of BDNF and anti-HD shRNA |

Surgery: The test or control articles are administered by acute bilateral striatal infusion to animals of ~3 month's age. Note: All AAV injections contain viral titers of $10^6$ to $10^9$ viral genomes.

Behavioral Measures: To be conducted at ~2, 5 and 8 months of age. Some or all of the following behavioral tests may be administered Rotarod for motor coordination
Open field for exploratory and locomotor behavior
Grip strength/stretch test, balanced beam test
Y maze alternation for memory These tests are well known in behavioral biology and are within the abilities of persons of ordinary skill in the art.

Body Weight Measures: The body weight of the animals is monitored weekly starting at 2 months of age.

Molecular and Histological Analyses: The molecular and histological analyses are conducted when animals are about 8 months of age (5 months post-surgery).

Some of the experiments are performed on fresh frozen tissue (dissection of striata, cortex, cerebellum): (n=8 per treatment group) by the methods known to those skilled in the art and not limited to the methods disclosed below:

Forebrain and cerebellar weight (n=8)
Mutant and endogenous htt, BDNF, and GAPDH mRNA expression (qRT-PCR) (n=4)
Mutant and endogenous Htt, BDNF, and housekeeping (tubulin or other) protein expression (western immunoblotting) (n=4)

Additional experiments are performed using 4% paraformaldehyde or alternate-perfuse-fixed tissue: (n=4 per treatment group)

Stereological striatal volume (NeuN-positive cell counting);
Immunohistochemical staining for neuropil aggregates (EM48), and degenerating neurons (amino cupric silver or toluidine blue);
Viral volume of distribution: fluorescence (GFP) imaging or immunohistochemistry (GFP and BDNF).

Every patent and non-patent publication cited in the instant disclosure is incorporated into the disclosure by reference to the same effect as if every publication is individually incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the following claims.

The invention claimed is:

1. A first nucleic acid sequence comprising:
   a second nucleic acid sequence encoding a neurotrophic factor or a functional fragment thereof; and
   a third nucleic acid sequence encoding an RNAi agent capable of inhibiting expression of a gene involved in a neurodegenerative disease, wherein the RNAi agent comprises a sequence selected from the group consisting of SEQ ID NOs: 1-15 and 42-69.

2. The first nucleic acid sequence of claim 1, wherein the first nucleic acid sequence is included within a vector.

3. The first nucleic acid sequence of claim 2, wherein the vector is a viral vector.

4. The first nucleic acid sequence of claim 3, wherein the viral vector is an AAV viral vector.

5. The first nucleic acid sequence of claim 1, further comprising a first promoter capable of regulating expression of at least a part of the second nucleic acid sequence.

6. The first nucleic acid sequence of claim 1, further comprising a second promoter capable of regulating expression of at least a part of the third nucleic acid sequence.

7. The first nucleic acid sequence of claim 1, wherein the gene involved in the neurodegenerative disease is an IT15 gene.

8. The first nucleic acid sequence of claim 7, wherein the nucleic acid sequence encoding an RNAi agent comprises a sequence selected from the group consisting of SEQ. ID. NOs. 1-15.

9. The first nucleic acid sequence of claim 7, wherein the neurotrophic factor is glial cell-derived neurotrophic factor (GDNF).

10. The first nucleic acid sequence of claim 7, wherein the neurotrophic factor is brain-derived neurotrophic factor (BDNF).

11. The first nucleic acid sequence of claim 1, wherein the gene involved in the neurodegenerative disease is an alpha synuclein gene.

12. The first nucleic acid sequence of claim 11, wherein the neurotrophic factor is GDNF.

13. The first nucleic acid sequence of claim 1, wherein the gene involved in the neurodegenerative disease is a BACE1 gene.

14. The first nucleic acid sequence of claim 13, wherein the neurotrophic factor is NGF.

15. The first nucleic acid sequence of claim 1, wherein the gene involved in the neurodegenerative disease is an SOD1 gene.

16. The first nucleic acid sequence of claim 15, wherein the neurotrophic factor is selected from the group consisting of VEGF, IGF-1, GDNF, and any combination thereof.

17. A cell comprising the first nucleic acid sequence of claim 1.

18. A pharmaceutical composition comprising the first nucleic acid sequence of claim 1.

19. A method of treating a neurodegenerative disease in a patient comprising administering to said patient:
   an RNAi agent capable of inhibiting expression of a gene involved in a neurodegenerative disease; and
   at least one of a neurotrophic factor or a functional fragment thereof, wherein the RNAi agent comprises a sequence selected from the group consisting of SEQ ID NOs: 1-15 and 42-69.

20. The method of claim 19, wherein the RNAi agent is a vectorless molecule.

21. The method of claim 20, wherein the RNAi agent comprises a chemical modification.

22. The method of claim 21, wherein the chemical modification reduces alteration of said RNAi agent by endonucleases or exonucleases.

23. The method of claim 19, wherein the neurotrophic factor or the functional fragment thereof is administered in a form of a nucleic acid sequence encoding said neurotrophic factor or said functional fragment thereof and is included within a vector.

24. The method of claim 23, wherein said vector does not include the RNAi agent.

25. The method of claim 19 wherein the neurotrophic factor or the functional fragment thereof is administered in the form of a protein.

* * * * *

SEQUENCE LISTING

```
<160> NUMBER OF SEQ ID NOS: 69

<210> SEQ ID NO 1
<211> LENGTH: 19
<212> TYPE: DNA
<213> ORGANISM: Artificial
<220> FEATURE:
<223> OTHER INFORMATION: Artificial RNAi Sequence

<400> SEQUENCE: 1
tgacagcagt gttgataaa                                                19

<210> SEQ ID NO 2
<211> LENGTH: 19
<212> TYPE: DNA
<213> ORGANISM: Artificial
<220> FEATURE:
<223> OTHER INFORMATION: Artificial RNAi Sequence

<400> SEQUENCE: 2
aagaacgagt gctcaataa                                                19

<210> SEQ ID NO 3
<211> LENGTH: 19
<212> TYPE: DNA
<213> ORGANISM: Artificial
<220> FEATURE:
<223> OTHER INFORMATION: Artificial RNAi Sequence

<400> SEQUENCE: 3
tttatgaact gacgttaca                                                19

<210> SEQ ID NO 4
<211> LENGTH: 19
<212> TYPE: DNA
<213> ORGANISM: Artificial
<220> FEATURE:
<223> OTHER INFORMATION: Artificial RNAi Sequence
```

```
<400> SEQUENCE: 4
ggagtattgt ggaacttat                                                  19

<210> SEQ ID NO 5
<211> LENGTH: 19
<212> TYPE: DNA
<213> ORGANISM: Artificial
<220> FEATURE:
<223> OTHER INFORMATION: Artificial RNAi Sequence

<400> SEQUENCE: 5
gagtattgtg gaacttata                                                  19

<210> SEQ ID NO 6
<211> LENGTH: 19
<212> TYPE: DNA
<213> ORGANISM: Artificial
<220> FEATURE:
<223> OTHER INFORMATION: Artificial RNAi Sequence

<400> SEQUENCE: 6
agaccgtgtg aatcattgt                                                  19

<210> SEQ ID NO 7
<211> LENGTH: 19
<212> TYPE: DNA
<213> ORGANISM: Artificial
<220> FEATURE:
<223> OTHER INFORMATION: Artificial RNAi Sequence

<400> SEQUENCE: 7
ggttacagct cgagctcta                                                  19

<210> SEQ ID NO 8
<211> LENGTH: 19
<212> TYPE: DNA
<213> ORGANISM: Artificial
<220> FEATURE:
<223> OTHER INFORMATION: Artificial RNAi Sequence

<400> SEQUENCE: 8
ggttttgtta aaggccttc                                                  19

<210> SEQ ID NO 9
<211> LENGTH: 27
<212> TYPE: DNA
<213> ORGANISM: Artificial
<220> FEATURE:
<223> OTHER INFORMATION: Artificial RNAi Sequence

<400> SEQUENCE: 9
tgacagcagt gttgataaat ttgtgtt                                         27

<210> SEQ ID NO 10
<211> LENGTH: 27
<212> TYPE: DNA
<213> ORGANISM: Artificial
<220> FEATURE:
<223> OTHER INFORMATION: Artificial RNAi Sequence

<400> SEQUENCE: 10
aagaacgagt gctcaataat gttgtca                                         27

<210> SEQ ID NO 11
<211> LENGTH: 27
<212> TYPE: DNA
```

```
<213> ORGANISM: Artificial
<220> FEATURE:
<223> OTHER INFORMATION: Artificial RNAi Sequence

<400> SEQUENCE: 11
tttatgaact gacgttacat catacac                                          27

<210> SEQ ID NO 12
<211> LENGTH: 27
<212> TYPE: DNA
<213> ORGANISM: Artificial
<220> FEATURE:
<223> OTHER INFORMATION: Artificial RNAi Sequence

<400> SEQUENCE: 12
ggagtattgt ggaacttata gctggag                                          27

<210> SEQ ID NO 13
<211> LENGTH: 27
<212> TYPE: DNA
<213> ORGANISM: Artificial
<220> FEATURE:
<223> OTHER INFORMATION: Artificial RNAi Sequence

<400> SEQUENCE: 13
gagtattgtg gaacttatag ctggagg                                          27

<210> SEQ ID NO 14
<211> LENGTH: 27
<212> TYPE: DNA
<213> ORGANISM: Artificial
<220> FEATURE:
<223> OTHER INFORMATION: Artificial RNAi Sequence

<400> SEQUENCE: 14
agaccgtgtg aatcattgtc tgacaat                                          27

<210> SEQ ID NO 15
<211> LENGTH: 27
<212> TYPE: DNA
<213> ORGANISM: Artificial
<220> FEATURE:
<223> OTHER INFORMATION: Artificial RNAi Sequence

<400> SEQUENCE: 15
ggttttgtta aaggccttca tagcgaa                                          27

<210> SEQ ID NO 16
<211> LENGTH: 13481
<212> TYPE: DNA
<213> ORGANISM: Homo sapiens

<400> SEQUENCE: 16
gctgccggga cgggtccaag atggacggcc gctcaggttc tgcttttacc tgcggcccag      60
agccccattc attgccccgg tgctgagcgg cgccgcgagt cggcccgagg cctccgggga     120
ctgccgtgcc gggcgggaga ccgccatggc gaccctggaa aagctgatga aggccttcga     180
gtccctcaag tccttccagc agcagcagca gcagcagcag cagcagcagc agcagcagca     240
gcagcagcag cagcagcagc aacagccgcc accgccgccg ccgccgccgc cgcctcctca     300
gcttcctcag ccgccgccgc aggcacagcc gctgctgcct cagccgcagc cgcccccgcc     360 gccgccccg ccgccacccg cccggctgtg ggctgaggag ccgctgcacc gaccaaagaa     420
agaactttca gctaccaaga aagaccgtgt gaatcattgt ctgacaatat gtgaaaacat     480
```

```
agtggcacag tctgtcagaa attctccaga atttcagaaa cttctgggca tcgctatgga    540
acttttctg  ctgtgcagtg atgacgcaga gtcagatgtc aggatggtgg ctgacgaatg    600
cctcaacaaa gttatcaaag ctttgatgga ttctaatctt ccaaggttac agctcgagct    660
ctataaggaa attaaaaaga atggtgcccc tcggagtttg cgtgctgccc tgtggaggtt    720
tgctgagctg gctcacctgg ttcggcctca gaaatgcagg ccttacctgg tgaaccttct    780
gccgtgcctg actcgaacaa gcaagagacc cgaagaatca gtccaggaga ccttggctgc    840
agctgttccc aaaattatgg cttcttttgg caattttgca aatgacaatg aaattaaggt    900
tttgttaaag gccttcatag cgaacctgaa gtcaagctcc cccaccattc ggcggacagc    960
ggctggatca gcagtgagca tctgccagca ctcaagaagg acacaatatt tctatagttg   1020
gctactaaat gtgctcttag gcttactcgt tcctgtcgag gatgaacact ccactctgct   1080
gattcttggc gtgctgctca ccctgaggta tttggtgccc ttgctgcagc agcaggtcaa   1140
ggacacaagc ctgaaaggca gcttcggagt gacaaggaaa gaaatggaag tctctccttc   1200
tgcagagcag cttgtccagg tttatgaact gacgttacat catacacagc accaagacca   1260
caatgttgtg accggagccc tggagctgtt gcagcagctc ttcagaacgc tccacccga    1320
gcttctgcaa accctgaccg cagtcggggg cattgggcag ctcaccgctg ctaaggagga   1380
gtctggtggc cgaagccgta gtgggagtat tgtggaactt atagctggag ggggttcctc   1440
atgcagccct gtcctttcaa gaaaacaaaa aggcaaagtg ctcttaggag aagaagaagc   1500
cttggaggat gactctgaat cgagatcgga tgtcagcagc tctgccttaa cagcctcagt   1560
gaaggatgag atcagtggag agctggctgc ttcttcaggg gtttccactc cagggtcagc   1620
aggtcatgac atcatcacag aacagccacg gtcacagcac acactgcagg cggactcagt   1680
ggatctggcc agctgtgact tgacaagctc tgccactgat ggggatgagg aggatatctt   1740
gagccacagc tccagccagg tcagcgccgt cccatctgac cctgccatgg acctgaatga   1800
tgggacccag gcctcgtcgc ccatcagcga cagctcccag accaccaccg aagggcctga   1860
ttcagctgtt accccttcag acagttctga aattgtgtta gacggtaccg acaaccagta   1920
tttgggcctg cagattggac agccccagga tgaagatgag gaagccacag gtattcttcc   1980
tgatgaagcc tcggaggcct tcaggaactc ttccatggcc cttcaacagg cacatttatt   2040
gaaaaacatg agtcactgca ggcagccttc tgacagcagt gttgataaat ttgtgttgag   2100
agatgaagct actgaaccgg gtgatcaaga aaacaagcct tgccgcatca aggtgacat    2160
tggacagtcc actgatgatg actctgcacc tcttgtccat tgtgtccgcc ttttatctgc   2220
ttcgtttttg ctaacagggg gaaaaaatgt gctggttccg gacagggatg tgagggtcag   2280
cgtgaaggcc ctggccctca gctgtgtggg agcagctgtg gccctccacc cggaatcttt   2340
cttcagcaaa ctctataaag ttcctcttga caccacggaa taccctgagg aacagtatgt   2400
ctcagacatc ttgaactaca tcgatcatgg agacccacag gttcgaggag ccactgccat   2460
tctctgtggg accctcatct gctccatcct cagcaggtcc cgcttccacg tgggagattg   2520
gatgggcacc attagaaccc tcacaggaaa tacattttct ttggcggatt gcattccttt   2580
gctgcggaaa cactgaagg atgagtcttc tgttacttgc aagttagctt gtacagctgt    2640
gaggaactgt gtcatgagtc tctgcagcag cagctacagt gagttaggac tgcagctgat   2700
catcgatgtg ctgactctga ggaacagttc ctattggctg gtgaggacag agcttctgga   2760
aaccccttgca gagattgact tcaggctggt gagcttttg gaggcaaaag cagaaaactt    2820
acacagaggg gctcatcatt atacagggct tttaaaactg caagaacgag tgctcaataa   2880
```

```
tgttgtcatc catttgcttg gagatgaaga ccccagggtg cgacatgttg ccgcagcatc    2940
actaattagg cttgtcccaa agctgtttta taaatgtgac caaggacaag ctgatccagt    3000
agtggccgtg gcaagagatc aaagcagtgt ttacctgaaa cttctcatgc atgagacgca    3060
gcctccatct catttctccg tcagcacaat aaccagaata tatagaggct ataacctact    3120
accaagcata acagacgtca ctatggaaaa taacctttca agagttattg cagcagtttc    3180
tcatgaacta atcacatcaa ccaccagagc actcacattt ggatgctgtg aagctttgtg    3240 tcttcttttcc actgccttcc cagtttgcat ttggagttta ggttggcact gtggagtgcc    3300
tccactgagt gcctcagatg agtctaggaa gagctgtacc gttgggatgg ccacaatgat    3360
tctgaccctg ctctcgtcag cttggttccc attggatctc tcagcccatc aagatgcttt    3420
gattttggcc ggaaacttgc ttgcagccag tgctcccaaa tctctgagaa gttcatgggc    3480
ctctgaagaa gaagccaacc cagcagccac caagcaagag gaggtctggc cagccctggg    3540
ggaccgggcc ctggtgccca tggtggagca gctcttctct cacctgctga aggtgattaa    3600
catttgtgcc cacgtcctgg atgacgtggc tcctggaccc gcaataaagg cagccttgcc    3660
ttctctaaca acccccctt ctctaagtcc catccgacga aaggggaagg agaaagaacc    3720
aggagaacaa gcatctgtac cgttgagtcc caagaaaggc agtgaggcca gtgcagcttc    3780
tagacaatct gatacctcag gtcctgttac aacaagtaaa tcctcatcac tggggagttt    3840
ctatcatctt ccttcatacc tcaaactgca tgatgtcctg aaagctacac acgctaacta    3900
caaggtcacg ctggatcttc agaacagcac ggaaaagttt ggagggtttc tccgctcagc    3960
cttggatgtt ctttctcaga tactagagct ggccacactg caggacattg ggaagtgtgt    4020
tgaagagatc ctaggatacc tgaaatcctg ctttagtcga gaccaatga tggcaactgt    4080 ttgtgttcaa caattgttga agactctctt tggcacaaac ttggcctccc agtttgatgg    4140
cttatcttcc aaccccagca agtcacaagg ccgagcacag cgccttggct cctccagtgt    4200
gaggccaggc ttgtaccact actgcttcat ggccccgtac acccacttca cccaggccct    4260
cgctgacgcc agcctgagga acatggtgca ggcggagcag gagaacgaca cctcgggatg    4320
gtttgatgtc ctccagaaag tgtctaccca gttgaagaca aacctcacga gtgtcacaaa    4380
gaaccgtgca gataagaatg ctattcataa tcacattcgt ttgttgaac ctcttgttat    4440 aaaagcttta aaacagtaca cgactacaac atgtgtgcag ttacagaagc aggttttaga    4500
tttgctggcg cagctggttc agttacgggt taattactgt cttctggatt cagatcaggt    4560
gtttattggc tttgtattga acagtttga atacattgaa gtgggccagt tcagggaatc    4620
agaggcaatc attccaaaca tctttttctt cttggtatta ctatcttatg aacgctatca    4680
ttcaaaacag atcattggaa ttcctaaaat cattcagctc tgtgatggca tcatggccag    4740
tggaaggaag gctgtgacac atgccatacc ggctctgcag cccatagtcc acgacctctt    4800
tgtattaaga ggaacaaata aagctgatgc aggaaaagag cttgaaaccc aaaaagaggt    4860
ggtggtgtca atgttactga gactcatcca gtaccatcag gtgttggaga tgttcattct    4920
tgtcctgcag cagtgccaca aggagaatga agacaagtgg aagcgactgt ctcgacagat    4980
agctgacatc atcctcccaa tgttagccaa acagcagatg cacattgact ctcatgaagc    5040
ccttggagtg ttaaatacat tatttgagat tttggcccct tcctccctcc gtccggtaga    5100
catgctttta cggagtatgt tcgtcactcc aaacacaatg gcgtccgtga gcactgttca    5160
actgtggata tcgggaattc tggccatttt gagggtctg atttcccagt caactgaaga    5220
tattgttctt tctcgtattc aggagctctc cttctctccg tatttaatct cctgtacagt    5280
```

```
aattaatagg ttaagagatg gggacagtac ttcaacgcta gaagaacaca gtgaagggaa      5340
acaaataaag aatttgccag aagaaacatt ttcaaggttt ctattacaac tggttggtat      5400
tcttttagaa gacattgtta caaaacagct gaaggtggaa atgagtgagc agcaacatac      5460
tttctattgc caggaactag gcacactgct aatgtgtctg atccacatct tcaagtctgg      5520
aatgttccgg agaatcacag cagctgccac taggctgttc cgcagtgatg ctgtggcgg       5580 cagtttctac accctggaca gcttgaactt gcgggctcgt tccatgatca ccacccaccc      5640
ggccctggtg ctgctctggt gtcagatact gctgcttgtc aaccacaccg actaccgctg      5700
gtgggcagaa gtgcagcaga ccccgaaaag acacagtctg tccagcacaa agttacttag      5760
tccccagatg tctggagaag aggaggattc tgacttggca gccaaacttg gaatgtgcaa      5820
tagagaaata gtacgaagag gggctctcat tctcttctgt gattatgtct gtcagaacct      5880
ccatgactcc gagcacttaa cgtggctcat tgtaaatcac attcaagatc tgatcagcct      5940
ttcccacgag cctccagtac aggacttcat cagtgccgtt catcggaact ctgctgccag      6000
cggcctgttc atccaggcaa ttcagtctcg ttgtgaaaac ctttcaactc caaccatgct      6060
gaagaaaact cttcagtgct tggagggat ccatctcagc cagtcgggag ctgtgctcac       6120
gctgtatgtg gacaggcttc tgtgcacccc tttccgtgtg ctggctcgca tggtcgacat      6180
ccttgcttgt cgccgggtag aaatgcttct ggctgcaaat ttacagagca gcatggccca      6240
gttgccaatg aagaactca acagaatcca ggaataccttt cagagcagcg ggctcgctca     6300
gagacaccaa aggctctatt ccctgctgga caggtttcgt ctctccacca tgcaagactc      6360
acttagtccc tctcctccag tctcttccca cccgctggac ggggatgggc acgtgtcact      6420
ggaaacagtg agtccggaca aagactggta cgttcatctt gtcaaatccc agtgttggac      6480
caggtcagat tctgcactgc tggaaggtgc agagctggta atcggattc ctgctgaaga       6540 tatgaatgcc ttcatgatga actcggagtt caacctaagc ctgctagctc catgcttaag      6600
cctagggatg agtgaaattt ctggtggcca gaagagtgcc cttttttgaag cagcccgtga    6660 ggtgactctg gccgtgtga gcggcaccgt gcagcagctc cctgctgtcc atcatgtctt      6720
ccagcccgag ctgcctgcag agccggcggc ctactgagc aagttgaatg atctgtttgg      6780
ggatgctgca ctgtatcagt ccctgcccac tctggcccgg gccctggcac agtacctggt      6840
ggtggtctcc aaactgccca gtcatttgca ccttcctcct gagaaagaga aggacattgt      6900
gaaattcgtg gtggcaaccc ttgaggccct gtcctggcat ttgatccatg agcagatccc     6960
gctgagtctg gatctccagg cagggctgga ctgctgctgc ctggccctgc agctgcctgg      7020
cctctggagc gtggtctcct ccacagagtt tgtgacccac gcctgctccc tcatctactg      7080
tgtgcacttc atcctggagg ccgttgcagt gcagcctgga gagcagcttc ttagtccaga     7140
aagaaggaca aataccccaa aagccatcag cgaggaggag gaggaagtag atccaaacac      7200
acagaatcct aagtatatca ctgcagcctg tgagatggtg gcagaaatgg tggagtctct     7260
gcagtcggtg ttggccttgg gtcataaaag gaatagcggc gtgccggcgt ttctcacgcc      7320
attgctaagg aacatcatca tcagcctggc ccgcctgccc cttgtcaaca gctacacacg     7380
tgtgccccca ctggtgtgga agcttggatg gtcacccaaa ccgggagggg attttggcac     7440
agcattccct gagatccccg tggagttcct ccaggaaaag gaagtcttta aggagttcat     7500
ctaccgcatc aacacactag gctggaccag tcgtactcag tttgaagaaa cttgggccac      7560
cctccttggt gtcctggtga cgcagcccct cgtgatggag caggaggaga gcccaccaga      7620
agaagacaca gagaggaccc agatcaacgt cctggccgtg caggccatca cctcactggt      7680
```

```
gctcagtgca atgactgtgc ctgtggccgg caacccagct gtaagctgct tggagcagca    7740
gccccggaac aagcctctga aagctctcga caccaggttt gggaggaagc tgagcattat    7800
cagagggatt gtggagcaag agattcaagc aatggtttca agagagaga atattgccac    7860 ccatcattta tatcaggcat gggatcctgt cccttctctg tctccggcta ctacaggtgc    7920
cctcatcagc cacgagaagc tgctgctaca gatcaacccc gagcgggagc tggggagcat    7980
gagctacaaa ctcggccagg tgtccataca ctccgtgtgg ctggggaaca gcatcacacc    8040
cctgagggag gaggaatggg acgaggaaga ggaggaggag gccgacgccc ctgcaccttc    8100
gtcaccaccc acgtctccag tcaactccag gaaacaccgg gctggagttg acatccactc    8160
ctgttcgcag ttttttgcttg agttgtacag ccgctggatc ctgccgtcca gctcagccag    8220
gaggaccccg gccatcctga tcagtgaggt ggtcagatcc cttctagtgg tctcagactt    8280
gttcaccgag cgcaaccagt ttgagctgat gtatgtgacg ctgacagaac tgcgaagggt    8340
gcacccttca gaagacgaga tcctcgctca gtacctggtg cctgccacct gcaaggcagc    8400
tgccgtcctt gggatggaca aggccgtggc ggagcctgtc agccgcctgc tggagagcac    8460
gctcaggagc agccacctgc ccagcagggt tggagccctg cacggcgtcc tctatgtgct    8520
ggagtgcgac ctgctggacg acactgccaa gcagctcatc ccggtcatca gcgactatct    8580
cctctccaac ctgaaaggga tcgcccactg cgtgaacatt cacagccagc agcacgtact    8640
ggtcatgtgt gccactgcgt tttacctcat tgagaactat cctctggacg tagggccgga    8700
attttcagca tcaataatac agatgtgtgg ggtgatgctg tctggaagtg aggagtccac    8760
cccctccatc atttaccact gtgccctcag aggcctggag cgcctcctgc tctctgagca    8820
gctctcccgc ctggatgcag aatcgctggt caagctgagt gtggacagag tgaacgtgca    8880
cagcccgcac cgggccatgg cggctctggg cctgatgctc acctgcatgt acacaggaaa    8940
ggagaaagtc agtccgggta gaacttcaga ccctaatcct gcagccccg acagcgagtc    9000 agtgattgtt gctatggagc gggtatctgt tcttttttgat aggatcagga aaggcttttcc    9060 ttgtgaagcc agagtggtgg ccaggatcct gccccagttt ctagacgact tcttcccacc    9120
ccaggacatc atgaacaaag tcatcggaga gtttctgtcc aaccagcagc catacccca    9180 gttcatggcc accgtggtgt ataaggtgtt tcagactctg cacagcaccg gcagtcgtc    9240 catggtccgg gactgggtca tgctgtccct ctccaacttc acgcagaggg ccccggtcgc    9300
catggccacg tggagcctct cctgcttctt tgtcagcgcg tccaccagcc cgtgggtcgc    9360
ggcgatcctc ccacatgtca tcagcaggat gggcaagctg gagcaggtgg acgtgaacct    9420
tttctgcctg gtcgccacag acttctacag acaccagata gaggaggagc tcgaccgcag    9480
ggccttccag tctgtgcttg aggtggttgc agccccagga agcccatatc accggctgct    9540
gacttgttta cgaaatgtcc acaaggtcac cacctgctga gcgccatggt gggagagact    9600
gtgaggcggc agctggggcc ggagcctttg gaagtctgcg cccttgtgcc ctgcctccac    9660
cgagccagct tggtccctat gggcttccgc acatgccgcg ggcggccagg caacgtgcgt    9720
gtctctgcca tgtggcagaa gtgctctttg tggcagtggc caggcaggga gtgtctgcag    9780
tcctggtggg gctgagcctg aggccttcca gaaagcagga gcagctgtgc tgcacccat    9840 gtgggtgacc aggtccttttc tcctgatagt cacctgctgg ttgttgccag gttgcagctg    9900
ctcttgcatc tgggccagaa gtcctccctc ctgcaggctg gctgttggcc cctctgctgt    9960
cctgcagtag aaggtgccgt gagcaggctt tgggaacact ggcctgggtc tccctggtgg   10020
ggtgtgcatg ccacgccccg tgtctggatg cacagatgcc atggcctgtg ctgggccagt   10080
```

```
ggctgggggt gctagacacc cggcaccatt ctcccttctc tcttttcttc tcaggattta   10140
aaatttaatt atatcagtaa agagattaat tttaacgtaa ctctttctat gcccgtgtaa   10200
agtatgtgaa tcgcaaggcc tgtgctgcat gcgacagcgt ccggggtggt ggacagggcc   10260
cccggccacg ctccctctcc tgtagccact ggcatagccc tcctgagcac ccgctgacat   10320
ttccgttgta catgttcctg tttatgcatt cacaaggtga ctgggatgta gagaggcgtt   10380
agtgggcagg tggccacagc aggactgagg acaggccccc attatcctag ggtgcgctc    10440 acctgcagcc cctcctcctc gggcacagac gactgtcgtt ctccacccac cagtcaggga   10500
cagcagcctc cctgtcactc agctgagaag gccagccctc cctggctgtg agcagcctcc   10560
actgtgtcca gagacatggg cctcccactc ctgttccttg ctagccctgg ggtggcgtct   10620
gcctaggagc tggctggcag gtgttgggac ctgctgctcc atggatgcat gcctaagag    10680 tgtcactgag ctgtgttttg tctgagcctc tctcggtcaa cagcaaagct tggtgtcttg   10740
gcactgttag tgacagagcc cagcatccct tctgccccg ttccagctga catcttgcac    10800
ggtgacccct tttagtcagg agagtgcaga tctgtgctca tcggagactg ccccacggcc   10860
ctgtcagagc cgccactcct atccccagge caggtccctg gaccagcctc ctgtttgcag    10920
gcccagagga gccaagtcat taaaatggaa gtggattctg gatggccggg ctgctgctga   10980
tgtaggagct ggatttggga gctctgcttg ccgactggct gtgagacgag gcagggctc    11040 tgcttcctca gccctagagg cgagccaggc aaggttggcg actgtcatgt ggcttggttt   11100
ggtcatgccc gtcgatgttt tgggtattga atgtggtaag tggaggaaat gttgaactc    11160 tgtgcaggtg ctgccttgag accccccaagc ttccacctgt ccctctccta tgtggcagct   11220
ggggagcagc tgagatgtgg acttgtatgc tgcccacata cgtgaggggg agctgaaagg   11280
gagcccctcc tctgagcagc ctctgccagg cctgtatgag gcttttccca ccagctccca   11340
acagaggcct cccccagcca ggaccacctc gtcctcgtgg cggggcagca ggagcggtag   11400
aaaggggtcc gatgtttgag gaggccctta agggaagcta ctgaattata acacgtaaga   11460
aaatcaccat tccgtattgg ttgggggctc ctgtttctca tcctagcttt ttcctggaaa   11520
gcccgctaga aggtttggga acgaggggaa agttctcaga actgttggct gctccccacc   11580
cgcctcccgc ctcccccgca ggttatgtca gcagctctga gacagcagta tcacaggcca   11640
gatgttgttc ctggctagat gtttacattt gtaagaaata acactgtgaa tgtaaaacag   11700
agccattccc ttggaatgca tatcgctggg ctcaacatag agtttgtctt cctcttgttt   11760
acgacgtgat ctaaaccagt ccttagcaag gggctcagaa caccccgctc tggcagtagg   11820
tgtcccccac ccccaaagac ctgcctgtgt gctccggaga tgaatatgag ctcattagta   11880
aaaatgactt cacccacgca tatacataaa gtatccatgc atgtgcatat agacacatct   11940
ataattttac acacacacct ctcaagacgg agatgcatgg cctctaagag tgcccgtgtc   12000
ggttcttcct ggaagttgac tttccttaga cccgccaggt caagttagcc gcgtgacgga   12060
catccaggcg tgggacgtgg tcagggcagg gctcattcat tgcccactag gatcccactg   12120
gcgaagatgg tctccatatc agctctctgc agaagggagg aagactttat catgttccta   12180
aaaatctgtg gcaagcaccc atcgtattat ccaaatttg ttgcaaatgt gattaatttg     12240
gttgtcaagt tttgggggtg ggctgtgggg agattgcttt tgttttcctg ctggtaatat   12300
cgggaaagat tttaatgaaa ccagggtaga attgtttggc aatgcactga agcgtgtttc   12360 ttttcccaaaa tgtgcctccc ttccgctgcg ggcccagctg agtctatgta ggtgatgttt   12420
ccagctgcca agtgctcttt gttactgtcc accctcattt ctgccagcgc atgtgtcctt   12480
```

| | | | | |
|---|---|---|---|---|
| tcaagggaa | aatgtgaagc | tgaaccccct | ccagacaccc | agaatgtagc atctgagaag | 12540 |
| gccctgtgcc | ctaaaggaca | cccctcgccc | ccatcttcat | ggaggggtc atttcagagc | 12600 |
| cctcggagcc | aatgaacagc | tcctcctctt | ggagctgaga | tgagcccac gtggagctcg | 12660 |
| ggacggatag | tagacagcaa | taactcgtg | tgtggccgcc | tggcaggtgg aacttcctcc | 12720 |
| cgttgcgggg | tggagtgagg | ttagttctgt | gtgtctggtg | ggtggagtca ggcttctctt | 12780 |
| gctacctgtg | agcatccttc | ccagcagaca | tcctcatcgg | gctttgtccc tcccccgctt | 12840 |
| cctccctctg | cggggaggac | ccgggaccac | agctgctggc | cagggtagac ttggagctgt | 12900 |
| cctccagagg | ggtcacgtgt | aggagtgaga | agaaggaaga | tcttgagagc tgctgaggga | 12960 |
| ccttggagag | ctcaggatgg | ctcagacgag | gacactcgct | tgccgggcct gggcctcctg | 13020 |
| ggaaggaggg | agctgctcag | aatgccgcat | gacaactgaa | ggcaacctgg aaggttcagg | 13080 |
| ggccgctctt | cccccatgtg | cctgtcacgc | tctggtgcag | tcaaaggaac gccttcccct | 13140 |
| cagttgttt | taagagcaga | gtctcccgct | gcaatctggg | tggtaactgc cagccttgga | 13200 |
| ggatcgtggc | caacgtggac | ctgcctacgg | agggtgggct | ctgacccaag tggggcctcc | 13260 |
| ttgtccaggt | ctcactgctt | tgcaccgtgg | tcagagggac | tgtcagctga gcttgagctc | 13320 |
| ccctggagcc | agcagggctg | tgatgggcga | gtccggagc | cccacccaga cctgaatgct | 13380 |
| tctgagagca | aaggaagga | ctgacgagag | atgtatattt | aatttttta ctgctgcaaa | 13440 |
| cattgtacat | ccaaattaaa | ggaaaaaat | ggaaaccatc | a | 13481 |

<210> SEQ ID NO 17
<211> LENGTH: 5850
<212> TYPE: DNA
<213> ORGANISM: Homo sapiens

<400> SEQUENCE: 17

| | | | | |
|---|---|---|---|---|
| acaagtcttt | ccgcctcccc | agcccgcccg | ggagctgcga | gccgcgagct ggattatggt | 60 |
| ggcctgagca | gccaacgcag | ccgcaggagc | ccggagccct | tgcccctgcc cgcgccgccg | 120 |
| cccgccgggg | ggaccaggga | agccgccacc | ggcccgccat | gcccgcccct cccagccccg | 180 |
| ccgggagccc | gcgcccgctg | cccaggctgg | ccgccgccgt | gccgatgtag cgggctccgg | 240 |
| atcccagcct | ctcccctgct | cccgtgctct | gcggatctcc | cctgaccgct ctccacagcc | 300 |
| cggacccggg | ggctggccca | gggccctgca | ggccctggcg | tcctgatgcc ccaagctcc | 360 |
| ctctcctgag | aagccaccag | caccacccag | acttgggggc | aggcgccagg acggacgtg | 420 |
| ggccagtgcg | agcccagagg | gcccgaaggc | cggggcccac | catggcccaa gcctgccct | 480 |
| ggctcctgct | gtgatgggc | gcgggagtgc | tgcctgccca | cggcacccag cacggcatcc | 540 |
| ggctgcccct | cgcgcagcgg | ctgggggggcg | ccccctggg | gctgcggctg cccgggaga | 600 |
| ccgacgaaga | gcccgaggag | cccggccgga | ggggcagctt | tgtggagatg gtggacaacc | 660 |
| tgagggggcaa | gtcggggcag | ggctactacg | tggagatgac | cgtgggcagc cccccgcaga | 720 |
| cgctcaacat | cctggtggat | acaggcagca | gtaactttgc | agtgggtgct gcccccccacc | 780 |
| ccttcctgca | tcgctactac | cagaggcagc | tgtccagcac | ataccgggac ctccggaagg | 840 |
| gtgtgtatgt | gcctacacc | cagggcaagt | gggaagggga | gctgggcacc gacctggtaa | 900 |
| gcatccccca | tggccccaac | gtcactgtgc | gtgccaacat | tgctgccatc actgaatcag | 960 |
| acaagttctt | catcaacggc | tccaactggg | aaggcatcct | ggggctggcc tatgctgaga | 1020 |
| ttgccaggcc | tgacgactcc | ctggagcctt | tctttgactc | tctggtaaag cagacccacg | 1080 |
| ttcccaacct | cttctccctg | cagctttgtg | gtgctggctt | ccccctcaac cagtctgaag | 1140 |

```
tgctggcctc tgtcggaggg agcatgatca ttggaggtat cgaccactcg ctgtacacag    1200
gcagtctctg gtatacaccc atccggcggg agtggtatta tgaggtgatc attgtgcggg    1260
tggagatcaa tggacaggat ctgaaaatgg actgcaagga gtacaactat gacaagagca    1320
ttgtggacag tggcaccacc aaccttcgtt tgcccaagaa agtgtttgaa gctgcagtca    1380
aatccatcaa ggcagcctcc tccacggaga agttccctga tggtttctgg ctaggagagc    1440
agctggtgtg ctggcaagca ggcaccaccc cttggaacat tttcccagtc atctcactct    1500
acctaatggg tgaggttacc aaccagtcct tccgcatcac catccttccg cagcaatacc    1560
tgcggccagt ggaagatgtg gccacgtccc aagacgactg ttacaagttt gccatctcac    1620
agtcatccac gggcactgtt atgggagctg ttatcatgga gggcttctac gttgtctttg    1680
atcgggcccg aaaacgaatt ggctttgctg tcagcgcttg ccatgtgcac gatgagttca    1740
ggacggcagc ggtggaaggc cctttgtca ccttggacat ggaagactgt ggctacaaca    1800
ttccacagac agatgagtca accctcatga ccatagccta tgtcatggct gccatctgcg    1860
ccctcttcat gctgccactc tgcctcatgg tgtgtcagtg gcgctgcctc cgctgcctgc    1920
gccagcagca tgatgacttt gctgatgaca ctctccctgct gaagtgagga ggcccatggg    1980
cagaagatag agattcccct ggaccacacc tccgtggttc actttggtca caagtaggag    2040
acacagatgg cacctgtggc cagagcacct caggaccctc cccacccacc aaatgcctct    2100
gccttgatgg agaaggaaaa ggctggcaag gtgggttcca gggactgtac ctgtaggaaa    2160
cagaaaagag aagaaagaag cactctgctg gcgggaatac tcttggtcac ctcaaattta    2220
agtcgggaaa ttctgctgct tgaaacttca gccctgaacc tttgtccacc attcctttaa    2280
attctccaac ccaaagtatt cttcttttct tagtttcaga agtactggca tcacacgcag    2340
gttaccttgg cgtgtgtccc tgtggtaccc tggcagagaa gagaccaagc ttgtttccct    2400
gctggccaaa gtcagtagga gaggatgcac agtttgctat ttgctttaga gacagggact    2460
gtataaacaa gcctaacatt ggtgcaaaga ttgcctcttg aattaaaaaa aaaaactaga    2520
ttgactattt atacaaatgg gggcggctgg aaagaggaga aggagaggga gtacaaagac    2580
agggaatagt gggatcaaag ctaggaaagg cagaaacaca accactcacc agtcctagtt    2640
ttagacctca tctccaagat agcatcccat ctcagaagat gggtgttgtt ttcaatgttt    2700
tcttttctgt ggttgcagcc tgaccaaaag tgagatggga agggcttatc tagccaaaga    2760
gctctttttt agctctctta aatgaagtgc ccactaagaa gttccactta acacatgaat    2820
ttctgccata ttaatttcat tgtctctatc tgaaccaccc tttattctac atatgatagg    2880
cagcactgaa atatcctaac cccctaagct ccaggtgccc tgtgggagag caactggact    2940
atagcagggc tgggctctgt cttcctggtc ataggctcac tctttccccc aaatcttcct    3000
ctggagcttt gcagccaagg tgctaaaagg aataggtagg agacctcttc tatctaatcc    3060
ttaaaagcat aatgttgaac attcattcaa cagctgatgc cctataaccc ctgcctggat    3120
ttcttcctat taggctataa gaagtagcaa gatctttaca taattcagag tggtttcatt    3180
gccttcctac cctctctaat ggcccctcca tttatttgac taaagcatca cacagtggca    3240
ctagcattat accaagagta tgagaaatac agtgctttat ggctctaaca ttactgcctt    3300
cagtatcaag gctgcctgga gaaaggatgg cagcctcagg gcttccttat gtcctccacc    3360
acaagagctc cttgatgaag gtcatctttt tcccctatcc tgttcttccc ctcccgctc    3420 ctaatggtac gtgggtaccc aggctggttc ttgggctagg agtgggac caagttcatt    3480 acctccctat cagttctagc atagtaaact acggtaccag tgttagtggg aagagctggg    3540
```

```
ttttcctagt ataccactg catcctactc ctacctggtc aacccgctgc ttccaggtat    3600
gggacctgct aagtgtggaa ttacctgata agggagaggg aaatacaagg agggcctctg    3660
gtgttcctgg cctcagccag ctgcccacaa gccataaacc aataaaacaa gaatactgag    3720 tcagttttt atctgggttc tcttcattcc cactgcactt ggtgctgctt tggctgactg    3780
ggaacacccc ataactacag agtctgacag gaagactgga gactgtccac ttctagctcg    3840
gaacttactg tgtaaataaa cttttcagaac tgctaccatg aagtgaaaat gccacatttt    3900
gctttataat ttctacccat gttgggaaaa actggctttt tcccagccct ttccagggca    3960
taaaactcaa ccccttcgat agcaagtccc atcagcctat tattttttta aagaaaactt    4020
gcacttgttt ttcttttttac agttacttcc ttcctgcccc aaaattataa actctaagtg    4080
taaaaaaaag tcttaacaac agcttcttgc ttgtaaaaat atgtattata catctgtatt    4140
tttaaattct gctcctgaaa aatgactgtc ccattctcca ctcactgcat ttggggcctt    4200
tcccattggt ctgcatgtct tttatcattg caggccagtg gacagaggga gaagggagaa    4260
caggggtcgc caacacttgt gttgctttct gactgatcct gaacaagaaa gagtaacact    4320
gaggcgctcg ctcccatgca caactctcca aaacacttat cctcctgcaa gagtgggctt    4380
tccagggtct ttactgggaa gcagttaagc cccctcctca ccccttcctt ttttctttct    4440
ttactccttt ggcttcaaag gattttggaa aagaaacaat atgctttaca ctcattttca    4500
atttctaaat ttgcagggga tactgaaaaa tacggcaggt ggcctaaggc tgctgtaaag    4560
ttgaggggag aggaaatctt aagattacaa gataaaaaac gaatcccta aacaaaaga    4620 acaatagaac tggtcttcca ttttgccacc tttcctgttc atgacagcta ctaacctgga    4680
gacagtaaca tttcattaac caaagaaagt gggtcacctg acctctgaag agctgagtac    4740
tcaggccact ccaatcaccc tacaagatgc caaggaggtc ccaggaagtc cagctcctta    4800
aactgacgct agtcaataaa cctgggcaag tgaggcaaga gaaatgagga agaatccatc    4860
tgtgaggtga caggcaagga tgaaagacaa agaaggaaaa gagtatcaaa ggcagaaagg    4920
agatcattta gttgggtctg aaaggaaaag tctttgctat ccgacatgta ctgctagtac    4980
ctgtaagcat tttaggtccc agaatggaaa aaaaaatcag ctattggtaa tataataatg    5040 tccttccct ggagtcagtt ttttaaaaa gttaactctt agttttact tgtttaattc    5100 taaaagagaa gggagctgag gccattccct gtaggagtaa agataaaagg ataggaaaag    5160
attcaaagct ctaatagagt cacagctttc ccaggtataa aacctaaaat taagaagtac    5220
aataagcaga ggtggaaaat gatctagttc ctgatagcta cccacagagc aagtgattta    5280
taaatttgaa atccaaacta cttttcttaat atcactttgg tctccatttt tcccaggaca    5340
ggaaatatgt ccccccctaa ctttcttgct tcaaaaatta aaatccagca tcccaagatc    5400
attctacaag taattttgca cagacatctc ctcaccccag tgcctgtctg gagctcaccc    5460
aaggtcacca aacaacttgg ttgtgaacca actgccttaa ccttctgggg gaggggatt    5520 agctagacta ggagaccaga agtgaatggg aaagggtgag gacttcacaa tgttggcctg    5580
tcagagcttg attagaagcc aagacagtgg cagcaaagga agacttggcc caggaaaaac    5640
ctgtgggttg tgctaatttc tgtccagaaa ataggtggga cagaagcttg tggggtacat    5700
ggaggaattg ggacctggtt atgttgttat tctcggactg tgaattttgg tgatgtaaaa    5760
cagaatattc tgtaaaccta atgtctgtat aaataatgag cgttaacaca gtaaaatatt    5820
caataagaag tcaaaaaaaa aaaaaaaaaa                                    5850
```

<210> SEQ ID NO 18

<211> LENGTH: 5775
<212> TYPE: DNA
<213> ORGANISM: Homo sapiens

<400> SEQUENCE: 18

| | | | | | |
|---|---|---|---|---|---|
| acaagtctttt | ccgcctcccc | agcccgcccg | ggagctgcga | gccgcgagct | ggattatggt | 60 |
| ggcctgagca | gccaacgcag | ccgcaggagc | ccggagccct | tgcccctgcc | cgcgccgccg | 120 |
| cccgccgggg | ggaccaggga | agccgccacc | ggcccgccat | gcccgcccct | cccagccccg | 180 |
| ccgggagccc | gcgcccgctg | cccaggctgg | ccgccgccgt | gccgatgtag | cgggctccgg | 240 |
| atcccagcct | ctccctgct | cccgtgctct | gcggatctcc | cctgaccgct | ctccacagcc | 300 |
| cggacccggg | ggctggccca | gggccctgca | ggccctggcg | tcctgatgcc | cccaagctcc | 360 |
| ctctcctgag | aagccaccag | caccacccag | acttgggggc | aggcgccagg | gacggacgtg | 420 |
| ggccagtgcg | agcccagagg | gcccgaaggc | cggggcccac | catggcccaa | gccctgccct | 480 |
| ggctcctgct | gtggatgggc | gcgggagtgc | tgcctgccca | cggcacccag | cacggcatcc | 540 |
| ggctgcccct | gcgcagcggc | ctggggggcg | ccccctggg | gctgcggctg | ccccgggaga | 600 |
| ccgacgaaga | gcccgaggag | cccggccgga | ggggcagctt | tgtggagatg | gtggacaacc | 660 |
| tgagggggcaa | gtcggggcag | ggctactacg | tggagatgac | cgtgggcagc | cccccgcaga | 720 |
| cgctcaacat | cctggtggat | acaggcagca | gtaactttgc | agtgggtgct | gccccccacc | 780 |
| ccttcctgca | tcgctactac | cagaggcagc | tgtccagcac | ataccgggac | tccggaaggg | 840 |
| gtgtgtatgt | gccctacacc | cagggcaagt | gggaagggga | gctgggcacc | gacctggtaa | 900 |
| gcatccccca | tggccccaac | gtcactgtgc | gtgccaacat | tgctgccatc | actgaatcag | 960 |
| acaagttctt | catcaacggc | tccaactggg | aaggcatcct | ggggctggcc | tatgctgaga | 1020 |
| ttgccaggct | ttgtggtgct | ggcttccccc | tcaaccagtc | tgaagtgctg | gcctctgtcg | 1080 |
| gagggagcat | gatcattgga | ggtatcgacc | actcgctgta | cacaggcagt | ctctggtata | 1140 |
| cacccatccg | gcgggagtgg | tattatgagg | tgatcattgt | gcgggtggag | atcaatggac | 1200 |
| aggatctgaa | aatggactgc | aaggagtaca | actatgacaa | gagcattgtg | gacagtggca | 1260 |
| ccaccaacct | tcgtttgccc | aagaaagtgt | ttgaagctgc | agtcaaatcc | atcaaggcag | 1320 |
| cctcctccac | ggagaagttc | cctgatggtt | tctggctagg | agagcagctg | gtgtgctggc | 1380 |
| aagcaggcac | caccccttgg | aacatttcc | cagtcatctc | actctaccta | atgggtgagg | 1440 |
| ttaccaacca | gtccttccgc | atcaccatcc | ttccgcagca | atacctgcgg | ccagtggaag | 1500 |
| atgtggccac | gtcccaagac | gactgttaca | agtttgccat | ctcacagtca | tccacgggca | 1560 |
| ctgttatggg | agctgttatc | atggagggct | tctacgttgt | ctttgatcgg | gcccgaaaac | 1620 |
| gaattggctt | tgctgtcagc | gcttgccatg | tgcacgatga | gttcaggacg | gcagcggtgg | 1680 |
| aaggcccttt | tgtcaccttg | gacatggaag | actgtggcta | caacattcca | cagacagatg | 1740 |
| agtcaacccct | catgaccata | gcctatgtca | tggctgccat | ctgcgccctc | ttcatgctgc | 1800 |
| cactctgcct | catggtgtgt | cagtggcgct | gcctccgctg | cctgcgccag | cagcatgatg | 1860 |
| actttgctga | tgacatctcc | ctgctgaagt | gaggaggccc | atgggcagaa | gatagagatt | 1920 |
| cccctggacc | acacctccgt | ggttcacttt | ggtcacaagt | aggagacaca | gatggcacct | 1980 |
| gtggccagag | cacctcagga | ccctcccac | ccaccaaatg | cctctgcctt | gatggagaag | 2040 |
| gaaaaggctg | gcaaggtggg | ttccagggac | tgtacctgta | ggaaacagaa | aagagaagaa | 2100 |
| agaagcactc | tgctggcggg | aatactcttg | gtcacctcaa | atttaagtcg | ggaaattctg | 2160 |
| ctgcttgaaa | cttcagccct | gaacctttgt | ccaccattcc | tttaaattct | ccaacccaaa | 2220 |

```
gtattcttct tttcttagtt tcagaagtac tggcatcaca cgcaggttac cttggcgtgt    2280
gtccctgtgg taccctggca gagaagagac caagcttgtt tccctgctgg ccaaagtcag    2340
taggagagga tgcacagttt gctatttgct ttagagacag ggactgtata acaagccta    2400 acattggtgc aaagattgcc tcttgaatta aaaaaaaaa ctagattgac tatttataca    2460 aatggggcg gctggaaaga ggagaaggag agggagtaca agacaggga atagtgggat    2520 caaagctagg aaaggcagaa acacaaccac tcaccagtcc tagttttaga cctcatctcc    2580
aagatagcat cccatctcag aagatgggtg ttgttttcaa tgttttcttt tctgtggttg    2640
cagcctgacc aaaagtgaga tgggaagggc ttatctagcc aaaagagctct ttttttagctc    2700 tcttaaatga agtgcccact aagaagttcc acttaacaca tgaatttctg ccatattaat    2760
ttcattgtct ctatctgaac caccctttat tctacatatg ataggcagca ctgaaatatc    2820 ctaacccct aagctccagg tgccctgtgg gagagcaact ggactatagc agggctgggc    2880
tctgtcttcc tggtcatagg ctcactcttt cccccaaatc ttcctctgga gctttgcagc    2940
caaggtgcta aaaggaatag gtaggagacc tcttctatct aatccttaaa agcataatgt    3000
tgaacattca ttcaacagct gatgcccat aaccctgcc tggatttctt cctattaggc    3060
tataagaagt agcaagatct ttacataatt cagagtggtt tcattgcctt cctaccctct    3120 ctaatgccc ctccatttat ttgactaaag catcacacag tggcactagc attataccaa    3180
gagtatgaga aatacagtgc tttatggctc taacattact gccttcagta tcaaggctgc    3240
ctggagaaag gatggcagcc tcagggcttc cttatgtcct ccaccacaag agctccttga    3300
tgaaggtcat cttttttcccc tatcctgttc ttcccctccc cgctcctaat ggtacgtggg    3360
tacccaggct ggttcttggg ctaggtagtg gggaccaagt tcattcctc cctatcagtt    3420 ctagcatagt aaactacggt accagtgtta gtgggaagag ctgggttttc ctagtatacc    3480
cactgcatcc tactcctacc tggtcaaccc gctgcttcca ggtatgggac ctgctaagtg    3540
tggaattacc tgataaggga gagggaaata caaggagggc ctctggtgtt cctggcctca    3600
gccagctgcc cacaagccat aaaccaataa aacaagaata ctgagtcagt ttttatctg    3660 ggttctcttc attcccactg cacttggtgc tgctttggct gactgggaac accccataac    3720
tacagagtct gacaggaaga ctggagactg tccacttcta gctcggaact tactgtgtaa    3780
ataaactttc agaactgcta ccatgaagtg aaaatgccac attttgcttt ataatttcta    3840
cccatgttgg gaaaaactgg ctttttccca gcccttttcca gggcataaaa ctcaaccct    3900 tcgatagcaa gtcccatcag cctattattt ttttaaagaa aacttgcact tgttttttctt    3960 tttacagtta cttccttcct gccccaaaat tataaactct aagtgtaaaa aaaagtctta    4020
acaacagctt cttgcttgta aaaatatgta ttatacatct gtattttaa attctgctcc    4080 tgaaaaatga ctgtcccatt ctccactcac tgcatttggg gcctttccca ttggtctgca    4140
tgtcttttat cattgcaggc cagtggacag agggagaagg gagaacaggg gtcgccaaca    4200
cttgtgttgc tttctgactg atcctgaaca agaaagagta acactgaggc gctcgctccc    4260
atgcacaact ctccaaaaca cttatcctcc tgcaagagtg ggcttttccag ggtctttact    4320 gggaagcagt taagccccct cctcaccct tccttttttc tttctttact cctttggctt    4380
caaaggattt tggaaaagaa acaatatgct ttacactcat tttcaatttc taaatttgca    4440
ggggatactg aaaaatacgg caggtggcct aaggctgctg taaagttgag gggagaggaa    4500
atcttaagat tacaagataa aaaacgaatc ccctaaacaa aaagaacaat agaactggtc    4560 ttccatttg ccaccttcc tgttcatgac agctactaac ctggagacag taacatttca    4620
```

| | |
|---|---|
| ttaaccaaag aaagtgggtc acctgacctc tgaagagctg agtactcagg ccactccaat | 4680 |
| cacccctacaa gatgccaagg aggtcccagg aagtccagct ccttaaactg acgctagtca | 4740 |
| ataaacctgg gcaagtgagg caagagaaat gaggaagaat ccatctgtga ggtgacaggc | 4800 |
| aaggatgaaa gacaaagaag gaaaagagta tcaaaggcag aaaggagatc atttagttgg | 4860 |
| gtctgaaagg aaaagtcttt gctatccgac atgtactgct agtacctgta agcattttag | 4920 |
| gtcccagaat ggaaaaaaaa atcagctatt ggtaatataa taatgtcctt tccctggagt | 4980 |
| cagttttttt aaaagttaa ctcttagttt ttacttgttt aattctaaaa gagaagggag | 5040 |
| ctgaggccat tccctgtagg agtaaagata aaaggatagg aaaagattca aagctctaat | 5100 |
| agagtcacag ctttcccagg tataaaacct aaaattaaga agtacaataa gcagaggtgg | 5160 |
| aaaatgatct agttcctgat agctacccac agagcaagtg atttataaat ttgaaatcca | 5220 |
| aactactttc ttaatatcac tttggtctcc attttttccca ggacaggaaa tatgtcccccc | 5280 |
| cctaactttc ttgcttcaaa aattaaaatc cagcatccca agatcattct acaagtaatt | 5340 |
| ttgcacagac atctcctcac cccagtgcct gtctggagct cacccaaggt caccaaacaa | 5400 |
| cttggttgtg aaccaactgc cttaaccttc tgggggaggg ggattagcta gactaggaga | 5460 |
| ccagaagtga atgggaaagg gtgaggactt cacaatgttg gcctgtcaga gcttgattag | 5520 |
| aagccaagac agtggcagca aaggaagact tgggcccagga aaaacctgtg ggttgtgcta | 5580 |
| atttctgtcc agaaaatagg gtggacagaa gcttgtgggg tacatggagg aattgggacc | 5640 |
| tggttatgtt gttattctcg gactgtgaat tttggtgatg taaaacagaa tattctgtaa | 5700 |
| acctaatgtc tgtataaata atgagcgtta acacagtaaa atattcaata agaagtcaaa | 5760 |
| aaaaaaaaaa aaaaa | 5775 |

<210> SEQ ID NO 19
<211> LENGTH: 5718
<212> TYPE: DNA
<213> ORGANISM: Homo sapiens

<400> SEQUENCE: 19

| | |
|---|---|
| acaagtctttt ccgcctcccc agcccgcccg ggagctgcga gccgcgagct ggattatggt | 60 |
| ggcctgagca gccaacgcag ccgcaggagc ccggagccct tgcccctgcc cgcgccgccg | 120 |
| cccgccgggg ggaccaggga agccgccacc ggcccgccat gcccgcccct cccagccccg | 180 |
| ccgggagccc gcgcccgctg cccaggctgg ccgccgccgt gccgatgtag cgggctccgg | 240 |
| atcccagcct ctcccctgct cccgtgctct gcggatctcc cctgaccgct ctccacagcc | 300 |
| cggacccggg ggctggccca gggccctgca ggccctggcg tcctgatgcc cccaagctcc | 360 |
| ctctcctgag aagccaccag caccacccag acttgggggc aggcgccagg gacggacgtg | 420 |
| ggccagtgcg agcccagagg gcccgaaggc cggggcccac catggcccaa gccctgccct | 480 |
| ggctcctgct gtggatgggc gcgggagtgc tgcctgccca cggcacccag cacggcatcc | 540 |
| ggctgccccct gcgcagcggc ctgggggggcg ccccctggg gctgcggctg cccgggaga | 600 |
| ccgacgaaga gcccgaggag cccggccgga ggggcagctt tgtggagatg gtggacaacc | 660 |
| tgaggggcaa gtcggggcag ggctactacg tggagatgac cgtgggcagc ccccgcaga | 720 |
| cgctcaacat cctggtggat acaggcagca gtaactttgc agtgggtgct gccccccacc | 780 |
| ccttcctgca tcgctactac cagaggcagc tgtccagcac ataccgggac ctccggaagg | 840 |
| gtgtgtatgt gccctacacc cagggcaagt gggaagggga gctgggcacc gacctgcctg | 900 |
| acgactccct ggagcctttc tttgactctc tggtaaagca gacccacgtt cccaacctct | 960 |

```
tctccctgca gctttgtggt gctggcttcc ccctcaacca gtctgaagtg ctggcctctg   1020
tcggagggag catgatcatt ggaggtatcg accactcgct gtacacaggc agtctctggt   1080
atacacccat ccggcgggag tggtattatg aggtgatcat tgtgcgggtg agatcaatg    1140 gacaggatct gaaaatggac tgcaaggagt acaactatga caagagcatt gtggacagtg   1200
gcaccaccaa ccttcgtttg cccaagaaag tgtttgaagc tgcagtcaaa tccatcaagg   1260
cagcctcctc cacggagaag ttccctgatg gtttctggct aggagagcag ctggtgtgct   1320
ggcaagcagg caccacccct tggaacattt tcccagtcat ctcactctac ctaatgggtg   1380
aggttaccaa ccagtccttc cgcatcacca tccttccgca gcaataccctg cggccagtgg  1440 aagatgtggc cacgtcccaa gacgactgtt acaagtttgc catctcacag tcatccacgg   1500
gcactgttat gggagctgtt atcatggagg gcttctacgt tgtctttgat cgggcccgaa    1560
aacgaattgg ctttgctgtc agcgcttgcc atgtgcacga tgagttcagg acggcagcgg    1620
tggaaggccc ttttgtcacc ttggacatgg aagactgtgg ctacaacatt ccacagacag    1680
atgagtcaac cctcatgacc atagcctatg tcatggctgc catctgcgcc ctcttcatgc    1740
tgccactctg cctcatggtg tgtcagtggc gctgcctccg ctgcctgcgc agcagcatg    1800 atgactttgc tgatgacatc tccctgctga agtgaggagg cccatgggca gaagatagag   1860
attcccctgg accacacctc cgtggttcac tttggtcaca gtaggagac acagatggca    1920 cctgtggcca gagcacctca ggaccctccc cacccaccaa atgcctctgc cttgatggag   1980
aaggaaaagg ctggcaaggt gggttccagg gactgtacct gtaggaaaca gaaaagagaa   2040
gaaagaagca ctctgctggc gggaatactc ttggtcacct caaatttaag tcgggaaatt   2100
ctgctgcttg aaacttcagc cctgaacctt tgtccaccat tcctttaaat tctccaaccc   2160
aaagtattct tctttctta gtttcagaag tactggcatc acacgcaggt taccttggcg     2220
tgtgtccctg tggtaccctg gcagagaaga gaccaagctt gtttccctgc tggccaaagt    2280
cagtaggaga ggatgcacag tttgctattt gctttagaga cagggactgt ataaacaagc   2340
ctaacattgg tgcaaagatt gcctcttgaa ttaaaaaaaa aaactagatt gactatttat    2400
acaaatgggg gcggctggaa agaggagaag gagagggagt acaaagacag gaatagtgg    2460 gatcaaagct aggaaaggca gaaacacaac cactcaccag tcctagtttt agacctcatc    2520
tccaagatag catcccatct cagaagatgg gtgttgtttt caatgttttc ttttctgtgg    2580
ttgcagcctg accaaaagtg agatgggaag ggcttatcta gccaaagagc tctttttag    2640 ctctcttaaa tgaagtgccc actaagaagt tccacttaac acatgaattt ctgccatatt    2700
aatttcattg tctctatctg aaccacccct tattctacat atgataggca gcactgaaat   2760
atcctaaccc cctaagctcc agtgccctg tgggagagca actggactat agcagggctg    2820
ggctctgtct tcctggtcat aggctcactc tttcccccaa atcttcctct ggagctttgc    2880
agccaaggtc taaaaggaa taggtaggag acctcttcta tctaatcctt aaaagcataa    2940
tgttgaacat tcattcaaca gctgatgccc tataaccct gcctggattt cttcctatta    3000
ggctataaga agtagcaaga tctttacata attcagagtg gtttcattgc cttcctaccc    3060
tctctaatgg cccctccatt tatttgacta aagcatcaca cagtggcact agcattatac    3120
caagagtatg agaaatacag tgcttatgg ctctaacatt actgccttca gtatcaaggc    3180
tgcctggaga aaggatggca gcctcagggc ttccttatgt cctccaccac aagagctcct    3240
tgatgaaggt catctttttc ccctatcctg ttcttcccct cccgctcct aatggtacgt     3300 gggtacccag gctggttctt gggctaggta gtggggacca agttcattac ctccctatca    3360
```

```
gttctagcat agtaaactac ggtaccagtg ttagtgggaa gagctgggtt ttcctagtat    3420
acccactgca tcctactcct acctggtcaa cccgctgctt ccaggtatgg gacctgctaa    3480
gtgtggaatt acctgataag ggagagggaa atacaaggag ggcctctggt gttcctggcc    3540
tcagccagct gcccacaagc cataaaccaa taaaacaaga atactgagtc agtttttat    3600 ctgggttctc ttcattccca ctgcacttgg tgctgctttg gctgactggg aacacccat    3660 aactacagag tctgacagga agactggaga ctgtccactt ctagctcgga acttactgtg    3720
taaataaact ttcagaactg ctaccatgaa gtgaaaatgc cacattttgc tttataattt    3780
ctacccatgt tgggaaaaac tggcttttc ccagcccttt ccagggcata aaactcaacc    3840
ccttcgatag caagtcccat cagcctatta ttttttaaa gaaaacttgc acttgttttt    3900 cttttacag ttacttcctt cctgccccaa aattataaac tctaagtgta aaaaaagtc    3960 ttaacaacag cttcttgctt gtaaaaatat gtattataca tctgtatttt taaattctgc    4020
tcctgaaaaa tgactgtccc attctccact cactgcattt ggggccttc ccattggtct    4080 gcatgtcttt tatcattgca ggccagtgga cagagggaga agggagaaca ggggtcgcca    4140
acacttgtgt tgcttctga ctgatcctga acaagaaaga gtaacactga ggcgctcgct    4200
cccatgcaca actctccaaa acacttatcc tcctgcaaga gtgggctttc cagggtcttt    4260
actgggaagc agttaagccc cctcctcacc ccttccttt ttctttcttt actcctttgg    4320
cttcaaagga ttttggaaaa gaaacaatat gctttacact cattttcaat ttctaaattt    4380 gcagggata ctgaaaaata cggcaggtgg cctaaggctg ctgtaaagtt gaggggagag    4440
gaaatcttaa gattacaaga taaaaaacga atcccctaaa caaaaagaac aatagaactg    4500
gtcttccatt ttgccacctt tcctgttcat gacagctact aacctggaga cagtaacatt    4560
tcattaacca aagaaagtgg gtcacctgac ctctgaagag ctgagtactc aggccactcc    4620
aatcacccta caagatgcca aggaggtccc aggaagtcca gctccttaaa ctgacgctag    4680
tcaataaacc tgggcaagtg aggcaagaga aatgaggaag aatccatctg tgaggtgaca    4740
ggcaaggatg aaagacaaag aaggaaaaga gtatcaaagg cagaaaggag atcatttagt    4800
tgggtctgaa aggaaaagtc tttgctatcc gacatgtact gctagtacct gtaagcattt    4860
taggtcccag aatggaaaaa aaaatcagct attggtaata taataatgtc ctttccctgg    4920
agtcagtttt tttaaaaagt taactcttag tttttacttg tttaattcta aaagagaagg    4980
gagctgaggc cattccctgt aggagtaaag ataaaggat aggaaaagat tcaaagctct    5040
aatagagtca cagctttccc aggtataaaa cctaaaatta agaagtacaa taagcagagg    5100
tggaaaatga tctagttcct gatagctacc cacagagcaa gtgatttata aatttgaaat    5160
ccaaactact ttcttaatat cactttggtc tccatttttc ccaggacagg aaatatgtcc    5220
ccccctaact ttcttgcttc aaaaattaaa atccagcatc ccaagatcat tctacaagta    5280
attttgcaca gacatctcct cacccccagtg cctgtctgga gctcacccaa ggtcaccaaa    5340
caacttggtt gtgaaccaac tgccttaacc ttctggggga ggggattag ctagactagg    5400 agaccagaag tgaatgggaa agggtgagga cttcacaatg ttggcctgtc agagcttgat    5460
tagaagccaa gacagtggca gcaaaggaag acttggccca ggaaaaacct gtgggttgtg    5520
ctaatttctg tccagaaaat agggtggaca gaagcttgtg gggtacatgg aggaattggg    5580
acctggttat gttgttattc tcggactgtg aattttggtg atgtaaaaca gaatattctg    5640
taaacctaat gtctgtataa ataatgagcg ttaacacagt aaaatattca ataagaagtc    5700
aaaaaaaaaa aaaaaaaa                                                  5718
```

<210> SEQ ID NO 20
<211> LENGTH: 5643
<212> TYPE: DNA
<213> ORGANISM: Homo sapiens

<400> SEQUENCE: 20

```
acaagtcttt ccgcctcccc agcccgcccg ggagctgcga gccgcgagct ggattatggt      60
ggcctgagca gccaacgcag ccgcaggagc ccggagccct tgcccctgcc cgcgccgccg     120
cccgccgggg ggaccaggga agccgccacc ggcccgccat gcccgcccct cccagccccg     180
ccgggagccc gcgcccgctg cccaggctgg ccgccgccgt gccgatgtag cgggctccgg     240
atcccagcct ctcccctgct cccgtgctct gcggatctcc cctgaccgct ctccacagcc     300
cggacccggg ggctggccca gggccctgca ggccctggcg tcctgatgcc ccaagctcc      360
ctctcctgag aagccaccag caccacccag acttggggc aggcgccagg gacggacgtg      420
ggccagtgcg agcccagagg gcccgaaggc cggggcccac catggcccaa gccctgccct     480
ggctcctgct gtggatgggc gcgggagtgc tgcctgccca cggcacccag cacggcatcc     540
ggctgcccct gcgcagcggc ctgggggggcg ccccccctgg gctgcggctg ccccgggaga     600
ccgacgaaga gcccgaggag cccggccgga ggggcagctt tgtggagatg gtggacaacc     660
tgaggggcaa gtcggggcag ggctactacg tggagatgac cgtgggcagc cccccgcaga     720
cgctcaacat cctggtggat acaggcagca gtaactttgc agtgggtgct gccccccacc     780
ccttcctgca tcgctactac cagaggcagc tgtccagcac ataccgggac tccggaaggg     840
gtgtgtatgt gccctacacc cagggcaagt gggaagggga gctgggcacc gacctgcttt     900
gtggtgctgg cttcccccctc aaccagtctg aagtgctggc ctctgtcgga gggagcatga     960
tcattggagg tatcgaccac tcgctgtaca caggcagtct ctggtataca cccatccggc    1020
gggagtggta ttatgaggtg atcattgtgc gggtggagat caatgacag gatctgaaaa    1080
tggactgcaa ggagtacaac tatgacaaga gcattgtgga cagtggcacc accaaccttc    1140
gtttgcccaa gaaagtgttt gaagctgcag tcaaatccat caaggcagcc tcctccacgg    1200
agaagttccc tgatggtttc tggctaggag agcagctggt gtgctggcaa gcaggcacca    1260
cccccttggaa cattttccca gtcatctcac tctacctaat gggtgaggtt accaaccagt    1320
ccttccgcat caccatcctt ccgcagcaat acctgcggcc agtggaagat gtggccacgt    1380
cccaagacga ctgttacaag tttgccatct cacagtcatc cacgggcact gttatgggag    1440
ctgttatcat ggagggcttc tacgttgtct ttgatcgggc ccgaaaacga attggctttg    1500
ctgtcagcgc ttgccatgtg cacgatgagt tcaggacggc agcggtggaa ggccctttg     1560
tcaccttgga catggaagac tgtgctaca acattccaca gacagatgag tcaaccctca    1620
tgaccatagc ctatgtcatg gctgccatct gcgccctctt catgctgcca ctctgcctca    1680
tggtgtgtca gtggcgctgc ctccgctgcc tgcgccagca gcatgatgac tttgctgatg    1740
acatctccct gctgaagtga ggaggcccat gggcagaaga tagagattcc cctggaccac    1800
acctccgtgg ttcactttgg tcacaagtag gagacacaga tggcacctgt ggccagagca    1860
cctcaggacc ctccccaccc accaaatgcc tctgccttga tggagaagga aaaggctggc    1920
aaggtgggtt ccaggactg tacctgtagg aaacagaaaa gagaagaaag aagcactctg    1980
ctggcgggaa tactcttggt cacctcaaat ttaagtcggg aaattctgct gcttgaaact    2040
tcagccctga acctttgtcc accattcctt taaattctcc aacccaaagt attcttcttt    2100
tcttagtttc agaagtactg gcatcacacg caggttacct tggcgtgtgt ccctgtggta    2160
```

```
ccctggcaga gaagagacca agcttgtttc cctgctggcc aaagtcagta ggagaggatg    2220
cacagtttgc tatttgcttt agagacaggg actgtataaa caagcctaac attggtgcaa    2280
agattgcctc ttgaattaaa aaaaaaaact agattgacta tttatacaaa tgggggcggc    2340
tggaaagagg agaaggagag ggagtacaaa gacaggaat agtgggatca aagctaggaa     2400
aggcagaaac acaaccactc accagtccta gttttagacc tcatctccaa gatagcatcc    2460
catctcagaa gatgggtgtt gttttcaatg ttttcttttc tgtggttgca gcctgaccaa    2520
aagtgagatg ggaagggctt atctagccaa agagctcttt tttagctctc ttaaatgaag    2580
tgcccactaa gaagttccac ttaacacatg aatttctgcc atattaattt cattgtctct    2640
atctgaacca cccttattc tacatatgat aggcagcact gaaatatcct aaccccctaa     2700
gctccaggtg ccctgtggga gagcaactgg actatagcag ggctgggctc tgtcttcctg    2760
gtcataggct cactctttcc cccaaatctt cctctggagc tttgcagcca aggtgctaaa    2820
aggaataggt aggagacctc ttctatctaa tccttaaaag cataatgttg aacattcatt    2880
caacagctga tgccctataa ccctgcctg gatttcttcc tattaggcta taagaagtag     2940
caagatcttt acataattca gagtggtttc attgccttcc taccctctct aatggccccct   3000 ccatttattt gactaaagca tcacacagtg gcactagcat tataccaaga gtatgagaaa    3060
tacagtgctt tatggctcta acattactgc cttcagtatc aaggctgcct ggagaaagga    3120
tggcagcctc agggcttcct tatgtcctcc accacaagag ctccttgatg aaggtcatct    3180
ttttccccta tcctgttctt cccctccccg ctcctaatgg tacgtgggta cccaggctgg    3240
ttcttgggct aggtagtggg gaccaagttc attacctccc tatcagttct agcatagtaa    3300
actacggtac cagtgttagt gggaagagct gggttttcct agtataccca ctgcatccta    3360
ctcctacctg gtcaacccgc tgcttccagg tatgggacct gctaagtgtg gaattacctg    3420
ataagggaga gggaaataca aggagggcct ctggtgttcc tggcctcagc cagctgccca    3480
caagccataa accaataaaa caagaatact gagtcagttt tttatctggg ttctcttcat    3540
tcccactgca cttggtgctg cctttggctga ctgggaacac cccataacta cagagtctga   3600
caggaagact ggagactgtc cacttctagc tcggaactta ctgtgtaaat aaactttcag    3660
aactgctacc atgaagtgaa aatgccacat tttgctttat aatttctacc catgttggga    3720
aaaactggct ttttcccagc cctttccagg gcataaaact caacccccttc gatagcaagt   3780 cccatcagcc tattattttt ttaaagaaaa cttgcacttg ttttctttt tacagttact     3840 tccttcctgc cccaaaatta taaactctaa gtgtaaaaaa aagtcttaac aacagcttct    3900
tgcttgtaaa aatatgtatt atacatctgt attttttaaat tctgctcctg aaaaatgact   3960
gtcccattct ccactcactg catttggggc ctttcccatt ggtctgcatg tcttttatca    4020
ttgcaggcca gtggacagag ggagaaggga gaacaggggt cgccaacact tgtgttgctt    4080
tctgactgat cctgaacaag aaagagtaac actgaggcgc tcgctcccat gcacaactct    4140
ccaaaacact tatcctcctg caagagtggg ctttccaggg tctttactgg gaagcagtta    4200
agccccctcc tcacccttc cttttttctt tctttactcc tttggcttca aaggattttg     4260
gaaaagaaac aatatgcttt acactcattt tcaatttcta aatttgcagg ggatactgaa    4320
aaatacggca ggtggcctaa ggctgctgta aagttgaggg gagaggaaat cttaagatta    4380
caagataaaa aacgaatccc ctaaacaaaa agaacaatag aactggtctt ccattttgcc    4440
acctttcctg ttcatgacag ctactaacct ggagacagta acatttcatt aaccaaagaa    4500
agtgggtcac ctgacctctg aagagctgag tactcaggcc actccaatca ccctacaaga    4560
```

```
tgccaaggag gtcccaggaa gtccagctcc ttaaactgac gctagtcaat aaacctgggc    4620
aagtgaggca agagaaatga ggaagaatcc atctgtgagg tgacaggcaa ggatgaaaga    4680
caaagaagga aaagagtatc aaaggcagaa aggagatcat ttagtttggt ctgaaaggaa    4740
aagtctttgc tatccgacat gtactgctag tacctgtaag catttaggt cccagaatgg     4800 aaaaaaaaat cagctattgg taatataata atgtcctttc cctggagtca gttttttaa     4860 aaagttaact cttagttttt acttgtttaa ttctaaaaga aagggagct gaggccattc     4920 cctgtaggag taaagataaa aggataggaa aagattcaaa gctctaatag agtcacagct    4980
ttcccaggta taaaacctaa aattaagaag tacaataagc agaggtggaa aatgatctag    5040
ttcctgatag ctacccacag agcaagtgat ttataaattt gaaatccaaa ctactttctt    5100
aatatcactt tggtctccat ttttcccagg acaggaaata tgtccccccc taactttctt    5160
gcttcaaaaa ttaaaatcca gcatcccaag atcattctac aagtaatttt gcacagacat    5220
ctcctcaccc cagtgcctgt ctggagctca cccaaggtca ccaaacaact tggttgtgaa    5280
ccaactgcct taaccttctg ggggaggggg attagctaga ctaggagacc agaagtgaat    5340
gggaaagggt gaggacttca caatgttggc ctgtcagagc ttgattagaa gccaagacag    5400
tggcagcaaa ggaagacttg gcccaggaaa aacctgtggg ttgtgctaat ttctgtccag    5460 aaaataggt ggacagaagc ttgtggggta catggaggaa ttgggacctg gttatgttgt     5520
tattctcgga ctgtgaattt tggtgatgta aaacagaata ttctgtaaac ctaatgtctg    5580
tataaataat gagcgttaac acagtaaaat attcaataag aagtcaaaaa aaaaaaaaa    5640 aaa                                                                  5643

<210> SEQ ID NO 21
<211> LENGTH: 1543
<212> TYPE: DNA
<213> ORGANISM: Homo sapiens

<400> SEQUENCE: 21
ggagtggcca ttcgacgaca gtgtggtgta aaggaattca ttagccatgg atgtattcat      60
gaaaggactt tcaaaggcca aggagggagt tgtggctgct gctgagaaaa ccaaacaggg     120
tgtggcagaa gcagcaggaa agacaaaaga gggtgttctc tatgtaggct ccaaaaccaa     180
ggagggagtg gtgcatggtg tggcaacagt ggctgagaag accaaagagc aagtgacaaa     240
tgttggagga gcagtggtga cgggtgtgac agcagtagcc agaagacag tggagggagc      300 agggagcatt gcagcagcca ctggctttgt caaaaaggac cagttgggca agaatgaaga     360
aggagcccca caggaaggaa ttctggaaga tatgcctgtg atcctgaca atgaggctta      420 tgaaatgcct tctgaggaag ggtatcaaga ctacgaacct gaagcctaag aaatatcttt     480
gctcccagtt tcttgagatc tgctgacaga tgttccatcc tgtacaagtg ctcagttcca     540
atgtgcccag tcatgacatt tctcaaagtt tttacagtgt atctcgaagt cttccatcag     600
cagtgattga agtatctgta cctgccccca ctcagcattt cggtgcttcc ctttcactga     660
agtgaataca tggtagcagg gtctttgtgt gctgtggatt ttgtggcttc aatctacgat     720
gttaaaacaa attaaaaaca cctaagtgac taccacttat ttctaaatcc tcactatttt     780
tttgttgctg ttgttcagaa gttgttagtg atttgctatc atatattata agattttag      840 gtgtctttta atgatactgt ctaagaataa tgacgtattg tgaaatttgt taatatatat     900
aatacttaaa aatatgtgag catgaaacta tgcacctata aatactaaat atgaaatttt     960
accattttgc gatgtgtttt attcacttgt gtttgtatat aaatggtgag aattaaaata    1020
```

-continued

```
aaacgttatc tcattgcaaa atatttttat ttttatccca tctcacttta ataataaaaa    1080
tcatgcttat aagcaacatg aattaagaac tgacacaaag gacaaaaata taaagttatt    1140
aatagccatt tgaagaagga ggaatttttag aagaggtaga gaaaatggaa cattaaccct    1200
acactcggaa ttccctgaag caacactgcc agaagtgtgt tttggtatgc actggttcct    1260
taagtggctg tgattaatta ttgaaagtgg ggtgttgaag accccaacta ctattgtaga    1320
gtggtctatt tctcccttca atcctgtcaa tgtttgcttt atgtattttg gggaactgtt    1380
gtttgatgtg tatgtgttta taattgttat acatttttaa ttgagccttt tattaacata    1440
tattgttatt tttgtctcga aataattttt tagttaaaat ctattttgtc tgatattggt    1500
gtgaatgctg tacctttctg acaataaata atattcgacc atg                     1543
```

<210> SEQ ID NO 22
<211> LENGTH: 1096
<212> TYPE: DNA
<213> ORGANISM: Homo sapiens

<400> SEQUENCE: 22

```
gaattcatta gccatggatg tattcatgaa aggactttca aaggccaagg agggagttgt      60
ggctgctgct gagaaaaacca aacagggtgt ggcagaagca gcaggaaaga caaaagaggg    120
tgttctctat gtaggctcca aaaccaagga gggagtggtg catggtgtgg caacagtggc    180
tgagaagacc aaagagcaag tgacaaatgt tggaggagca gtggtgacgg tgtgacagc     240 agtagcccag aagacagtgg agggagcagg agcattgca gcagccactg gctttgtcaa    300
aaaggaccag ttgggcaagg aagggtatca agactacgaa cctgaagcct aagaaatatc    360
tttgctccca gtttcttgag atctgctgac agatgttcca tcctgtacaa gtgctcagtt    420
ccaatgtgcc cagtcatgac atttctcaaa gttttttacag tgtatctcga agtcttccat    480
cagcagtgat tgaagtatct gtacctgccc ccactcagca tttcggtgct tccctttcac    540
tgaagtgaat acatggtagc agggtctttg tgtgctgtgg attttgtggc ttcaatctac    600
gatgttaaaa caaattaaaa acacctaagt gactaccact tatttctaaa tcctcactat    660 tttttgttg ctgttgttca gaagttgtta gtgatttgct atcatatatt ataagatttt    720
taggtgtctt ttaatgatac tgtctaagaa taatgacgta ttgtgaaatt tgttaatata    780
tataatactt aaaaatatgt gagcatgaaa ctatgcacct ataaatacta aatatgaaat    840
tttaccattt tgcgatgtgt tttattcact tgtgtttgta tataaatggt gagaattaaa    900
ataaaacgtt atctcattgc aaaaatattt tattttattc ccatctcact ttaataataa    960
aaatcatgct tataagcaac atgaattaag aactgacaca aaggacaaaa atataaagtt    1020
attaatagcc atttgaagaa ggaggaattt tagaagaggt agagaaaatg gaacattaac    1080
cctacactcg gaattc                                                    1096
```

<210> SEQ ID NO 23
<211> LENGTH: 981
<212> TYPE: DNA
<213> ORGANISM: Homo sapiens

<400> SEQUENCE: 23

```
gtttggggcc agagtgggcg aggcgcggag gtctggccta taaagtagtc gcggagacgg      60
ggtgctggtt tgcgtcgtag tctcctgcag cgtctggggt ttccgttgca gtcctcggaa    120
ccaggacctc ggcgtggcct agcgagttat ggcgacgaag gccgtgtgcg tgctgaaggg    180
cgacggccca gtgcagggca tcatcaattt cgagcagaag gaaagtaatg gaccagtgaa    240
```

-continued

| | |
|---|---|
| ggtgtgggga agcattaaag gactgactga aggcctgcat ggattccatg ttcatgagtt | 300 |
| tggagataat acagcaggct gtaccagtgc aggtcctcac tttaatcctc tatccagaaa | 360 |
| acacggtggg ccaaaggatg aagagaggca tgttggagac ttgggcaatg tgactgctga | 420 |
| caaagatggt gtggccgatg tgtctattga agattctgtg atctcactct caggagacca | 480 |
| ttgcatcatt ggccgcacac tggtggtcca tgaaaaagca gatgacttgg gcaaaggtgg | 540 |
| aaatgaagaa agtacaaaga caggaaacgc tggaagtcgt ttggcttgtg gtgtaattgg | 600 |
| gatcgcccaa taaacattcc cttggatgta gtctgaggcc cttaactca tctgttatcc | 660 |
| tgctagctgt agaaatgtat cctgataaac attaaacact gtaatcttaa aagtgtaatt | 720 |
| gtgtgacttt ttcagagttg ctttaaagta cctgtagtga gaaactgatt tatgatcact | 780 |
| tggaagattt gtatagtttt ataaaaactca gttaaaatgt ctgtttcaat gacctgtatt | 840 |
| ttgccagact taaatcacag atgggtatta aacttgtcag aatttctttg tcattcaagc | 900 |
| ctgtgaataa aaaccctgta tggcacttat tatgaggcta ttaaaagaat ccaaattcaa | 960 |
| actaaaaaaa aaaaaaaaa a | 981 |

<210> SEQ ID NO 24
<211> LENGTH: 4247
<212> TYPE: DNA
<213> ORGANISM: Homo sapiens

<400> SEQUENCE: 24

| | |
|---|---|
| gttccccaac tgctgtttta ttgtgctatt catgcctaga catcacatag ctagaaaggc | 60 |
| ccatcagacc cctcaggcca ctgctgttcc tgtcacacat tcctgcaaag gaccatgttg | 120 |
| ctaacttgaa aaaaattact attaattaca cttgcagttg ttgcttagta acatttatga | 180 |
| ttttgtgttt ctcgtgacag catgagcaga gatcattaaa aattaaactt acaaagctgc | 240 |
| taaagtggga agaaggagaa cttgaagcca caattttgc acttgcttag aagccatcta | 300 |
| atctcaggtt tatatgctag atcttggggg aaacactgca tgtctctggt ttatattaaa | 360 |
| ccacatacag cacactactg acactgattt gtgtctggtg cagctggagt ttatcaccaa | 420 |
| gacataaaaa aaccttgacc ctgcagaatg gcctggaatt acaatcagat gggccacatg | 480 |
| gcatcccggt gaaagaaagc cctaaccagt tttctgtctt gtttctgctt tctccctaca | 540 |
| gttccaccag gtgagaagag tgatgaccat ccttttcctt actatggtta tttcatactt | 600 |
| tggttgcatg aaggctgccc ccatgaaaga agcaaacatc cgaggacaag gtggcttggc | 660 |
| ctacccaggt gtgcggaccc atgggactct ggagagcgtg aatgggccca aggcaggttc | 720 |
| aagaggcttg acatcattgg ctgacacttt cgaacacgtg atagaagagc tgttggatga | 780 |
| ggaccagaaa gttcggccca tgaagaaaa caataaggac gcagacttgt acacgtccag | 840 |
| ggtgatgctc agtagtcaag tgcctttgga gcctcctctt ctctttctgc tggaggaata | 900 |
| caaaaattac ctagatgctg caaacatgtc catgagggtc cggcgccact ctgaccctgc | 960 |
| ccgccgaggg gagctgagcg tgtgtgacag tattagtgag tgggtaacgg cggcagacaa | 1020 |
| aaagactgca gtggacatgt cgggcgggac ggtcacagtc cttgaaaagg tccctgtatc | 1080 |
| aaaaggccaa ctgaagcaat acttctacga gaccaagtgc aatcccatgg gttacacaaa | 1140 |
| agaaggctgc aggggcatag acaaaaggca ttggaactcc cagtgccgaa ctacccagtc | 1200 |
| gtacgtgcgg gcccttacca tggatagcaa aaagagaatt ggctggcgat tcataaggat | 1260 |
| agacacttct tgtgtatgta cattgaccat taaaagggga agatagtgga tttatgttgt | 1320 |
| atagattaga ttatattgag acaaaaatta tctatttgta tatatacata acagggtaaa | 1380 |

```
ttattcagtt aagaaaaaaa taattttatg aactgcatgt ataaatgaag tttatacagt   1440
acagtggttc tacaatctat ttattggaca tgtccatgac cagaagggaa acagtcattt   1500
gcgcacaact taaaaagtct gcattacatt ccttgataat gttgtggttt gttgccgttg   1560
ccaagaactg aaaacataaa aagttaaaaa aataataaaa ttgcatgctg ctttaattgt   1620
gaattgataa taaactgtcc tctttcagaa aacagaaaaa aaacacacac acacacaaca   1680
aaaatttgaa ccaaaacatt ccgtttacat tttagacagt aagtatcttc gttcttgtta   1740
gtactatatc tgttttactg cttttaactt ctgatagcgt tggaattaaa acaatgtcaa   1800
ggtgctgttg tcattgcttt actggcttag gggatggggg atggggggta tattttgtt    1860 tgttttgtgt tttttttttcg tttgtttgtt ttgttttttta gttcccacag ggagtagaga   1920
tggggaaaga attcctacaa tatatattct ggctgataaa agatacattt gtatgttgtg   1980
aagatgtttg caatatcgat cagatgacta gaaagtgaat aaaaattaag gcaactgaac   2040
aaaaaaatgc tcacactcca catcccgtga tgcacctccc aggccccgct cattctttgg   2100
gcgttggtca gagtaagctg cttttgacgg aaggacctat gtttgctcag aacacattct   2160
ttccccccct cccctctgg tctcctcttt gttttgtttt aaggaagaaa aatcagttgc    2220
gcgttctgaa atattttacc actgctgtga acaagtgaac acattgtgtc acatcatgac   2280
actcgtataa gcatggagaa cagtgatttt tttttagaac agaaaacaac aaaaaataac   2340
cccaaaatga agattatttt ttatgaggag tgaacatttg ggtaaatcat ggctaagctt   2400
aaaaaaaact catggtgagg cttaacaatg tcttgtaagc aaaagtaga gccctgtatc    2460 aacccagaaa cacctagatc agaacaggaa tccacattgc cagtgacatg agactgaaca   2520
gccaaatgga ggctatgtgg agttggcatt gcatttaccg gcagtgcggg aggaatttct   2580
gagtggccat cccaaggtct aggtggaggt ggggcatggt atttgagaca ttccaaaacg   2640
aaggcctctg aaggacccctt cagaggtggc tctggaatga catgtgtcaa gctgcttgga   2700
cctcgtgctt taagtgccta cattatctaa ctgtgctcaa gaggttctcg actggaggac   2760
cacactcaag ccgacttatg cccaccatcc cacctctgga taattttgca taaaattgga   2820
ttagcctgga gcaggttggg agccaaatgt ggcatttgtg atcatgagat tgatgcaatg   2880
agatagaaga tgtttgctac ctgaacactt attgctttga aactagactt gaggaaacca   2940
gggtttatct tttgagaact tttggtaagg gaaaagggaa caggaaaaga accccaaac    3000 tcaggccgaa tgatcaaggg gacccatagg aaatcttgtc cagagacaag acttcgggaa   3060
ggtgtctgga cattcagaac accaagactt gaaggtgcct tgctcaatgg aagaggccag   3120
gacagagctg acaaaatttt gctccccagt gaaggccaca gcaaccttct gcccatcctg   3180
tctgttcatg gagagggtcc ctgcctcacc tctgccattt tgggttagga gaagtcaagt   3240
tgggagcctg aaatagtggt tcttggaaaa atggatcccc agtgaaaact agagctctaa   3300
gcccattcag cccatttcac acctgaaaat gttagtgatc accacttgga ccagcatcct   3360
taagtatcag aaagccccaa gcaattgctg catcttagta gggtgaggga taagcaaaag   3420
aggatgttca ccataaccca ggaatgaaga taccatcagc aaagaatttc aatttgttca   3480
gtctttcatt tagagctagt cttttcacagt accatctgaa tacctctttg aaagaaggaa   3540
gactttacgt agtgtagatt tgttttgtgt tgtttgaaaa tattatctttt gtaattattt   3600 ttaatatgta aggaatgctt ggaatatctg ctatatgtca actttatgca gcttcctttt   3660
gagggacaaa tttaaaacaa acaaccccccc atcacaaact taaaggattg caagggccag   3720
atctgttaag tggtttcata ggagacacat ccagcaattg tgtggtcagt ggctcttta    3780
```

| cccaataaga tacatcacag tcacatgctt gatggtttat gttgacctaa gatttatttt | 3840 |
| gttaaaatct ctctctgttg tgttcgttct tgttctgttt tgttttgttt tttaaagtct | 3900 |
| tgctgtggtc tctttgtggc agaagtgttt catgcatggc agcaggcctg ttgctttttt | 3960 |
| atggcgattc ccattgaaaa tgtaagtaaa tgtctgtggc cttgttctct ctatggtaaa | 4020 |
| gatattattc accatgtaaa acaaaaaaca atatttattg tattttagta tatttatata | 4080 |
| attatgttat tgaaaaaaat tggcattaaa acttaaccgc atcagaacct attgtaaata | 4140 |
| caagttctat ttaagtgtac taattaacat ataatatatg ttttaaatat agaattttta | 4200 |
| atgttttaa atatatttc aaagtacata aaaaaaaaaa aaaaaa | 4247 |

<210> SEQ ID NO 25
<211> LENGTH: 4084
<212> TYPE: DNA
<213> ORGANISM: Homo sapiens

<400> SEQUENCE: 25

| gtgtgtaatc cgggcgatag gagtccattc agcaccttgg acagagccaa cggatttgtc | 60 |
| cgaggtggcg gtaccccag gtagtcttct tggccccgct gtaaagccaa ccctgtgtcg | 120 |
| cccttaaaaa gcgtcttttc tgaggttcgg ctcacactga gatcggggct ggagagagag | 180 |
| tcagattttg gagcggagcg tttggaaagc gagcccagt ttggtcccct cattgagctc | 240 |
| gctgaagttg gcttcctagc ggtgtaggct ggaatagact cttggcaagc tccgggttgg | 300 |
| tatactgggt taactttggg aaatgcaagt gtttatctcc aggatctagc caccggggtg | 360 |
| gtgtaagccg caaagaagtt ccaccaggtg agaagagtga tgaccatcct tttccttact | 420 |
| atggttattt catactttgg ttgcatgaag gctgccccca tgaaagaagc aaacatccga | 480 |
| ggacaaggtg gcttggccta cccaggtgtg cggacccatg ggactctgga gagcgtgaat | 540 |
| gggcccaagg caggttcaag aggcttgaca tcattggctg acactttcga cacgtgata | 600 |
| gaagagctgt tggatgagga ccagaaagtt cggcccaatg aagaaaacaa taaggacgca | 660 |
| gacttgtaca cgtccagggt gatgctcagt agtcaagtgc ctttggagcc tcctcttctc | 720 |
| tttctgctgg aggaatacaa aaattaccta gatgctgcaa acatgtccat gagggtccgg | 780 |
| cgccactctg accctgcccg ccgaggggag ctgagcgtgt gtgacagtat tagtgagtgg | 840 |
| gtaacggcgg cagacaaaaa gactgcagtg gacatgtcgg gcgggacggt cacagtcctt | 900 |
| gaaaaggtcc ctgtatcaaa aggccaactg aagcaatact tctacgagac caagtgcaat | 960 |
| cccatgggtt acacaaaaga aggctgcagg ggcatagaca aaaggcattg gaactcccag | 1020 |
| tgccgaacta cccagtcgta cgtgcgggcc cttaccatgg atagcaaaaa gagaattggc | 1080 |
| tggcgattca taaggataga cacttcttgt gtatgtacat tgaccattaa aaggggaaga | 1140 |
| tagtggattt atgttgtata gattagatta tattgagaca aaaattatct atttgtatat | 1200 |
| atacataaca gggtaaatta ttcagttaag aaaaaaataa ttttatgaac tgcatgtata | 1260 |
| aatgaagttt atacagtaca gtggttctac aatctattta ttggacatgt ccatgaccag | 1320 |
| aagggaaaca gtcatttgcg cacaacttaa aaagtctgca ttcattcct tgataatgtt | 1380 |
| gtggtttgtt gccgttgcca agaactgaaa acataaaaag ttaaaaaaaa taataaattg | 1440 |
| catgctgctt taattgtgaa ttgataataa actgtcctct ttcagaaaac agaaaaaaaa | 1500 |
| cacacacaca cacaacaaaa atttgaacca aaacattccg tttacatttt agacagtaag | 1560 |
| tatcttcgtt cttgttagta ctatatctgt tttactgctt ttaacttctg atagcgttgg | 1620 |
| aattaaaaca atgtcaaggt gctgttgtca ttgctttact ggcttagggg atggggatg | 1680 |

```
gggggtatat ttttgtttgt tttgtgtttt tttttcgttt gtttgttttg ttttttagtt        1740
cccacaggga gtagagatgg ggaaagaatt cctacaatat atattctggc tgataaaga         1800 tacatttgta tgttgtgaag atgtttgcaa tatcgatcag atgactagaa agtgaataaa        1860
aattaaggca actgaacaaa aaaatgctca cactccacat cccgtgatgc acctcccagg        1920
ccccgctcat tctttgggcg ttggtcagag taagctgctt ttgacggaag gacctatgtt        1980
tgctcagaac acattctttc ccccctccc cctctggtct cctctttgtt ttgttttaag         2040
gaagaaaaat cagttgcgcg ttctgaaata ttttaccact gctgtgaaca agtgaacaca        2100
ttgtgtcaca tcatgacact cgtataagca tggagaacag tgatttttt ttagaacaga        2160 aaacaacaaa aataaccccc aaaatgaaga ttattttta tgaggagtga acatttgggt        2220
aaatcatggc taagcttaaa aaaaactcat ggtgaggctt aacaatgtct tgtaagcaaa        2280
aggtagagcc ctgtatcaac ccagaaacac ctagatcaga acaggaatcc acattgccag        2340
tgacatgaga ctgaacagcc aaatggaggc tatgtggagt tggcattgca tttaccggca        2400
gtgcgggagg aatttctgag tggccatccc aaggtctagg tggaggtggg gcatggtatt        2460
tgagacattc caaaacgaag gcctctgaag gacccttcag aggtggctct ggaatgacat        2520
gtgtcaagct gcttggacct cgtgctttaa gtgcctacat tatctaactg tgctcaagag        2580
gttctcgact ggaggaccac actcaagccg acttatgccc accatcccac ctctggataa        2640
ttttgcataa aattggatta gcctggagca ggttgggagc caaatgtggc atttgtgatc        2700
atgagattga tgcaatgaga tagaagatgt ttgctacctg aacacttatt gctttgaaac        2760
tagacttgag gaaaccaggg tttatctttt gagaacttt ggtaagggaa aagggaacag         2820
gaaaagaaac cccaaaactca ggccgaatga tcaaggggac ccataggaaa tcttgtccag       2880
agacaagact tcgggaaggt gtctggacat tcagaacacc aagacttgaa ggtgccttgc        2940
tcaatggaag aggccaggac agagctgaca aaattttgct ccccagtgaa ggccacagca        3000
accttctgcc catcctgtct gttcatggag agggtccctg cctcacctct gccattttgg        3060
gttaggagaa gtcaagttgg gagcctgaaa tagtggttct tggaaaaatg gatccccagt        3120
gaaaactaga gctctaagcc cattcagccc atttcacacc tgaaaatgtt agtgatcacc        3180
acttggacca gcatccttaa gtatcagaaa gccccaagca attgctgcat cttagtaggg        3240
tgagggataa gcaaaagagg atgttcacca taacccagga atgaagatac catcagcaaa        3300
gaatttcaat ttgttcagtc tttcatttag agctagtctt tcacagtacc atctgaatac        3360
ctctttgaaa gaaggaagac tttacgtagt gtagatttgt tttgtgttgt ttgaaaatat        3420
tatctttgta attatttta atatgtaagg aatgcttgga atatctgcta tatgtcaact        3480
ttatgcagct tccttttgag ggacaaattt aaaacaaaca accccccatc acaaacttaa        3540
aggattgcaa gggccagatc tgttaagtgg tttcatagga gacacatcca gcaattgtgt        3600
ggtcagtggc tcttttaccc aataagatac atcacagtca catgcttgat ggtttatgtt        3660
gacctaagat ttattttgtt aaaatctctc tctgttgtgt tcgttcttgt tctgtttgt        3720 tttgtttttt aaagtcttgc tgtggtctct ttgtggcaga agtgtttcat gcatggcagc        3780
aggcctgttg ctttttatg gcgattccca ttgaaaatgt aagtaaatgt ctgtggcctt        3840
gttctctcta tggtaaagat attattcacc atgtaaaaca aaaaacaata tttattgtat        3900
tttagtatat ttatataatt atgttattga aaaaaattgg cattaaaact taaccgcatc        3960
agaacctatt gtaaatacaa gttctatta agtgtactaa ttaacatata atatgtttt         4020 taaatataga attttaatg ttttaaaata tattttcaaa gtacataaaa aaaaaaaaaa        4080
```

| aaaa | 4084 |

<210> SEQ ID NO 26
<211> LENGTH: 4044
<212> TYPE: DNA
<213> ORGANISM: Homo sapiens

<400> SEQUENCE: 26

| ggcaatcatt ggtaacctcg ctcattcatt agaatcacgt aagaactcaa aaggaaacgt | 60 |
| gtctctcgga gtgagggcgt ttgcgtaaat ctataggttt ttcgacatcg atgccagttg | 120 |
| ctttgtcttc tgtagtcgcc aaggtggttg agagtttaag cttgcggata ttgcaaaggg | 180 |
| ttattagatt cataagtcac accaagtggt gggcgatcca ctgagcaaag ccgaacttct | 240 |
| cacatgatga cttcaaacaa gacacattac cttccagcat ctgttgggga gacgagattt | 300 |
| taagacactt gagtctccag gacagcaaag gcacaatgtt ccaccaggtg agaagagtga | 360 |
| tgaccatcct tttccttact atggttattt catactttgg ttgcatgaag ctgcccccca | 420 |
| tgaaagaagc aaacatccga ggacaaggtg gcttggccta cccaggtgtg cggacccatg | 480 |
| ggactctgga gagcgtgaat gggcccaagg caggttcaag aggcttgaca tcattggctg | 540 |
| acactttcga acacgtgata aagagctgt tggatgagga ccagaaagtt cggcccaatg | 600 |
| aagaaaacaa taaggacgca gacttgtaca cgtccaggt gatgctcagt agtcaagtgc | 660 |
| ctttggagcc tcctcttctc tttctgctgg aggaatacaa aaattaccta gatgctgcaa | 720 |
| acatgtccat gagggtccgg cgccactctg accctgcccg ccgaggggag ctgagcgtgt | 780 |
| gtgacagtat tagtgagtgg gtaacggcgg cagacaaaaa gactgcagtg gacatgtcgg | 840 |
| gcgggacggt cacagtcctt gaaaaggtcc ctgtatcaaa aggccaactg aagcaatact | 900 |
| tctacgagac caagtgcaat cccatggggtt acacaaaaga aggctgcagg ggcatagaca | 960 |
| aaaggcattg gaactcccag tgccgaacta cccagtcgta cgtgcgggcc cttaccatgg | 1020 |
| atagcaaaaa gagaattggc tggcgattca taaggataga cacttcttgt gtatgtacat | 1080 |
| tgaccattaa aaggggaaga tagtggattt atgttgtata gattagatta tattgagaca | 1140 |
| aaaattatct atttgtatat atacataaca gggtaaatta ttcagttaag aaaaaaataa | 1200 |
| ttttatgaac tgcatgtata aatgaagttt atacagtaca gtggttctac aatctatta | 1260 |
| ttggacatgt ccatgaccag aagggaaaca gtcatttgcg cacaacttaa aaagtctgca | 1320 |
| ttacattcct tgataatgtt gtggtttgtt gccgttgcca agaactgaaa acataaaaag | 1380 |
| ttaaaaaaaa taataaattg catgctgctt taattgtgaa ttgataataa actgtcctct | 1440 |
| ttcagaaaac agaaaaaaaa cacacacaca caacaaaa atttgaacca aaacattccg | 1500 |
| tttacatttt agacagtaag tatcttcgtt cttgttagta ctatatctgt tttactgctt | 1560 |
| ttaacttctg atagcgttgg aattaaaaca atgtcaaggt gctgttgtca ttgctttact | 1620 |
| ggcttagggg atgggggatg gggggtatat ttttgtttgt tttgtgtttt tttttcgttt | 1680 |
| gtttgtttg ttttttagtt cccacaggga gtagagatgg ggaagaattc cctacaatat | 1740 |
| atattctggc tgataaaaga tacatttgta tgttgtgaag atgtttgcaa tatcgatcag | 1800 |
| atgactagaa agtgaataaa aattaaggca actgaacaaa aaaatgctca cactccacat | 1860 |
| cccgtgatgc acctcccagg ccccgctcat tcttgggcg ttggtcagag taagctgctt | 1920 |
| ttgacggaag gacctatgtt tgctcagaac acattctttc cccccctccc cctctggtct | 1980 |
| cctctttgtt ttgttttaag gaagaaaaat cagttcgcgc ttctgaaata ttttaccact | 2040 |
| gctgtgaaca agtgaacaca ttgtgtcaca tcatgacact cgtataagca tggagaacag | 2100 |

```
tgattttttt ttagaacaga aaacaacaaa aaataacccc aaaatgaaga ttatttttta    2160
tgaggagtga acatttgggt aaatcatggc taagcttaaa aaaaactcat ggtgaggctt    2220
aacaatgtct tgtaagcaaa aggtagagcc ctgtatcaac ccagaaacac ctagatcaga    2280
acaggaatcc acattgccag tgacatgaga ctgaacagcc aaatggaggc tatgtggagt    2340
tggcattgca tttaccggca gtgcgggagg aatttctgag tggccatccc aaggtctagg    2400
tggaggtggg gcatggtatt tgagacattc caaaacgaag gcctctgaag gacccttcag    2460
aggtggctct ggaatgacat gtgtcaagct gcttggacct cgtgctttaa gtgcctacat    2520
tatctaactg tgctcaagag gttctcgact ggaggaccac actcaagccg acttatgccc    2580
accatcccac ctctggataa ttttgcataa aattggatta gcctggagca ggttgggagc    2640
caaatgtggc atttgtgatc atgagattga tgcaatgaga tagaagatgt ttgctacctg    2700
aacacttatt gctttgaaac tagacttgag gaaaccaggg tttatctttt gagaactttt    2760
ggtaagggaa aagggaacag gaaaagaaac cccaaactca ggccgaatga tcaaggggac    2820
ccataggaaa tcttgtccag agacaagact tcgggaaggt gtctggacat tcagaacacc    2880
aagacttgaa ggtgccttgc tcaatggaag aggccaggac agagctgaca aaattttgct    2940
ccccagtgaa ggccacagca accttctgcc catcctgtct gttcatggag agggtccctg    3000
cctcacctct gccattttgg gttaggagaa gtcaagttgg gagcctgaaa tagtggttct    3060
tggaaaaatg gatccccagt gaaaactaga gctctaagcc cattcagccc atttcacacc    3120
tgaaaatgtt agtgatcacc acttggacca gcatccttaa gtatcagaaa gccccaagca    3180
attgctgcat cttagtaggg tgagggataa gcaaagagg atgttcacca taacccagga    3240
atgaagatac catcagcaaa gaatttcaat ttgttcagtc tttcatttag agctagtctt    3300
tcacagtacc atctgaatac ctctttgaaa gaaggaagac tttacgtagt gtagatttgt    3360
tttgtgttgt ttgaaaatat tatctttgta attattttta atatgtaagg aatgcttgga    3420
atatctgcta tatgtcaact ttatgcagct tcctttgag ggacaaattt aaaacaaaca    3480 acccccatc acaaacttaa aggattgcaa gggccagatc tgttaagtgg tttcatagga    3540
gacacatcca gcaattgtgt ggtcagtggc tcttttaccc aataagatac atcacagtca    3600
catgcttgat ggtttatgtt gacctaagat ttattttgtt aaaatctctc tctgttgtgt    3660
tcgttcttgt tctgtttgt tttgtttttt aaagtcttgc tgtggtctct ttgtggcaga    3720
agtgtttcat gcatggcagc aggcctgttg cttttttatg gcgattccca ttgaaaatgt    3780
aagtaaatgt ctgtggcctt gttctctcta tggtaaagat attattcacc atgtaaaaca    3840
aaaaacaata tttattgtat tttagtatat ttatataatt atgttattga aaaaaattgg    3900
cattaaaact taaccgcatc agaacctatt gtaaatacaa gttctatttta agtgtactaa    3960 ttaacatata atatatgttt taaatataga attttttaatg tttttaaata tattttcaaa    4020
gtacataaaa aaaaaaaaaa aaaa                                           4044

<210> SEQ ID NO 27
<211> LENGTH: 3972
<212> TYPE: DNA
<213> ORGANISM: Homo sapiens

<400> SEQUENCE: 27
gctgccgccg ccgcgcccgg gcgcacccgc ccgctcgctg tcccgcgcac ccgtagcgc       60 ctcgggctcc cggggccggac agaggagcca gccggtgcg ccctccacc tcctgctcgg     120 ggggctttaa tgagacaccc accgctgctg tggggccggc ggggagcagc accgcgacgg    180
```

```
ggaccggggc tgggcgctgg agccagaatc ggaaccacga tgtgactccg ccgccgggga    240
cccgtgaggt ttgtgtggac cccgagttcc accaggtgag aagagtgatg accatccttt    300
tccttactat ggttatttca tactttggtt gcatgaaggc tgcccccatg aaagaagcaa    360
acatccgagg acaaggtggc ttggcctacc caggtgtgcg gacccatggg actctggaga    420
gcgtgaatgg gcccaaggca ggttcaagag gcttgacatc attggctgac actttcgaac    480
acgtgataga gagctgttg gatgaggacc agaaagttcg gcccaatgaa gaaaacaata    540
aggacgcaga cttgtacacg tccagggtga tgctcagtag tcaagtgcct ttggagcctc    600
ctcttctctt tctgctggag gaatacaaaa attacctaga tgctgcaaac atgtccatga    660
gggtccggcg ccactctgac cctgcccgcc gaggggagct gagcgtgtgt gacagtatta    720
gtgagtgggt aacggcggca gacaaaaaga ctgcagtgga catgtcgggc gggacggtca    780
cagtccttga aaaggtccct gtatcaaaag ccaactgaa gcaatacttc tacgagacca    840
agtgcaatcc catgggttac acaaaagaag gctgcagggg catagacaaa aggcattgga    900
actcccagtg ccgaactacc cagtcgtacg tgcgggccct taccatggat agcaaaaaga    960
gaattggctg gcgattcata aggatagaca cttcttgtgt atgtacattg accattaaaa   1020
ggggaagata gtggatttat gttgtataga ttagattata ttgagacaaa aattatctat   1080
ttgtatatat acataacagg gtaaattatt cagttaagaa aaaaataatt ttatgaactg   1140
catgtataaa tgaagtttat acagtacagt ggttctacaa tctatttatt ggacatgtcc   1200
atgaccagaa gggaaacagt catttgcgca caacttaaaa agtctgcatt acattccttg   1260
ataatgttgt ggtttgttgc cgttgccaag aactgaaaac ataaaaagtt aaaaaaaata   1320
ataaattgca tgctgcttta attgtgaatt gataataaac tgtcctcttt cagaaaacag   1380
aaaaaaaaca cacacacaca caacaaaaat ttgaaccaaa acattccgtt tacattttag   1440
acagtaagta tcttcgttct tgttagtact atatctgttt tactgctttt aacttctgat   1500
agcgttggaa ttaaaacaat gtcaaggtgc tgttgtcatt gctttactgg cttaggggat   1560
gggggatggg gggtatattt ttgtttgttt tgtgttttt tttcgtttgt ttgttttgtt    1620
ttttagttcc cacagggagt agagatgggg aaagaattcc tacaatatat attctggctg   1680 ataaagata catttgtatg ttgtgaagat gtttgcaata tcgatcagat gactagaaag    1740
tgaataaaaa ttaaggcaac tgaacaaaaa aatgctcaca ctccacatcc cgtgatgcac   1800
ctcccaggcc ccgctcattc tttgggcgtt ggtcagagta agctgctttt gacggaagga   1860
cctatgtttg ctcagaacac attctttccc cccctccccc tctggtctcc tctttgtttt   1920
gttttaagga agaaaaatca gttgcgcgtt ctgaaatatt ttaccactgc tgtgaacaag   1980
tgaacacatt gtgtcacatc atgacactcg tataagcatg gagaacagtg atttttttt    2040 agaacagaaa acaacaaaaa ataaccccaa aatgaagatt attttttatg aggagtgaac   2100
atttgggtaa atcatggcta agcttaaaaa aaactcatgg tgaggcttaa caatgtcttg   2160
taagcaaaag gtagagccct gtatcaaccc agaaacacct agatcagaac aggaatccac   2220
attgccagtg acatgagact gaacagccaa atggaggcta tgtggagttg cattgcatt    2280 taccggcagt gcgggaggaa tttctgagtg gccatcccaa ggtctaggtg gaggtggggc   2340
atggtatttg agacattcca aaacgaaggc ctctgaagga cccttcagag gtggctctgg   2400
aatgacatgt gtcaagctgc ttggacctcg tgctttaagt gcctacatta tctaactgtg   2460
ctcaagaggt tctcgactgg aggaccacac tcaagccgac ttatgcccac catcccacct   2520
ctggataatt ttgcataaaa ttggattagc ctggagcagg ttgggagcca aatgtggcat   2580
```

```
ttgtgatcat gagattgatg caatgagata gaagatgttt gctacctgaa cacttattgc    2640
tttgaaacta gacttgagga aaccagggtt tatcttttga gaacttttgg taagggaaaa    2700
gggaacagga aaagaaaccc caaactcagg ccgaatgatc aaggggaccc ataggaaatc    2760
ttgtccagag acaagacttc gggaaggtgt ctggacattc agaacaccaa gacttgaagg    2820
tgccttgctc aatggaagag gccaggacag agctgacaaa attttgctcc ccagtgaagg    2880
ccacagcaac cttctgccca tcctgtctgt tcatggagag ggtccctgcc tcacctctgc    2940
cattttgggt taggagaagt caagttggga gcctgaaata gtggttcttg gaaaatggaa    3000
tccccagtga aaactagagc tctaagccca ttcagcccat ttcacacctg aaaatgttag    3060
tgatcaccac ttggaccagc atccttaagt atcagaaagc cccaagcaat tgctgcatct    3120
tagtagggtg agggataagc aaaagaggat gttcaccata acccaggaat gaagatacca    3180
tcagcaaaga atttcaattt gttcagtctt tcatttagag ctagtctttc acagtaccat    3240
ctgaataccc tttgaaaga aggaagactt tacgtagtgt agatttgttt tgtgttgttt    3300
gaaaatatta tctttgtaat tattttaat atgtaaggaa tgcttggaat atctgctata    3360
tgtcaacttt atgcagcttc cttttgaggg acaaatttaa aacaaacaac cccccatcac    3420
aaacttaaag gattgcaagg gccagatctg ttaagtggtt tcataggaga cacatccagc    3480
aattgtgtgg tcagtggctc ttttacccaa taagatacat cacagtcaca tgcttgatgg    3540
tttatgttga cctaagattt attttgttaa aatctctctc tgttgtgttc gttcttgttc    3600
tgttttgttt tgttttttaa agtcttgctg tggtctcttt gtggcagaag tgtttcatgc    3660
atggcagcag gcctgttgct tttttatggc gattcccatt gaaaatgtaa gtaaatgtct    3720
gtggccttgt tctctctatg gtaaagatat tattcaccat gtaaaacaaa aacaatatt    3780 tattgtattt tagtatattt atataattat gttattgaaa aaaattggca ttaaaactta    3840
accgcatcag aacctattgt aaatacaagt tctatttaag tgtactaatt aacatataat    3900 atatgttttta aatatagaat ttttaatgtt tttaaatata ttttcaaagt acataaaaaa    3960
aaaaaaaaaa aa                                                       3972
```

<210> SEQ ID NO 28
<211> LENGTH: 4016
<212> TYPE: DNA
<213> ORGANISM: Homo sapiens

<400> SEQUENCE: 28

```
ggctgctctc gctgccgctc cccccggcga actagcatga aatctccctg cctctgccga     60
gatcaaatgg agcttctcgc tgatggggtg cgagtattac ctccgccatg caatttccac    120
tatcaataat ttaacttctt tgctgcagaa cagaaggagt acataccggg caccaaagac    180
tcgcgccccc tccccccttt aattaagcga agggaacgtg aaaaaataat agagtgtggg    240
agttttgggg ccgaagtctt tcccggagca gctgccttga tggttacttt gacaagtagt    300
gactgaaaag ttccaccagg tgagaagagt gatgaccatc cttttcctta ctatggttat    360
ttcatacttt ggttgcatga aggctgcccc catgaaagaa gcaaacatcc gaggacaagg    420
tggcttggcc tacccaggtg tgcggaccca tgggactctg agagcgtga atgggcccaa    480 ggcaggttca agaggcttga catcattggc tgacactttc gaacacgtga tagaagagct    540
gttggatgag gaccagaaag ttcggcccaa tgaagaaaac aataaggacg cagacttgta    600
cacgtccagg gtgatgctca gtagtcaagt gcctttggag cctcctcttc tctttctgct    660
ggaggaatac aaaaattacc tagatgctgc aaacatgtcc atgagggtcc ggcgccactc    720
```

```
tgaccctgcc cgccgagggg agctgagcgt gtgtgacagt attagtgagt gggtaacggc    780
ggcagacaaa aagactgcag tggacatgtc gggcgggacg gtcacagtcc ttgaaaaggt    840
ccctgtatca aaaggccaac tgaagcaata cttctacgag accaagtgca atcccatggg    900
ttacacaaaa gaaggctgca ggggcataga caaaaggcat ggaactccc  agtgccgaac    960
tacccagtcg tacgtgcggg cccttaccat ggatagcaaa agagaattg  gctggcgatt   1020
cataaggata gacacttctt gtgtatgtac attgaccatt aaaaggggaa gatagtggat   1080
ttatgttgta tagattagat tatattgaga caaaaattat ctatttgtat atatacataa   1140
cagggtaaat tattcagtta agaaaaaaat aattttatga actgcatgta taaatgaagt   1200
ttatacagta cagtggttct acaatctatt tattggacat gtccatgacc agaagggaaa   1260
cagtcatttg cgcacaactt aaaaagtctg cattacattc cttgataatg ttgtggtttg   1320
ttgccgttgc caagaactga aaacataaaa agttaaaaaa aataataaat tgcatgctgc   1380
tttaattgtg aattgataat aaactgtcct ctttcagaaa acagaaaaaa aacacacaca   1440
cacacaacaa aaatttgaac caaaacattc cgtttacatt ttagacagta agtatcttcg   1500
ttcttgttag tactatatct gttttactgc ttttaacttc tgatagcgtt ggaattaaaa   1560
caatgtcaag gtgctgttgt cattgcttta ctggcttagg ggatggggga tgggggtat   1620
attttttgttt gttttgtgtt ttttttttcgt ttgtttgttt tgtttttag ttcccacagg   1680
gagtagagat ggggaaagaa ttcctacaat atatattctg gctgataaaa gatacatttg   1740
tatgttgtga agatgtttgc aatatcgatc agatgactag aaagtgaata aaaattaagg   1800
caactgaaca aaaaaatgct cacactccac atcccgtgat gcacctccca ggccccgctc   1860
attctttggg cgttggtcag agtaagctgc ttttgacgga aggacctatg tttgctcaga   1920
acacattctt tcccccctc ccctctggt ctcctctttg ttttgtttta aggaagaaaa   1980
atcagttgcg cgttctgaaa tattttacca ctgctgtgaa caagtgaaca cattgtgtca   2040
catcatgaca ctcgtataag catggagaac agtgattttt ttttagaaca gaaaacaaca   2100
aaaaataacc ccaaaatgaa gattattttt tatgaggagt gaacatttgg gtaaatcatg   2160
gctaagctta aaaaaaactc atggtgaggc ttaacaatgt cttgtaagca aaaggtagag   2220
ccctgtatca acccagaaac acctagatca gaacaggaat ccacattgcc agtgacatga   2280
gactgaacag ccaaatggag gctatgtgga gttggcattg catttaccgg cagtgcggga   2340
ggaatttctg agtggccatc ccaaggtcta ggtggaggtg gggcatggta tttgagacat   2400
tccaaaacga aggcctctga aggacccttc agaggtggct ctggaatgac atgtgtcaag   2460
ctgcttggac ctcgtgcttt aagtgcctac attatctaac tgtgctcaag aggttctcga   2520
ctggaggacc acactcaagc cgacttatgc ccaccatccc acctctggat aattttgcat   2580
aaaattggat tagcctggag caggttggga gccaaatgtg gcatttgtga tcatgagatt   2640
gatgcaatga gatagaagat gtttgctacc tgaacactta ttgctttgaa actagacttg   2700
aggaaaccag ggtttatctt ttgagaactt ttggtaaggg aaaagggaac aggaaaagaa   2760
accccaaact caggccgaat gatcaagggg acccatagga aatcttgtcc agagacaaga   2820
cttcgggaag gtgtctggac attcagaaca ccaagacttg aaggtgcctt gctcaatgga   2880
agaggccagg acagagctga caaaattttg ctccccagtg aaggccacag caaccttctg   2940
cccatcctgt ctgttcatgg agagggtccc tgcctcacct ctgccatttt gggttaggag   3000
aagtcaagtt gggagcctga aatagtggtt cttggaaaaa tggatcccca gtgaaaacta   3060
gagctctaag cccattcagc ccatttcaca cctgaaaatg ttagtgatca ccacttggac   3120
```

```
cagcatcctt aagtatcaga aagccccaag caattgctgc atcttagtag ggtgagggat   3180
aagcaaaaga ggatgttcac cataacccag gaatgaagat accatcagca aagaatttca   3240
atttgttcag tctttcattt agagctagtc tttcacagta ccatctgaat acctctttga   3300
aagaaggaag actttacgta gtgtagattt gttttgtgtt gtttgaaaat attatctttg   3360
taattatttt taatatgtaa ggaatgcttg gaatatctgc tatatgtcaa ctttatgcag   3420 cttcctttttg agggacaaat ttaaaacaaa caaccccccca tcacaaactt aaaggattgc   3480
aagggccaga tctgttaagt ggtttcatag gagacacatc cagcaattgt gtggtcagtg   3540
gctcttttac ccaataagat acatcacagt cacatgcttg atggtttatg ttgacctaag   3600 atttatttttg ttaaaatctc tctctgttgt gttcgttctt gttctgtttt gttttgtttt   3660
ttaaagtctt gctgtggtct ctttgtggca gaagtgtttc atgcatggca gcaggcctgt   3720 tgcttttttta tggcgattcc cattgaaaat gtaagtaaat gtctgtggcc ttgttctctc   3780
tatggtaaag atattattca ccatgtaaaa caaaaaacaa tatttattgt attttagtat   3840
atttatataa ttatgttatt gaaaaaaatt ggcattaaaa cttaaccgca tcagaaccta   3900
ttgtaaatac aagttctatt taagtgtact aattaacata taatatatgt tttaaatata   3960 gaattttttaa tgtttttaaa tatattttca aagtacataa aaaaaaaaaa aaaaaa      4016

<210> SEQ ID NO 29
<211> LENGTH: 3958
<212> TYPE: DNA
<213> ORGANISM: Homo sapiens

<400> SEQUENCE: 29
agtggactta caagtccgaa gccaatgtag cttggaaaac ttgggaggcg gaattcctac     60
cgctgggaac tgaaagggtc tgcgacactc tcgggcaggc cgaacccaca tctctaccca    120
tcctgcgccc ctcttctgaa gcgccctcca gggaagttaa gagttttgac tttcggggag    180
tggttgggat gtacgtgggg gattcttgac tcggttagt ctctggggat gcagagccgg    240
gaagaggaat ggttccacca ggtgagaaga gtgatgacca tccttttcct tactatggtt    300
atttcatact ttggttgcat gaaggctgcc cccatgaaag aagcaaacat ccgaggacaa    360
ggtggcttgg cctacccagg tgtgcggacc catgggactc tggagagcgt gaatgggccc    420
aaggcaggtt caagaggctt gacatcattg gctgacactt tcgaacacgt gatagaagag    480
ctgttggatg aggaccagaa agttcggccc aatgaagaaa acaataagga cgcagacttg    540
tacacgtcca gggtgatgct cagtagtcaa gtgcctttgg agcctcctct tctctttctg    600
ctggaggaat acaaaaatta cctagatgct gcaaacatgt ccatgagggt ccggcgccac    660
tctgaccctg cccgccgagg ggagctgagc gtgtgtgaca gtattagtga gtgggtaacg    720
gcggcagaca aaaagactgc agtggacatg tcgggcggga cggtcacagt ccttgaaaag    780
gtccctgtat caaaaggcca actgaagcaa tacttctacg agaccaagtg caatcccatg    840
ggttacacaa agaaggctg cagggcata gacaaaaggc attggaactc ccagtgccga    900
actacccagt cgtacgtgcg ggcccttacc atggatagca aaagagaat tggctggcga    960 ttcataagga tagacacttc ttgtgtatgt acattgacca ttaaaagggg aagatagtgg   1020
atttatgttg tatagattag attatattga gacaaaaatt atctatttgt atatatacat   1080
aacagggtaa attattcagt taagaaaaaa ataatttttat gaactgcatg tataaatgaa   1140
gtttatacag tacagtggtt ctacaatcta tttattggac atgtccatga ccagaaggga   1200
aacagtcatt tgcgcacaac ttaaaaagtc tgcattacat tccttgataa tgttgtggtt   1260
```

```
tgttgccgtt gccaagaact gaaaacataa aaagttaaaa aaaataataa attgcatgct    1320
gctttaattg tgaattgata ataaactgtc ctctttcaga aaacagaaaa aaaacacaca    1380
cacacacaac aaaaatttga accaaaacat tccgtttaca ttttagacag taagtatctt    1440
cgttcttgtt agtactatat ctgttttact gcttttaact tctgatagcg ttggaattaa    1500
aacaatgtca aggtgctgtt gtcattgctt tactggctta ggggatgggg gatgggggt     1560 atattttgt ttgttttgtg ttttttttc gtttgtttgt tttgttttt agttcccaca       1620 gggagtagag atggggaaag aattcctaca atatatattc tggctgataa aagatacatt    1680
tgtatgttgt gaagatgttt gcaatatcga tcagatgact agaaagtgaa taaaaattaa    1740
ggcaactgaa caaaaaaatg ctcacactcc acatcccgtg atgcacctcc caggccccgc    1800
tcattctttg ggcgttggtc agagtaagct gcttttgacg gaaggaccta tgtttgctca    1860
gaacacattc tttccccccc tcccctctg gtctcctctt tgttttgttt taaggaagaa     1920
aaatcagttg cgcgttctga aatattttac cactgctgtg aacaagtgaa cacattgtgt    1980
cacatcatga cactcgtata agcatggaga acagtgattt ttttttagaa cagaaaacaa    2040
caaaaaataa ccccaaaatg aagattattt tttatgagga gtgaacattt gggtaaatca    2100
tggctaagct taaaaaaaac tcatggtgag gcttaacaat gtcttgtaag caaaaggtag    2160
agccctgtat caacccagaa acacctagat cagaacagga atccacattg ccagtgacat    2220
gagactgaac agccaaatgg aggctatgtg gagttggcat tgcatttacc ggcagtgcgg    2280
gaggaatttc tgagtggcca tcccaaggtc taggtgagg tggggcatgg tatttgagac     2340
attccaaaac gaaggcctct gaaggaccct tcagaggtgg ctctggaatg acatgtgtca    2400
agctgcttgg acctcgtgct ttaagtgcct acattatcta actgtgctca agaggttctc    2460
gactggagga ccacactcaa gccgacttat gcccaccatc ccacctctgg ataattttgc    2520
ataaaattgg attagcctgg agcaggttgg gagccaaatg tggcatttgt gatcatgaga    2580
ttgatgcaat gagatagaag atgtttgcta cctgaacact tattgctttg aaactagact    2640
tgaggaaacc agggtttatc ttttgagaac ttttggtaag ggaaaaggga acaggaaaag    2700
aaaccccaaa ctcaggccga atgatcaagg ggacccatag gaaatcttgt ccagagacaa    2760
gacttcggga aggtgtctgg acattcagaa caccaagact tgaaggtgcc ttgctcaatg    2820
gaagaggcca ggacagagct gacaaaattt tgctccccag tgaaggccac agcaaccttc    2880
tgcccatcct gtctgttcat ggagagggtc cctgcctcac ctctgccatt tgggttagg    2940 agaagtcaag ttgggagcct gaaatagtgg ttccttggaaa aatggatccc cagtgaaaac   3000
tagagctcta agcccattca gcccatttca cacctgaaaa tgttagtgat caccacttgg   3060
accagcatcc ttaagtatca gaaagcccca agcaattgct gcatcttagt agggtgaggg    3120
ataagcaaaa gaggatgttc accataaccc aggaatgaag ataccatcag caaagaattt    3180
caatttgttc agtctttcat ttagagctag tcttcacag taccatctga atacctcttt     3240
gaaagaagga agactttacg tagtgtagat ttgttttgtg ttgtttgaaa atattatctt    3300
tgtaattatt tttaatatgt aaggaatgct tggaatatct gctatatgtc aactttatgc    3360
agcttccttt tgagggacaa atttaaaaca aacaaccccc catcacaaac ttaaaggatt    3420
gcaagggcca gatctgttaa gtggtttcat aggagacaca tccagcaatt gtgtggtcag    3480
tggctctttt acccaataag atacatcaca gtcacatgct tgatggttta tgttgaccta    3540 agattttattt tgttaaaatc tctctctgtt gtgttcgttc ttgttctgtt ttgttttgtt   3600
ttttaaagtc ttgctgtggt ctctttgtgg cagaagtgtt tcatgcatgg cagcaggcct    3660
```

```
gttgctttt  tatggcgatt  cccattgaaa  atgtaagtaa  atgtctgtgg  ccttgttctc    3720
tctatggtaa  agatattatt  caccatgtaa  aacaaaaaac  aatatttatt  gtattttagt    3780
atatttatat  aattatgtta  ttgaaaaaaa  ttggcattaa  aacttaaccg  catcagaacc    3840
tattgtaaat  acaagttcta  tttaagtgta  ctaattaaca  tataatatat  gttttaaata    3900
tagaattttt  aatgttttta  aatatatttt  caaagtacat  aaaaaaaaaa  aaaaaaa      3958
```

<210> SEQ ID NO 30
<211> LENGTH: 836
<212> TYPE: DNA
<213> ORGANISM: Homo sapiens

<400> SEQUENCE: 30

```
ccgcctccag  cgcgcccttg  ctgccccgcg  cgaccccagg  attgcgaact  cttgcccctg     60
acctgttggg  cggggctccg  cgctccagcc  atcagcccgg  atgggtctcc  tggctgggac    120
ttggggcacc  tggagttaat  gtccaaccta  gggtctgcgg  agacccgatc  cgaggtgccg    180
ccgccggacg  ggactttaag  atgaagttat  gggatgtcgt  ggctgtctgc  ctggtgctgc    240
tccacaccgc  gtccgccttc  ccgctgcccg  ccggtaagag  gcctcccgag  gcgcccgccg    300
aagaccgctc  cctcggccgc  cgccgcgcgc  ccttcgcgct  gagcagtgac  tcaaatatgc    360
cagaggatta  tcctgatcag  ttcgatgatg  tcatggattt  tattcaagcc  accattaaaa    420
gactgaaaag  gtcaccagat  aaacaaatgg  cagtgcttcc  tagaagagag  cggaatcggc    480
aggctgcagc  tgccaaccca  gagaattcca  gaggaaaagg  tcggagaggc  cagagggggca   540 aaaaccgggg  ttgtgtctta  actgcaatac  atttaaatgt  cactgacttg  ggtctgggct    600
atgaaaccaa  ggaggaactg  attttttaggt  actgcagcgg  ctcttgcgat  gcagctgaga    660
caacgtacga  caaaatattg  aaaaacttat  ccagaaatag  aaggctggtg  agtgacaaag    720
tagggcaggc  atgttgcaga  cccatcgcct  ttgatgatga  cctgtcgttt  ttagatgata    780
acctggttta  ccatattcta  agaaagcatt  ccgctaaaag  gtgtggatgt  atctga        836
```

<210> SEQ ID NO 31
<211> LENGTH: 681
<212> TYPE: DNA
<213> ORGANISM: Homo sapiens

<400> SEQUENCE: 31

```
catacgggcc  aaaagtctcc  aagtccctgc  taacttcttg  ctctcgcaac  agaataccta     60
tttaggtggg  aagaatgagg  tgtgggcggc  aggctgggtg  ccgccgccgg  acgggacttt    120
aagatgaagt  tatgggatgt  cgtggctgtc  tgcctggtgc  tgctccacac  cgcgtccgcc    180
ttcccgctgc  ccgccgcaaa  tatgccagag  gattatcctg  atcagttcga  tgatgtcatg    240
gattttattc  aagccaccat  taaaagactg  aaaaggtcac  cagataaaca  aatggcagtg    300
cttcctagaa  gagagcggaa  tcggcaggct  gcagctgcca  acccagagaa  ttccagagga    360
aaaggtcgga  gaggccagag  ggggcaaaaac  cggggttgtg  tcttaactgc  aatacattta    420
aatgtcactg  acttgggtct  gggctatgaa  accaaggagg  aactgatttt  taggtactgc    480
agcggctctt  gcgatgcagc  tgagacaacg  tacgacaaaa  tattgaaaaa  cttatccaga    540
aatagaaggc  tggtgagtga  caaagtaggg  caggcatgtt  gcagacccat  cgcctttgat    600
gatgacctgt  cgttttttaga  tgataacctg  gtttaccata  ttctaagaaa  gcattccgct    660
aaaaggtgtg  gatgtatctg  a                                                681
```

<210> SEQ ID NO 32

```
<211> LENGTH: 410
<212> TYPE: DNA
<213> ORGANISM: Homo sapiens

<400> SEQUENCE: 32
atgaagttat gggatgtcgt ggctgtctgc ctggtgctgc tccacaccgc gtccgccttc      60
ccgctgccaa cccagagaat tccagaggaa aaggtcggag aggccagagg ggcaaaaacc     120
ggggttgtgt cttaactgca atacatttaa atgtcactga cttgggtctg gctatgaaa      180 ccaaggagga actgattttt aggtactgca gcggctcttg cgatgcagct gagacaacgt     240
acgacaaaat attgaaaaac ttatccagaa atagaaggct ggtgagtgac aaagtagggc     300
aggcatgttg cagacccatc gcctttgatg atgacctgtc gttttagat gataacctgg      360 tttaccatat tctaagaaag cattccgcta aaggtgtgg atgtatctga               410

<210> SEQ ID NO 33
<211> LENGTH: 1052
<212> TYPE: DNA
<213> ORGANISM: Homo sapiens

<400> SEQUENCE: 33
agagagcgct gggagccgga ggggagcgca gcgagttttg gccagtggtc gtgcagtcca      60
aggggctgga tggcatgctg gacccaagct cagctcagcg tccggaccca ataacagttt     120
taccaaggga gcagctttct atcctggcca cactgaggtg catagcgtaa tgtccatgtt     180
gttctacact ctgatcacag cttttctgat cggcatacag gcggaaccac actcagagag     240
caatgtccct gcaggacaca ccatccccca agcccactgg actaaacttc agcattccct     300
tgacactgcc cttcgcagag cccgcagcgc cccggcagcg gcgatagctg cacgcgtggc     360
ggggcagacc cgcaacatta ctgtggaccc caggctgttt aaaaagcggc gactccgttc     420
accccgtgtg ctgtttagca cccagcctcc ccgtgaagct gcagacactc aggatctgga     480
cttcgaggtc ggtggtgctg cccccttcaa caggactcac aggagcaagc ggtcatcatc     540
ccatcccatc ttccacaggg gcgaattctc ggtgtgtgac agtgtcagcg tgtgggttgg     600
ggataagacc accgccacag acatcaaggg caaggaggtg atggtgttgg agaggtgaa      660 cattaacaac agtgtattca acagtactt ttttgagacc aagtgccggg acccaaatcc      720
cgttgacagc gggtgccggg gcattgactc aaagcactgg aactcatatt gtaccacgac     780
tcacaccttt gtcaaggcgc tgaccatgga tggcaagcag gctgcctggc ggtttatccg     840
gatagatacg gcctgtgtgt gtgtgctcag caggaaggct gtgagaagag cctgacctgc     900
cgacacgctc cctcccctg cccttctac actctctgg gccctccct acctcaacct        960 gtaaattatt taaattata aggactgcat ggtaatttat agtttataca gttttaaga      1020 atcattattt attaaatttt tggaagcata aa                                 1052

<210> SEQ ID NO 34
<211> LENGTH: 7260
<212> TYPE: DNA
<213> ORGANISM: Homo sapiens

<400> SEQUENCE: 34
tcactgtcac tgctaaattc agagcagatt agagcctgcg caatggaata aagtcctcaa      60
aattgaaatg tgacattgct ctcaacatct cccatctctc tggatttcct tttgcttcat     120
tattcctgct aaccaattca ttttcagact ttgtacttca gaagcaatgg gaaaaatcag     180
cagtcttcca acccaattat ttaagtgctg cttttgtgat ttcttgaagg tgaagatgca     240
```

```
caccatgtcc tcctcgcatc tcttctacct ggcgctgtgc ctgctcacct tcaccagctc    300
tgccacggct ggaccggaga cgctctgcgg ggctgagctg gtggatgctc ttcagttcgt    360
gtgtggagac aggggctttt atttcaacaa gcccacaggg tatggctcca gcagtcggag    420
ggcgcctcag acaggcatcg tggatgagtg ctgcttccgg agctgtgatc taaggaggct    480
ggagatgtat tgcgcacccc tcaagcctgc caagtcagct cgctctgtcc gtgcccagcg    540
ccacaccgac atgcccaaga cccagaagga agtacatttg aagaacgcaa gtagagggag    600
tgcaggaaac aagaactaca ggatgtagga agaccctcct gaggagtgaa gagtgacatg    660
ccaccgcagg atcctttgct ctgcacgagt tacctgttaa actttggaac acctaccaaa    720
aaataagttt gataacattt aaaagatggg cgtttccccc aatgaaatac acaagtaaac    780
attccaacat tgtctttagg agtgatttgc accttgcaaa atggtcctg gagttggtag     840 attgctgttg atcttttatc aataatgttc tatagaaaag aaaaaaaaat atatatatat    900
atatatctta gtccctgcct ctcaagagcc acaaatgcat gggtgttgta tagatccagt    960
tgcactaaat tcctctctga atcttggctg ctggagccat tcattcagca accttgtcta   1020
agtggtttat gaattgtttc cttatttgca cttctttcta cacaactcgg gctgtttgtt   1080
ttacagtgtc tgataatctt gttagtctat acccaccacc tcccttcata acctttatat   1140
ttgccgaatt tggcctcctc aaaagcagca gcaagtcgtc aagaagcaca ccaattctaa   1200
cccacaagat tccatctgtg gcatttgtac caaatataag ttggatgcat tttattttag   1260
acacaaagct ttattttttcc acatcatgct tacaaaaaag aataatgcaa atagttgcaa   1320
ctttgaggcc aatcattttt aggcatatgt tttaaacata gaaagtttct tcaactcaaa   1380
agagttcctt caaatgatga gttaatgtgc aacctaatta gtaactttcc tcttttatt    1440 ttttccatat agagcactat gtaaatttag catatcaatt atacaggata tatcaaacag   1500
tatgtaaaac tctgtttttt agtataatgg tgctattttg tagtttgtta tatgaaagag   1560
tctggccaaa acggtaatac gtgaaagcaa acaataggg gaagcctgga gccaaagatg    1620
acacaagggg aagggtactg aaaacaccat ccatttggga agaaggcaa agtcccccca    1680 gttatgcctt ccaagaggaa cttcagacac aaaagtccac tgatgcaaat tggactggcg   1740
agtccagaga ggaaactgtg gaatggaaaa agcagaaggc taggaatttt agcagtcctg   1800 gtttctttttt ctcatggaag aaatgaacat ctgccagctg tgtcatggac tcaccactgt   1860
gtgaccttgg gcaagtcact tcacctctct gtgcctcagt ttcctcatct gcaaaatggg   1920
ggcaatatgt catctaccta cctcaaaggg gtggtataag gttaaaaag ataaagattc     1980 agatttttttt accctgggtt gctgtaaggg tgcaacatca gggcgcttga gttgctgaga   2040
tgcaaggaat tctataaata acccattcat agcatagcta gagattggtg aattgaatgc   2100
tcctgacatc tcagttcttg tcagtgaagc tatccaaata actggccaac tagttgttaa   2160
aagctaacag ctcaatctct taaaacactt ttcaaaatat gtgggaagca tttgattttc   2220
aatttgattt tgaattctgc atttggtttt atgaatacaa agataagtga aaagagagaa   2280
aggaaaagaa aaaggagaaa aacaaagaga tttctaccag tgaaagggga attaattact   2340
ctttgttagc actcactgac tcttctatgc agttactaca tatctagtaa aaccttgttt   2400
aatactataa ataatattct attcatttg aaaaacacaa tgattccttc ttttctaggc    2460
aatataagga aagtgatcca aaatttgaaa tattaaaata atatctaata aaagtcaca    2520 aagttatctt cttttaacaaa ctttactctt attcttagct gtatatacat ttttttaaaa   2580
agtttgttaa aatatgcttg actagagttt cagttgaaag gcaaaaactt ccatcacaac   2640
```

-continued

```
aagaaatttc ccatgcctgc tcagaagggt agccctagc tctctgtgaa tgtgttttat    2700
ccattcaact gaaaattggt atcaagaaag tccactggtt agtgtactag tccatcatag    2760
cctagaaaat gatccctatc tgcagatcaa gattttctca ttagaacaat gaattatcca    2820
gcattcagat ctttctagtc acctagaac ttttggtta aaagtaccca ggcttgatta    2880
tttcatgcaa attctatatt ttacattctt ggaaagtcta tatgaaaaac aaaaataaca    2940
tcttcagttt ttctcccact gggtcacctc aaggatcaga ggccaggaaa aaaaaaaag    3000 actccctgga tctctgaata tatgcaaaaa gaaggcccca tttagtggag ccagcaatcc    3060
tgttcagtca acaagtattt taactctcag tccaacatta tttgaattga gcacctcaag    3120
catgcttagc aatgttctaa tcactatgga cagatgtaaa agaaactata catcatttt    3180 gccctctgcc tgttttccag acatacaggt tctgtggaat aagatactgg actcctcttc    3240
ccaagatggc acttcttttt atttcttgtc cccagtgtgt accttttaaa attattccct    3300
ctcaacaaaa ctttataggc agtcttctgc agacttaaca tgttttctgt catagttaga    3360
tgtgataatt ctaagagtgt ctatgactta tttccttcac ttaattctat ccacagtcaa    3420 aaatcccca aggaggaaag ctgaaagatg caactgccaa tattatcttt cttaactttt    3480
tccaacacat aatcctctcc aactggatta taaataaatt gaaataact cattatacca    3540 attcactatt ttattttta atgaattaaa actagaaaac aaattgatgc aaaccctgga    3600
agtcagttga ttactatata ctacagcaga atgactcaga tttcatagaa aggagcaacc    3660
aaaatgtcac aaccaaaact ttacaagctt tgcttcagaa ttagattgct ttataattct    3720
tgaatgaggc aatttcaaga tatttgtaaa agaacagtaa acattggtaa gaatgagctt    3780
tcaactcata ggcttatttc caatttaatt gaccatactg gatacttagg tcaaatttct    3840
gttctctctt gcccaaataa tattaaagta ttatttgaac ttttaagat gaggcagttc    3900 ccctgaaaaa gttaatgcag ctctccatca gaatccactc ttctagggat atgaaaatct    3960
cttaacaccc accctacata cacagacaca cacacacaca cacacacaca cacacacaca    4020
cacacattca ccctaaggat ccaatggaat actgaaaaga aatcacttcc ttgaaaattt    4080
tattaaaaaa caaacaaaca aacaaaaagc ctgtccaccc ttgagaatcc ttcctctcct    4140
tggaacgtca atgtttgtgt agatgaaacc atctcatgct ctgtggctcc agggtttctg    4200
ttactatttt atgcacttgg gagaaggctt agaataaaag atgtagcaca ttttgctttc    4260
ccatttattg tttggccagc tatgccaatg tggtgctatt gtttctttaa gaaagtactt    4320
gactaaaaaa aaaagaaaaa aagaaaaaaa agaaagcata gacatatttt tttaaagtat    4380 aaaacaaca attctataga tagatggctt aataaaatag cattaggtct atctagccac    4440
caccaccttt caacttttta tcactcacaa gtagtgtact gttcaccaaa ttgtgaattt    4500
gggggtgcag gggcaggagt tggaaatttt ttaaagttag aaggctccat tgttttgttg    4560
gctctcaaac ttagcaaaat tagcaatata ttatccaatc ttctgaactt gatcaagagc    4620
atggagaata aacgcgggaa aaaagatctt ataggcaaat agaagaattt aaaagataag    4680
taagttcctt attgattttt gtgcactctg ctctaaaaca gatattcagc aagtggagaa    4740
aataagaaca aagagaaaaa atacatagat ttacctgcaa aaaatagctt ctgccaaatc    4800 cccttgggt attcttggc atttactggt ttatagaaga cattctccct tcacccagac    4860
atctcaaaga gcagtagctc tcatgaaaag caatcactga tctcatttgg gaaatgttgg    4920
aaagtatttc cttatgagat gggggttatc tactgataaa gaaagaattt atgagaaatt    4980
gttgaaagag atggctaaca atctgtgaag atttttttgtt tcttggtttt gttttttttt    5040
```

```
ttttttttac tttatacagt ctttatgaat ttcttaatgt tcaaaatgac ttggttcttt      5100
tcttcttttt tttatatcag aatgaggaat aataagttaa acccacatag actctttaaa      5160
actataggct agatagaaat gtatgtttga cttgttgaag ctataatcag actatttaaa      5220
atgttttgct atttttaatc ttaaaagatt gtgctaattt attagagcag aacctgtttg      5280
gctctcctca gaagaaagaa tctttccatt caaatcacat ggctttccac caatattttc      5340
aaaagataaa tctgatttat gcaatggcat catttatttt aaaacagaag aattgtgaaa      5400
gtttatgccc ctcccttgca aagaccataa agtccagatc tggtaggggg gcaacaacaa      5460
aaggaaaatg ttgttgattc ttggttttgg attttgtttt gttttcaatg ctagtgttta      5520
atcctgtagt acatatttgc ttattgctat tttaatattt tataagacct tcctgttagg      5580
tattagaaag tgatacatag atatcttttt tgtgtaattt ctatttaaaa aagagagaag      5640
actgtcagaa gctttaagtg catatggtac aggataaaga tatcaattta aataaccaat      5700
tcctatctgg aacaatgctt ttgttttttta aagaaacctc tcacagataa acagaggcc       5760
caggggattt ttgaagctgt ctttattctg cccccatccc aacccagccc ttattatttt      5820
agtatctgcc tcagaatttt atagagggct gaccaagctg aaactctaga attaaaggaa      5880
cctcactgaa aacatatatt tcacgtgttc cctctctttt ttttccttttt tgtgagatgg      5940
ggtctcgcac tgtcccccag gctggagtgc agtggcatga tctcggctca ctgcaacctc      6000
cacctcctgg gtttaagcga ttctcctgcc tcagcctcct gagtagctgg gattacaggc      6060
acccaccact atgcccggct aatttttttgg attttttaata gagacggggt tttaccatgt      6120
tggccaggtt ggactcaaac tcctgacctt gtgatttgcc cgcctcagcc tcccaaattg      6180
ctgggattac aggcatgagc caccacaccc tgccc atgtg ttccctctta atgtatgatt      6240
acatggatct taaacatgat ccttctctcc tcattcttca actatctttg atggggtctt      6300
tcaaggggaa aaaaatccaa gctttttttaa agtaaaaaaa aaaaagaga ggacacaaaa      6360
ccaaatgtta ctgctcaact gaaatatgag ttaagatgga gacagagttt ctcctaataa      6420
ccggagctga attacctttc acttttcaaaa acatgacctt ccacaatcct tagaatctgc      6480
cttttttttat attactgagg cctaaaagta aacattactc atttttatttt gcccaaaatg      6540
cactgatgta aagtaggaaa aataaaaaca gagctctaaa atccctttca agccacccat      6600
tgaccccact caccaactca tagcaaagtc acttctgtta atcccttaat ctgattttgt      6660
ttggatattt atcttgtacc cgctgctaaa cacactgcag gagggactct gaaacctcaa      6720
gctgtctact tacatctttt atctgtgtct gtgtatcatg aaaatgtcta ttcaaaatat      6780
caaaaccttt caaatatcac gcagcttata ttcagtttac ataaaggccc caaataccat      6840
gtcagatctt tttggtaaaa gagttaatga actatgagaa ttgggattac atcatgtatt      6900
ttgcctcatg tattttttatc acacttatag gccaagtgtg ataaataaac ttacagacac      6960
tgaattaatt tccccctgcta ctttgaaacc agaaaataat gactggccat tcgttacatc      7020
tgtcttagtt gaaaagcata ttttttatta aattaattct gattgtattt gaaattatta      7080
ttcaattcac ttatggcaga ggaatatcaa tcctaatgac ttctaaaaat gtaactaatt      7140
gaatcattat cttacatttta ctgtttaata agcatatttt gaaaatgtat ggctagagtg      7200
tcataataaa atggtatatc tttctttagt aattacaaaa aaaaaaaaaa aaaaaaaaa       7260
```

<210> SEQ ID NO 35
<211> LENGTH: 3665
<212> TYPE: DNA
<213> ORGANISM: Homo sapiens

```
<400> SEQUENCE: 35
ggcttggggc agccgggtag ctcggaggtc gtggcgctgg gggctagcac cagcgctctg      60
tcgggaggcg cagcggttag gtggaccggt cagcggactc accggccagg gcgctcggtg     120
ctggaatttg atattcattg atccgggttt tatccctctt cttttttctt aaacattttt     180
ttttaaaact gtattgtttc tcgttttaat ttattttgc ttgccattcc ccacttgaat      240
cgggccgacg gcttggggag attgctctac ttccccaaat cactgtggat tttggaaacc     300
agcagaaaga ggaaagaggt agcaagagct ccagagagaa gtcgaggaag agagagacgg     360
ggtcagagag agcgcgcggg cgtgcgagca gcgaaagcga caggggcaaa gtgagtgacc     420
tgcttttggg ggtgaccgcc ggagcgcggc gtgagccctc cccccttggga tcccgcagct    480 gaccagtcgc gctgacggac agacagacag acaccgcccc cagccccagc taccacctcc    540
tccccggccg gcggcggaca gtggacgcgg cggcgagccg cgggcagggg ccggagcccg    600
cgcccggagg cggggtggag ggggtcgggg ctcgcggcgt cgcactgaaa cttttcgtcc    660
aacttctggg ctgttctcgc ttcggaggag ccgtggtccg cgcggggga gccgagccga     720 gcggagccgc gagaagtgct agctcggcc gggaggagcc gcagccggag gagggggagg    780
aggaagaaga gaaggaagag gagaggggggc cgcagtggcg actcggcgct cggaagccgg   840
gctcatggac gggtgaggcg gcggtgtgcg cagacagtgc tccagccgcg cgcgctcccc    900
aggccctggc ccgggcctcg ggccggggag gaagagtagc tcgccgaggc gccgaggaga   960
gcgggccgcc ccacagcccg agccggagag ggagcgcgag ccgcgccggc cccggtcggg   1020
cctccgaaac catgaacttt ctgctgtctt gggtgcattg gagccttgcc ttgctgctct    1080
acctccacca tgccaagtgg tcccaggctg cacccatggc agaaggagga gggcagaatc   1140
atcacgaagt ggtgaagttc atggatgtct atcagcgcag ctactgccat ccaatcgaga   1200
ccctggtgga catcttccag gagtaccctg atgagatcga gtacatcttc aagccatcct   1260
gtgtgcccct gatgcgatgc ggggggctgct gcaatgacga gggcctggag tgtgtgccca   1320
ctgaggagtc caacatcacc atgcagatta tgcggatcaa acctcaccaa ggccagcaca    1380
taggagagat gagcttccta cagcacaaca aatgtgaatg cagaccaaag aaagatagag    1440
caagacaaga aaaaaatca gttcgaggaa agggaagggg gcaaaaacga aagcgcaaga    1500
aatcccggta taagtcctgg agcgtgtacg ttggtgcccg ctgctgtcta atgccctgga    1560
gcctccctgg cccccatccc tgtgggcctt gctcagagcg gagaaagcat tgtttgtac     1620 aagatccgca gacgtgtaaa tgttcctgca aaaacacaga ctcgcgttgc aaggcgaggc   1680
agcttgagtt aaacgaacgt acttgcagat gtgacaagcc gaggcggtga gccgggcagg   1740
aggaaggagc ctccctcagg gtttcgggaa ccagatctct caccaggaaa gactgataca    1800
gaacgatcga tacagaaacc acgctgccgc caccacacca tcaccatcga cagaacagtc    1860
cttaatccag aaacctgaaa tgaaggaaga ggagactctg cgcagagcac tttgggtccg    1920
gagggcgaga ctccggcgga agcattcccg ggcgggtgac ccagcacggt ccctcttgga    1980
attggattcg ccattttatt tttccttgctg ctaaatcacc gagcccggaa gattagagag   2040
ttttatttct gggattcctg tagacacacc cacccacata catacattta tatatatata    2100
tattatatat ataaaaaat aaatatctct attttatata tataaaatat atatattctt     2160
tttttaaatt aacagtgcta atgttattgg tgtcttcact ggatgtattt gactgctgtg    2220
gacttgagtt ggagggaa tgttcccact cagatcctga cagggaagag gaggagatga      2280
gagactctgg catgatcttt tttttgtccc acttggtggg gccagggtcc tctcccctgc    2340
```

```
ccaggaatgt gcaaggccag ggcatgggggg caaatatgac ccagttttgg gaacaccgac     2400
aaacccagcc ctggcgctga gcctctctac cccaggtcag acggacagaa agacagatca     2460
caggtacagg gatgaggaca ccggctctga ccaggagttt ggggagcttc aggacattgc     2520
tgtgctttgg ggattccctc cacatgctgc acgcgcatct cgcccccagg ggcactgcct     2580
ggaagattca ggagcctggg cggccttcgc ttactctcac ctgcttctga gttgcccagg     2640
agaccactgg cagatgtccc ggcgaagaga agagacacat tgttggaaga agcagcccat     2700
gacagctccc cttcctggga ctcgccctca tcctcttcct gctccccttc ctggggtgca     2760
gcctaaaagg acctatgtcc tcacaccatt gaaaccacta gttctgtccc cccaggagac     2820
ctggttgtgt gtgtgtgagt ggttgacctt cctccatccc ctggtccttc ccttcccttc     2880
ccgaggcaca gagagacagg gcaggatcca cgtgcccatt gtggaggcag agaaaagaga     2940
aagtgtttta tatacggtac ttatttaata tcccttttta attagaaatt aaaacagtta     3000
atttaattaa agagtagggt ttttttttcag tattcttggt taatatttaa tttcaactat     3060
ttatgagatg tatcttttgc tctctcttgc tctcttattt gtaccggttt ttgtatataa     3120
aattcatgtt tccaatctct ctctccctga tcggtgacag tcactagctt atcttgaaca     3180
gatatttaat tttgctaaca ctcagctctg ccctccccga tccctggct ccccagcaca      3240 cattcctttg aaataaggtt tcaatataca tctacatact atatatatat ttggcaactt     3300
gtatttgtgt gtatatatat atatatatgt ttatgtatat atgtgattct gataaaatag     3360
acattgctat tctgtttttt atatgtaaaa acaaaacaag aaaaaataga gaattctaca     3420
tactaaatct ctctccttttt ttaatttttaa tatttgttat catttatttta ttggtgctac     3480 tgtttatccg taataattgt ggggaaaaga tattaacatc acgtctttgt ctctagtgca     3540 gttttttcgag atattccgta gtacatattt atttttaaac aacgacaaag aaatacagat     3600
atatcttaaa aaaaaaaaag cattttgtat taaagaattt aattctgatc tcaaaaaaaa     3660
aaaaa                                                                  3665

<210> SEQ ID NO 36
<211> LENGTH: 3614
<212> TYPE: DNA
<213> ORGANISM: Homo sapiens

<400> SEQUENCE: 36
ggcttggggc agccgggtag ctcggaggtc gtggcgctgg gggctagcac cagcgctctg       60
tcgggaggcg cagcggttag gtggaccggt cagcggactc accggccagg cgctcggtg      120 ctggaatttg atattcattg atccgggttt tatccctctt cttttttctt aaacattttt     180
ttttaaaact gtattgtttc tcgttttaat ttatttttgc ttgccattcc ccacttgaat     240
cgggccgacg gcttggggag attgctctac ttccccaaat cactgtggat tttggaaacc     300
agcagaaaga ggaaagaggt agcaagagct ccagagagaa gtcgaggaag agagagacgg     360
ggtcagagag agcgcgcggg cgtgcgagca gcgaaagcga caggggcaaa gtgagtgacc     420
tgctttgggg ggtgaccgcc ggagcgcggc gtgagccctc cccttgggga tcccgcagct     480
gaccagtcgc gctgacggac agacagacag acaccgcccc cagcccagc taccacctcc      540 tccccggccg cgcgcggaca gtggacgcgg cggcgagccg cggcagggg ccggagcccg      600 cgcccggagg cggggtggag ggggtcgggg ctcgcggcgt cgcactgaaa cttttcgtcc     660
aacttctggg ctgttctcgc ttcggaggag ccgtggtccg cgcggggggaa gccgagccga     720 gcggagccgc gagaagtgct agctcgggcc gggaggagcc gcagccggag gaggggggagg     780
```

| | |
|---|---|
| aggaagaaga gaaggaagag gagaggggc cgcagtggcg actcggcgct cggaagccgg | 840 |
| gctcatggac gggtgaggcg gcggtgtgcg cagacagtgc tccagccgcg cgcgctcccc | 900 |
| aggccctggc ccgggcctcg ggccgggag gaagagtagc tcgccgaggc gccgaggaga | 960 |
| gcgggccgcc ccacagcccg agccggagag ggagcgcgag ccgcgccggc cccggtcggg | 1020 |
| cctccgaaac catgaacttt ctgctgtctt gggtgcattg gagccttgcc ttgctgctct | 1080 |
| acctccacca tgccaagtgg tcccaggctg cacccatggc agaaggagga gggcagaatc | 1140 |
| atcacgaagt ggtgaagttc atggatgtct atcagcgcag ctactgccat ccaatcgaga | 1200 |
| ccctggtgga catcttccag gagtaccctg atgagatcga gtacatcttc aagccatcct | 1260 |
| gtgtgcccct gatgcgatgc ggggctgct gcaatgacga gggcctggag tgtgtgccca | 1320 |
| ctgaggagtc caacatcacc atgcagatta tgcggatcaa acctcaccaa ggccagcaca | 1380 |
| taggagagat gagcttccta cagcacaaca atgtgaatg cagaccaaag aaagatagag | 1440 |
| caagacaaga aaaaaaatca gttcgaggaa agggaaaggg gcaaaaacga aagcgcaaga | 1500 |
| aatcccggta taagtcctgg agcgttccct gtgggccttg ctcagagcgg agaaagcatt | 1560 |
| tgtttgtaca agatccgcag acgtgtaaat gttcctgcaa aaacacagac tcgcgttgca | 1620 |
| aggcgaggca gcttgagtta acgaacgta cttgcagatg tgacaagccg aggcggtgag | 1680 |
| ccgggcagga ggaaggagcc tccctcaggg tttcgggaac cagatctctc accaggaaag | 1740 |
| actgatacag aacgatcgat acagaaacca cgctgccgcc accacaccat caccatcgac | 1800 |
| agaacagtcc ttaatccaga aacctgaaat gaaggaagag gagactctgc gcagagcact | 1860 |
| ttgggtccgg agggcgagac tccggcggaa gcattcccgg gcgggtgacc cagcacggtc | 1920 |
| cctcttggaa ttggattcgc cattttattt ttcttgctgc taaatcaccg agcccggaag | 1980 |
| attagagagt tttatttctg ggattcctgt agacacaccc acccacatac atacatttat | 2040 |
| atatatatat attatatata tataaaaata aatatctcta ttttatatat ataaaatata | 2100 |
| tatattcttt ttttaaatta acagtgctaa tgttattggt gtcttcactg gatgtatttg | 2160 |
| actgctgtgg acttgagttg ggaggggaat gttcccactc agatcctgac agggaagagg | 2220 |
| aggagatgag agactctggc atgatctttt ttttgtccca cttggtgggg ccagggtcct | 2280 |
| ctcccctgcc caggaatgtg caaggccagg gcatgggggc aaatatgacc cagttttggg | 2340 |
| aacaccgaca aacccagccc tggcgctgag cctctctacc ccaggtcaga cggacagaaa | 2400 |
| gacagatcac aggtacaggg atgaggacac cggctctgac caggagtttg gggagcttca | 2460 |
| ggacattgct gtgctttggg gattccctcc acatgctgca cgcgcatctc gcccccaggg | 2520 |
| gcactgcctg gaagattcag gagcctgggc ggccttcgct tactctcacc tgcttctgag | 2580 |
| ttgcccagga gaccactggc agatgtcccg gcgaagagaa gagacacatt gttggaagaa | 2640 |
| gcagcccatg acagctcccc ttcctgggac tcgccctcat cctcttcctg ctcccttcc | 2700 |
| tggggtgcag cctaaaagga cctatgtcct cacaccattg aaaccactag ttctgtcccc | 2760 |
| ccaggagacc tggttgtgtg tgtgtgagtg gttgaccttc ctccatcccc tggtccttcc | 2820 |
| cttcccttcc cgaggcacag agagacaggg caggatccac gtgcccattg tggaggcaga | 2880 |
| gaaaagagaa agtgttttat atacggtact tatttaatat ccctttttaa ttagaaatta | 2940 |
| aaacagttaa tttaattaaa gagtagggtt ttttttcagt attcttggtt aatatttaat | 3000 |
| ttcaactatt tatgagatgt atcttttgct ctctcttgct ctcttatttg taccggtttt | 3060 |
| tgtatataaa attcatgttt ccaatctctc tctccctgat cggtgacagt cactagctta | 3120 |
| tcttgaacag atatttaatt ttgctaacac tcagctctgc cctccccgat cccctggctc | 3180 |

| | |
|---|---:|
| cccagcacac attcctttga ataaggtttt caatatacat ctacatacta tatatatatt | 3240 |
| tggcaacttg tatttgtgtg tatatatata tatatatgtt tatgtatata tgtgattctg | 3300 |
| ataaaataga cattgctatt ctgttttttta tatgtaaaaa caaaacaaga aaaaatagag | 3360 |
| aattctacat actaaatctc tctccttttt taattttaat atttgttatc atttatttat | 3420 |
| tggtgctact gtttatccgt aataattgtg gggaaaagat attaacatca cgtctttgtc | 3480 |
| tctagtgcag ttttttcgaga tattccgtag tacatattta ttttttaaaca acgacaaaga | 3540 |
| aatacagata tatcttaaaa aaaaaaaagc attttgtatt aaagaattta attctgatct | 3600 |
| caaaaaaaaa aaaa | 3614 |

<210> SEQ ID NO 37
<211> LENGTH: 3596
<212> TYPE: DNA
<213> ORGANISM: Homo sapiens

<400> SEQUENCE: 37

| | |
|---|---:|
| ggcttggggc agccgggtag ctcggaggtc gtggcgctgg gggctagcac cagcgctctg | 60 |
| tcgggaggcg cagcggttag gtggaccggt cagcggactc accggccagg gcgctcggtg | 120 |
| ctggaatttg atattcattg atccgggttt tatccctctt cttttttctt aaacattttt | 180 |
| ttttaaaact gtattgtttc tcgttttaat ttattttgc ttgccattcc ccacttgaat | 240 |
| cgggccgacg gcttggggag attgctctac ttccccaaat cactgtggat tttggaaacc | 300 |
| agcagaaaga ggaaagaggt agcaagagct ccagagagaa gtcgaggaag agagagacgg | 360 |
| ggtcagagag agcgcgcggg cgtgcgagca gcgaaagcga caggggcaaa gtgagtgacc | 420 |
| tgcttttggg ggtgaccgcc ggagcgcggc gtgagccctc cccctggga tcccgcagct | 480 |
| gaccagtcgc gctgacggac agacagacag acaccgcccc cagccccagc taccacctcc | 540 |
| tccccggccg cgcggcggaca gtggacgcgc cggcgagccg cgggcagggg ccggagcccg | 600 |
| cgcccggagg cggggtggag ggggtcgggg ctcgcggcgt cgcactgaaa ctttttcgtcc | 660 |
| aacttctggg ctgttctcgc ttcggaggag ccgtggtccg cgcggggggaa gccgagccga | 720 |
| gcggagccga gagaagtgct agctcgggcc gggaggagcc gcagccggag gaggggggagg | 780 |
| aggaagaaga gaaggaagag gagagggggc cgcagtggcg actcggcgct cggaagccgg | 840 |
| gctcatggac gggtgaggcg gcggtgtgcg cagacagtgc tccagccgcg cgcgctcccc | 900 |
| aggccctggc ccgggcctcg ggccggggag gaagagtagc tcgccgaggc gccgaggaga | 960 |
| gcgggccgcc ccacagcccg agccggagag ggagcgcgag ccgcgccggc cccggtcggg | 1020 |
| cctccgaaac catgaacttt ctgctgtctt gggtgcattg gagccttgcc ttgctgctct | 1080 |
| acctccacca tgccaagtgg tcccaggctg cacccatggc agaaggagga gggcagaatc | 1140 |
| atcacgaagt ggtgaagttc atggatgtct atcagcgcag ctactgccat ccaatcgaga | 1200 |
| ccctggtgga catcttccag gagtaccctg atgagatcga gtacatcttc aagccatcct | 1260 |
| gtgtgcccct gatgcgatgc ggggggctgct gcaatgacga gggcctggag tgtgtgccca | 1320 |
| ctgaggagtc caacatcacc atgcagatta tgcggatcaa acctcaccaa ggccagcaca | 1380 |
| taggagagat gagcttccta cagcacaaca aatgtgaatg cagaccaaag aaagatagag | 1440 |
| caagacaaga aaaaaaatca gttcgaggaa agggaaaggg gcaaaaacga aagcgcaaga | 1500 |
| aatcccgtcc ctgtgggcct tgctcagagc ggagaaagca tttgtttgta caagatccgc | 1560 |
| agacgtgtaa atgttcctgc aaaaacacag actcgcgttg caaggcgagg cagcttgagt | 1620 |
| taaacgaacg tacttgcaga tgtgacaagc cgaggcggtg agccgggcag gaggaaggag | 1680 |

| | | | | | |
|---|---|---|---|---|---|
| cctccctcag | ggtttcggga | accagatctc | tcaccaggaa | agactgatac | agaacgatcg | 1740 |
| atacagaaac | cacgctgccg | ccaccacacc | atcaccatcg | acagaacagt | ccttaatcca | 1800 |
| gaaacctgaa | atgaaggaag | aggagactct | gcgcagagca | ctttgggtcc | ggagggcgag | 1860 |
| actccggcgg | aagcattccc | gggcgggtga | cccagcacgg | tccctcttgg | aattggattc | 1920 |
| gccattttat | ttttcttgct | gctaaatcac | cgagcccgga | agattagaga | gttttatttc | 1980 |
| tgggattcct | gtagacacac | ccacccacat | acatacattt | atatatatat | atattatata | 2040 |
| tatataaaaa | taaatatctc | tattttatat | atataaaata | tatatattct | ttttttaaat | 2100 |
| taacagtgct | aatgttattg | gtgtcttcac | tggatgtatt | tgactgctgt | ggacttgagt | 2160 |
| tgggagggga | atgttcccac | tcagatcctg | acagggaaga | ggaggagatg | agagactctg | 2220 |
| gcatgatctt | ttttttgtcc | cacttggtgg | ggccagggtc | ctctcccctg | cccaggaatg | 2280 |
| tgcaaggcca | gggcatgggg | gcaaatatga | cccagttttg | ggaacaccga | caaacccagc | 2340 |
| cctggcgctg | agcctctcta | ccccaggtca | gacggacaga | aagacagatc | acaggtacag | 2400 |
| ggatgaggac | accggctctg | accaggagtt | tggggagctt | caggacattg | ctgtgctttg | 2460 |
| gggattccct | ccacatgctg | cacgcgcatc | tcgcccccag | gggcactgcc | tggaagattc | 2520 |
| aggagcctgg | gcggccttcg | cttactctca | cctgcttctg | agttgcccag | agaccactg | 2580 |
| gcagatgtcc | cggcgaagag | aagagacaca | ttgttggaag | aagcagccca | tgacagctcc | 2640 |
| ccttcctggg | actcgccctc | atcctcttcc | tgctcccctt | cctggggtgc | agcctaaaag | 2700 |
| gacctatgtc | ctcacaccat | tgaaaccact | agttctgtcc | ccccaggaga | cctggttgtg | 2760 |
| tgtgtgtgag | tggttgacct | tcctccatcc | cctggtcctt | cccttccctt | cccgaggcac | 2820 |
| agagagacag | ggcaggatcc | acgtgcccat | tgtggaggca | gagaaaagag | aaagtgtttt | 2880 |
| atatacggta | cttatttaat | atccctttt | aattagaaat | taaaacagtt | aatttaatta | 2940 |
| aagagtaggg | ttttttttca | gtattcttgg | ttaatattta | atttcaacta | tttatgagat | 3000 |
| gtatcttttg | ctctctcttg | ctctcttatt | tgtaccggtt | tttgtatata | aaattcatgt | 3060 |
| ttccaatctc | tctctccctg | atcggtgaca | gtcactagct | tatcttgaac | agatatttaa | 3120 |
| ttttgctaac | actcagctct | gccctccccg | atccctggc | tccccagcac | acattccttt | 3180 |
| gaaataaggt | ttcaatatac | atctacatac | tatatatata | tttggcaact | tgtatttgtg | 3240 |
| tgtatatata | tatatatatg | tttatgtata | tatgtgattc | tgataaaata | gacattgcta | 3300 |
| ttctgttttt | tatatgtaaa | aacaaaacaa | gaaaaaatag | agaattctac | atactaaatc | 3360 |
| tctctccttt | tttaatttta | atatttgtta | tcatttattt | attggtgcta | ctgtttatcc | 3420 |
| gtaataattg | tggggaaaag | atattaacat | cacgtctttg | tctctagtgc | agtttttcga | 3480 |
| gatattccgt | agtacatatt | tattttaaa | caacgacaaa | gaaatacaga | tatatcttaa | 3540 |
| aaaaaaaaaa | gcattttgta | ttaaagaatt | taattctgat | ctcaaaaaaa | aaaaaa | 3596 |

<210> SEQ ID NO 38
<211> LENGTH: 3542
<212> TYPE: DNA
<213> ORGANISM: Homo sapiens

<400> SEQUENCE: 38

| | | | | | |
|---|---|---|---|---|---|
| ggcttggggc | agccgggtag | ctcggaggtc | gtggcgctgg | gggctagcac | cagcgctctg | 60 |
| tcgggaggcg | cagcggttag | gtggaccggt | cagcggactc | accggccagg | gcgctcggtg | 120 |
| ctggaatttg | atattcattg | atccgggttt | tatccctctt | ctttttttctt | aaacattttt | 180 |
| ttttaaaact | gtattgtttc | tcgttttaat | ttattttgc | ttgccattcc | ccacttgaat | 240 |

```
                                                                   -continued cggggccgacg gcttggggag attgctctac ttccccaaat cactgtggat tttggaaacc   300
agcagaaaga ggaaagaggt agcaagagct ccagagagaa gtcgaggaag agagagacgg   360
ggtcagagag agcgcgcggg cgtgcgagca gcgaaagcga caggggcaaa gtgagtgacc   420
tgcttttggg ggtgaccgcc ggagcgcggc gtgagccctc ccccttggga tcccgcagct   480
gaccagtcgc gctgacggac agacagacag acaccgcccc cagccccagc taccacctcc   540
tccccggccg gcggcggaca gtggacgcgg cggcgagccg cgggcagggg ccggagcccg   600
cgcccggagg cggggtggag ggggtcgggg ctcgcggcgt cgcactgaaa cttttcgtcc   660
aacttctggg ctgttctcgc ttcggaggag ccgtggtccg cgcggggaa gccgagccga   720 gcggagccgc gagaagtgct agctcgggcc gggaggagcc gcagccggag gaggggagg   780 aggaagaaga gaaggaagag gagaggggc cgcagtggcg actcggcgct cggaagccgg   840
gctcatggac gggtgaggcg gcggtgtgcg cagacagtgc tccagccgcg cgcgctcccc   900
aggccctggc ccgggcctcg ggccggggag gaagagtagc tcgccgaggc gccgaggaga   960
gcgggccgcc ccacagcccg agccggagag ggagcgcgag ccgcgccggc cccggtcggg  1020
cctccgaaac catgaacttt ctgctgtctt gggtgcattg gagccttgcc ttgctgctct  1080
acctccacca tgccaagtgg tcccaggctg cacccatggc agaaggagga gggcagaatc  1140
atcacgaagt ggtgaagttc atggatgtct atcagcgcag ctactgccat ccaatcgaga  1200
ccctggtgga catcttccag gagtaccctg atgagatcga gtacatcttc aagccatcct  1260 gtgtgccct gatgcgatgc ggggctgct gcaatgacga gggcctggag tgtgtgccca  1320
ctgaggagtc caacatcacc atgcagatta tgcggatcaa cctccaccaa ggccagcaca  1380
taggagagat gagcttccta cagcacaaca aatgtgaatg cagaccaaag aaagatagag  1440
caagacaaga aaatccctgt gggccttgct cagagcggaa aaagcatttg tttgtacaag  1500
atccgcagac gtgtaaatgt tcctgcaaaa acacagactc gcgttgcaag gcgaggcagc  1560
ttgagttaaa cgaacgtact tgcagatgtg acaagccgag gcggtgagcc gggcaggagg  1620
aaggagcctc cctcagggtt tcgggaacca gatctctcac caggaaagac tgatacagaa  1680
cgatcgatac agaaaccacg ctgccgccac cacaccatca ccatcgacag aacagtcctt  1740
aatccagaaa cctgaaatga aggaagagga gactctgcgc agagcacttt gggtccggag  1800
ggcgagactc cggcggaagc attcccgggc gggtgaccca gcacggtccc tcttggaatt  1860
ggattcgcca tttttattttt cttgctgcta aatcaccgag cccggaagat tagagagtttt  1920 tatttctggg attcctgtag acacacccac ccacatacat acatttatat atatatatat  1980
tatatatata taaaaataaa tatctctatt ttatatatat aaaatatata tattctttt  2040 ttaaattaac agtgctaatg ttattggtgt cttcactgga tgtatttgac tgctgtggac  2100
ttgagttggg aggggaatgt tcccactcag atcctgacag ggaagaggag gagatgagag  2160
actctggcat gatctttttt ttgtcccact tggtggggcc agggtcctct cccctgccca  2220
ggaatgtgca aggccagggc atgggggcaa atatgaccca gttttgggaa caccgacaaa  2280
cccagccctg gcgctgagcc tctctacccc aggtcagacg gacagaaaga cagatcacag  2340
gtacagggat gaggacaccg gctctgacca ggagtttggg gagcttcagg acattgctgt  2400
gctttgggga ttccctccac atgctgcacg cgcatctcgc ccccagggc actgcctgga  2460 agattcagga gcctgggcgg ccttcgctta ctctcacctg cttctgagtt gcccaggaga  2520
ccactggcag atgtcccggc gaagagaaga gacacattgt tggaagaagc agcccatgac  2580
agctcccctt cctgggactc gccctcatcc tcttcctgct cccccttcctg gggtgcagcc  2640
```

-continued

| | |
|---|---|
| taaaaggacc tatgtcctca caccattgaa accactagtt ctgtcccccc aggagacctg | 2700 |
| gttgtgtgtg tgtgagtggt tgaccttcct ccatcccctg gtccttccct tcccttcccg | 2760 |
| aggcacagag agacagggca ggatccacgt gcccattgtg gaggcagaga aagagaaag | 2820 |
| tgttttatat acggtactta tttaatatcc cttttaatt agaaattaaa acagttaatt | 2880 |
| taattaaaga gtagggtttt ttttcagtat tcttggttaa tatttaattt caactattta | 2940 |
| tgagatgtat cttttgctct ctcttgctct cttatttgta ccggttttg tatataaaat | 3000 |
| tcatgtttcc aatctctctc tccctgatcg gtgacagtca ctagcttatc ttgaacagat | 3060 |
| atttaatttt gctaacactc agctctgccc tccccgatcc cctggctccc cagcacacat | 3120 |
| tcctttgaaa taaggtttca atatacatct acatactata tatatatttg gcaacttgta | 3180 |
| tttgtgtgta tatatatata tatatgttta tgtatatatg tgattctgat aaaatagaca | 3240 |
| ttgctattct gttttttata tgtaaaaaca aaacaagaaa aaatagagaa ttctacatac | 3300 |
| taaatctctc tccttttta attttaatat ttgttatcat ttatttattg gtgctactgt | 3360 |
| ttatccgtaa taattgtggg gaaaagatat taacatcacg tctttgtctc tagtgcagtt | 3420 |
| tttcgagata ttccgtagta catatttatt tttaaacaac gacaaagaaa tacagatata | 3480 |
| tcttaaaaaa aaaaaagcat tttgtattaa agaatttaat tctgatctca aaaaaaaaaa | 3540 |
| aa | 3542 |

<210> SEQ ID NO 39
<211> LENGTH: 3507
<212> TYPE: DNA
<213> ORGANISM: Homo sapiens

<400> SEQUENCE: 39

| | |
|---|---|
| ggcttggggc agccgggtag ctcggaggtc gtggcgctgg gggctagcac cagcgctctg | 60 |
| tcgggaggcg cagcggttag gtggaccggt cagcggactc accggccagg gcgctcggtg | 120 |
| ctggaatttg atattcattg atccgggttt tatccctctt cttttttctt aaacattttt | 180 |
| ttttaaaact gtattgtttc tcgttttaat ttattttttgc ttgccattcc ccacttgaat | 240 |
| cgggccgacg gcttgggag attgctctac ttccccaaat cactgtggat tttggaaacc | 300 |
| agcagaaaga ggaaagaggt agcaagagct ccagagagaa gtcgaggaag agagagacgg | 360 |
| ggtcagagag agcgcgcggg cgtgcgagca gcgaaagcga caggggcaaa gtgagtgacc | 420 |
| tgcttttggg ggtgaccgcc ggagcgcggc gtgagccctc ccccttggga tcccgcagct | 480 |
| gaccagtcgc gctgacggac agacagacag acaccgcccc cagccccagc taccacctcc | 540 |
| tccccggccg gcggcggaca gtggacgcgg cggcgagccg cgggcagggg ccggagcccg | 600 |
| cgcccggagg cggggtggag ggggtcgggg ctcgcggcgt cgcactgaaa cttttcgtcc | 660 |
| aacttctggg ctgttctcgc ttcggaggag ccgtggtccg cgcggggaa gccgagccga | 720 |
| gcggagccgc gagaagtgct agctcgggcc gggaggagcc gcagccggag gaggggagg | 780 |
| aggaagaaga gaaggaagag gagagggggc cgcagtggcg actcggcgct cggaagccgg | 840 |
| gctcatggac gggtgaggcg gcggtgtgcg cagacagtgc tccagccgcg cgcgctcccc | 900 |
| aggccctggc ccgggcctcg ggccggggag gaagagtagc tcgccgaggc gccgaggaga | 960 |
| gcgggccgcc ccacagcccg agccggagag ggagcgcgag ccgcgccggc cccggtcggg | 1020 |
| cctccgaaac catgaacttt ctgctgtctt gggtgcattg gagccttgcc ttgctgctct | 1080 |
| acctccacca tgccaagtgg tcccaggctg cacccatggc agaaggagga gggcagaatc | 1140 |
| atcacgaagt ggtgaagttc atggatgtct atcagcgcag ctactgccat ccaatcgaga | 1200 |

```
cctggtgga catcttccag gagtaccctg atgagatcga gtacatcttc aagccatcct    1260
gtgtgcccct gatgcgatgc gggggctgct gcaatgacga gggcctggag tgtgtgccca    1320
ctgaggagtc caacatcacc atgcagatta tgcggatcaa acctcaccaa ggccagcaca    1380
taggagagat gagcttccta cagcacaaca aatgtgaatg cagaccaaag aaagatagag    1440
caagacaaga aaatccctgt gggccttgct cagagcggag aaagcatttg tttgtacaag    1500
atccgcagac gtgtaaatgt tcctgcaaaa acacagactc gcgttgcaag atgtgacaag    1560
ccgaggcggt gagccgggca ggaggaagga gcctccctca gggtttcggg aaccagatct    1620
ctcaccagga aagactgata cagaacgatc gatacagaaa ccacgctgcc gccaccacac    1680
catcaccatc gacagaacag tccttaatcc agaaacctga atgaaggaa gaggagactc    1740 tgcgcagagc actttgggtc cggagggcga gactccggcg gaagcattcc cgggcgggtg    1800
acccagcacg gtccctcttg gaattggatt cgccatttta ttttcttgc tgctaaatca    1860 ccgagcccgg aagattagag agttttattt ctgggattcc tgtagacaca cccacccaca    1920
tacatacatt tatatatata tatattatat atatataaaa ataaatatct ctattttata    1980
tatataaaat atatatattc ttttttttaaa ttaacagtgc taatgttatt ggtgtcttca    2040
ctggatgtat ttgactgctg tggacttgag ttgggagggg aatgttccca ctcagatcct    2100
gacagggaag aggaggagat gagagactct ggcatgatct ttttttttgtc ccacttggtg    2160 gggccagggt cctctcccct gcccaggaat gtgcaaggcc agggcatggg ggcaaatatg    2220
acccagtttt gggaacaccg acaaacccag ccctggcgct gagcctctct accccaggtc    2280
agacggacag aaagacagat cacaggtaca gggatgagga caccggctct gaccaggagt    2340
ttggggagct tcaggacatt gctgtgcttt ggggattccc tccacatgct gcacgcgcat    2400
ctcgccccca ggggcactgc ctggaagatt caggagcctg ggcggccttc gcttactctc    2460
acctgcttct gagttgccca ggagaccact ggcagatgtc ccggcgaaga aagagacac    2520 attgttggaa gaagcagccc atgacagctc cccttcctgg gactcgccct catcctcttc    2580
ctgctcccct tcctgggggtg cagcctaaaa ggacctatgt cctcacacca ttgaaaccac    2640
tagttctgtc cccccaggag acctggttgt gtgtgtgtga gtggttgacc ttcctccatc    2700
ccctggtcct tcccttccct tcccgaggca cagagagaca gggcaggatc cacgtgccca    2760
ttgtggaggc agagaaaaga gaaagtgttt tatatacggt acttatttaa tatccctttt    2820
taattagaaa ttaaaacagt taatttaatt aaagagtagg gttttttttc agtattcttg    2880
gttaatattt aatttcaact atttatgaga tgtatctttt gctctctctt gctctcttat    2940
ttgtaccggt ttttgtatat aaaattcatg tttccaatct ctctctccct gatcggtgac    3000
agtcactagc ttatcttgaa cagatattta attttgctaa cactcagctc tgccctcccc    3060
gatcccctgg ctccccagca cacattcctt tgaaataagg tttcaatata catctacata    3120
ctatatatat atttggcaac ttgtatttgt gtgtatatat atatatatat gtttatgtat    3180
atatgtgatt ctgataaaat agacattgct attctgtttt ttatatgtaa aaacaaaaca    3240
agaaaaaata gagaattcta catactaaat ctctctcctt ttttaatttt aatatttgtt    3300
atcatttatt tattggtgct actgtttatc cgtaataatt gtggggaaaa gatattaaca    3360
tcacgtcttt gtctctagtg cagttttttcg agatattccg tagtacatat ttattttaa    3420 acaacgacaa agaaatacag atatatctta aaaaaaaaaa agcattttgt attaaagaat    3480
ttaattctga tctcaaaaaa aaaaaaa                                        3507
```

<210> SEQ ID NO 40

<211> LENGTH: 3410
<212> TYPE: DNA
<213> ORGANISM: Homo sapiens

<400> SEQUENCE: 40

```
ggcttggggc agccgggtag ctcggaggtc gtggcgctgg gggctagcac cagcgctctg      60
tcgggaggcg cagcggttag gtggaccggt cagcggactc accggccagg gcgctcggtg     120
ctggaatttg atattcattg atccgggttt tatccctctt ctttttttctt aaacattttt    180
ttttaaaact gtattgtttc tcgttttaat ttattttttgc ttgccattcc ccacttgaat    240
cgggccgacg gcttggggag attgctctac ttccccaaat cactgtggat tttggaaacc    300
agcagaaaga ggaaagaggt agcaagagct ccagagagaa gtcgaggaag agagagacgg    360
ggtcagagag agcgcgcggg cgtgcgagca gcgaaagcga caggggcaaa gtgagtgacc    420
tgcttttggg ggtgaccgcc ggagcgcggc gtgagccctc ccccttggga tcccgcagct    480
gaccagtcgc gctgacggac agacagacag acaccgcccc cagccccagc taccacctcc    540
tccccggccg gcggcggaca gtggacgcgg cggcgagccg cgggcagggg ccggagcccg    600
cgcccggagg cggggtggag ggggtcgggg ctcgcggcgt cgcactgaaa cttttcgtcc    660
aacttctggg ctgttctcgc ttcggaggag ccgtggtccg cgcggggggaa gccgagccga    720
gcggagccgc gagaagtgct agctcgggcc gggaggagcc gcagccggag gaggggggagg    780
aggaagaaga gaaggaagag gagaggggggc cgcagtggcg actcggcgct cggaagccgg    840
gctcatggac gggtgaggcg gcggtgtgcg cagacagtgc tccagccgcg cgcgctcccc    900
aggccctggc ccgggcctcg ggccggggag gaagagtagc tcgccgaggc gccgaggaga    960
gcggccgcc ccacagcccg agccggagag ggagcgcgag ccgcgccggc cccggtcggg   1020
cctccgaaac catgaacttt ctgctgtctt gggtgcattg gagccttgcc ttgctgctct   1080
acctccacca tgccaagtgg tcccaggctg cacccatggc agaaggagga gggcagaatc   1140
atcacgaagt ggtgaagttc atggatgtct atcagcgcag ctactgccat ccaatcgaga   1200
ccctggtgga catcttccag gagtaccctg atgagatcga gtacatcttc aagccatcct   1260
gtgtgccccct gatgcgatgc ggggggctgct gcaatgacga gggcctggag tgtgtgccca   1320
ctgaggagtc caacatcacc atgcagatta tgcggatcaa acctcaccaa ggccagcaca   1380
taggagagat gagcttccta cagcacaaca atgtgaatg cagaccaaag aaagatagag   1440
caagacaaga aaatgtgac aagccgaggc ggtgagccgg gcaggaggaa ggagcctccc   1500
tcagggtttc gggaaccaga tctctcacca ggaaagactg atacagaacg atcgatacag   1560
aaaccacgct gccgccacca ccatcacc atcgacagaa cagtccttaa tccagaaacc   1620
tgaaatgaag gaagaggaga ctctgcgcag agcactttgg gtccggaggg cgagactccg   1680
gcggaagcat tcccgggcgg gtgacccagc acggtccctc ttggaattgg attcgccatt   1740
ttatttttct tgctgctaaa tcaccgagcc cggaagatta gagagtttta tttctgggat   1800
tcctgtagac acacccaccc acatacatac atttatatat atatatatta tatatatata   1860
aaaataaata tctctatttt atatatataa aatatatata ttcttttttt aaattaacag   1920
tgctaatgtt attggtgtct tcactggatg tatttgactg ctgtggactt gagttgggag   1980
gggaatgttc ccactcagat cctgacaggg aagaggagga gatgagagac tctggcatga   2040
tcttttttttt gtcccacttg gtggggccag ggtcctctcc cctgcccagg aatgtgcaag   2100
gccagggcat gggggcaaat atgacccagt tttgggaaca ccgacaaacc cagccctggc   2160
gctgagcctc tctaccccag gtcagacgga cagaaagaca gatcacaggt acagggatga   2220
```

```
ggacaccggc tctgaccagg agtttgggga gcttcaggac attgctgtgc tttggggatt    2280
ccctccacat gctgcacgcg catctcgccc ccaggggcac tgcctggaag attcaggagc    2340
ctgggcggcc ttcgcttact ctcacctgct tctgagttgc ccaggagacc actggcagat    2400
gtcccggcga agagaagaga cacattgttg gaagaagcag cccatgacag ctccccttcc    2460
tgggactcgc cctcatcctc ttcctgctcc ccttcctggg gtgcagccta aaaggaccta    2520
tgtcctcaca ccattgaaac cactagttct gtcccccccag gagacctggt tgtgtgtgtg    2580
tgagtggttg accttcctcc atccctggt ccttcccttc ccttcccgag gcacagagag     2640
acagggcagg atccacgtgc ccattgtgga ggcagagaaa agagaaagtg ttttatatac    2700
ggtacttatt taatatccct ttttaattag aaattaaaac agttaattta attaaagagt    2760
aggggttttt ttcagtattc ttggttaata tttaatttca actatttatg agatgtatct    2820
tttgctctct cttgctctct tatttgtacc ggttttttgta tataaaattc atgtttccaa    2880
tctctctctc cctgatcggt gacagtcact agcttatctt gaacagatat ttaattttgc    2940
taacactcag ctctgccctc cccgatcccc tggctcccca gcacacattc ctttgaaata    3000
aggtttcaat atacatctac atactatata tatatttggc aacttgtatt tgtgtgtata    3060
tatatatata tatgtttatg tatatatgtg attctgataa aatagacatt gctattctgt    3120
tttttatatg taaaaacaaa acaagaaaaa atagagaatt ctacatacta aatctctctc    3180
cttttttaat tttaatattt gttatcattt atttattggt gctactgttt atccgtaata    3240
attgtgggga aaagatatta acatcacgtc tttgtctcta gtgcagtttt tcgagatatt    3300
ccgtagtaca tatttatttt taaacaacga caaagaaata cagatatatc ttaaaaaaaa    3360
aaaagcattt tgtattaaag aatttaattc tgatctcaaa aaaaaaaaaa               3410
```

<210> SEQ ID NO 41
<211> LENGTH: 3476
<212> TYPE: DNA
<213> ORGANISM: Homo sapiens

<400> SEQUENCE: 41

```
ggcttgggc agccgggtag ctcggaggtc gtggcgctgg gggctagcac cagcgctctg      60
tcgggaggcg cagcggttag gtggaccggt cagcggactc accggccagg gcgctcggtg    120
ctggaatttg atattcattg atcccgggttt tatccctctt ctttttttctt aaacatttttt  180 ttttaaaact gtattgtttc tcgttttaat ttatttttgc ttgccattcc ccacttgaat    240
cgggccgacg gcttggggag attgctctac ttccccaaat cactgtggat tttgaaaacc    300
agcagaaaga ggaaagaggt agcaagagct ccagagagaa gtcgaggaag agagagacgg    360
ggtcagagag agcgcgcggg cgtgcagca gcgaaagcga caggggcaaa gtgagtgacc     420
tgcttttggg ggtgaccgcc ggagcgcggc gtgagccctc ccccttggga tcccgcagct    480
gaccagtcgc gctgacggac agacagacag acaccgcccc cagccccagc taccacctcc    540
tccccggccg gcggcggaca gtggacgcgg cggcgagccg cgggcagggg ccggagcccg    600
cgcccggagg cggggtggag ggggtcgggg ctcgcggcgt cgcactgaaa cttttcgtcc    660
aacttctggg ctgttctcgc ttcggaggag ccgtggtccg cgcggggaa gccgagccga     720 gcggagccgc gagaagtgct agctcggcc gggaggagcc gcagccggag gagggggagg    780
aggaagaaga gaaggaagag gagaggggc cgcagtggcg actcggcgct cggaagccgg    840
gctcatggac gggtgaggcg gcggtgtgcg cagacagtgc tccagccgcg cgcgctcccc    900
aggccctggc ccgggcctcg ggccggggag gaagagtagc tcgccgaggc gccgaggaga    960
```

-continued

```
gcgggccgcc ccacagcccg agccggagag ggagcgcgag ccgcgccggc cccggtcggg   1020
cctccgaaac catgaacttt ctgctgtctt gggtgcattg gagccttgcc ttgctgctct   1080
acctccacca tgccaagtgg tcccaggctg cacccatggc agaaggagga gggcagaatc   1140
atcacgaagt ggtgaagttc atggatgtct atcagcgcag ctactgccat caatcgaga   1200 ccctggtgga catcttccag gagtaccctg atgagatcga gtacatcttc aagccatcct   1260
gtgtgcccct gatgcgatgc gggggctgct gcaatgacga gggcctggag tgtgtgccca   1320
ctgaggagtc caacatcacc atgcagatta tgcggatcaa acctcaccaa ggccagcaca   1380
taggagagat gagcttccta cagcacaaca aatgtgaatg cagaccaaag aaagatagag   1440
caagacaaga aaatccctgt gggccttgct cagagcggag aaagcatttg tttgtacaag   1500
atccgcagac gtgtaaatgt tcctgcaaaa acacagactc gcgttgcaag gcgaggcagc   1560
ttgagttaaa cgaacgtact tgcagatctc tcaccaggaa agactgatac agaacgatcg   1620
atacagaaac cacgctgccg ccaccacacc atcaccatcg acagaacagt ccttaatcca   1680
gaaacctgaa atgaaggaag aggagactct gcgcagagca ctttgggtcc ggagggcgag   1740
actccggcgg aagcattccc gggcgggtga cccagcacgg tccctcttgg aattggattc   1800 gccatttat ttttcttgct gctaaatcac cgagcccgga agattagaga gttttatttc   1860
tgggattcct gtagacacac ccacccacat acatacattt atatatatat atattatata   1920
tatataaaaa taaatatctc tattttatat atataaaata tatatattct tttttaaat    1980 taacagtgct aatgttattg gtgtcttcac tggatgtatt tgactgctgt ggacttgagt   2040
tgggagggga atgttcccac tcagatcctg acagggaaga ggaggagatg agagactctg   2100
gcatgatctt ttttttgtcc cacttggtgg ggccagggtc ctctcccctg cccaggaatg   2160
tgcaaggcca gggcatgggg gcaaatatga cccagttttg gaacaccga caaacccagc    2220 cctggcgctg agcctctcta ccccaggtca gacggacaga agacagatc acaggtacag    2280 ggatgaggac accggctctg accaggagtt tggggagctt caggacattg ctgtgctttg   2340
gggattccct ccacatgctg cacgcgcatc tcgcccccag gggcactgcc tggaagattc   2400
aggagcctgg gcggccttcg cttactctca cctgcttctg agttgcccag agaccactg    2460 gcagatgtcc cggcgaagag aagagacaca ttgttggaag aagcagccca tgacagctcc   2520
ccttcctggg actcgccctc atcctcttcc tgctccccctt cctggggtgc agcctaaaag   2580
gacctatgtc ctcacaccat tgaaaccact agttctgtcc ccccaggaga cctggttgtg    2640
tgtgtgtgag tggttgacct tcctccatcc cctggtcctt cccttccctt cccgaggcac   2700
agagagacag ggcaggatcc acgtgcccat tgtggaggca gagaaaagag aaagtgtttt   2760
atatacggta cttatttaat atccttttt aattagaaat taaaacagtt aatttaatta    2820
aagagtaggg ttttttttca gtattcttgg ttaatattta atttcaacta tttatgagat   2880
gtatcttttg ctctctcttg ctctcttatt tgtaccggtt tttgtatata aaattcatgt   2940
ttccaatctc tctctccctg atcggtgaca gtcactagct tatcttgaac agatatttaa   3000
ttttgctaac actcagctct gccctccccg atccctggc tccccagcac acattccttt    3060
gaaataaggt ttcaatatac atctacatac tatatatata tttggcaact tgtatttgtg    3120
tgtatatata tatatatatg tttatgtata tatgtgattc tgataaaata gacattgcta    3180
ttctgttttt tatatgtaaa aacaaaacaa gaaaaaatag agaattctac atactaaatc    3240
tctctccttt tttaattttta atatttgtta tcatttattt attggtgcta ctgtttatcc   3300
gtaataattg tggggaaaag atattaacat cacgtctttg tctctagtgc agttttcga     3360
```

```
gatattccgt agtacatatt tatttttaaa caacgacaaa gaaatacaga tatatcttaa      3420
aaaaaaaaaa gcattttgta ttaaagaatt taattctgat ctcaaaaaaa aaaaaa          3476
```

<210> SEQ ID NO 42
<211> LENGTH: 21
<212> TYPE: DNA
<213> ORGANISM: Homo sapiens
<220> FEATURE:
<221> NAME/KEY: misc_feature
<222> LOCATION: (0803)..()
<223> OTHER INFORMATION: Starting position within mouse BACE1 cDNA
      (Genbank Accession NM_011792) and corresponding human sequences.
      DNA sequence corresponding to the therapeutic siRNA starting at
      base 0803. The two 5' nucleotides AA are optional in MB0803.

<400> SEQUENCE: 42
aagggtgtgt atgtgcccta c                                                 21

<210> SEQ ID NO 43
<211> LENGTH: 21
<212> TYPE: DNA
<213> ORGANISM: Homo sapiens
<220> FEATURE:
<221> NAME/KEY: misc_feature
<222> LOCATION: (1663)..()
<223> OTHER INFORMATION: Starting position within mouse BACE1 cDNA
      (Genbank Accession NM_011792) and corresponding human sequences.
      DNA sequence corresponding to the therapeutic siRNA starting at
      base 1663. The two 5' nucleotides AA are optional in MB1663.

<400> SEQUENCE: 43
aattggcttt gctgtcagcg c                                                 21

<210> SEQ ID NO 44
<211> LENGTH: 21
<212> TYPE: DNA
<213> ORGANISM: Homo sapiens
<220> FEATURE:
<221> NAME/KEY: misc_feature
<222> LOCATION: (1749)..()
<223> OTHER INFORMATION: Starting position within mouse BACE1 cDNA
      (Genbank Accession NM_011792) and corresponding human sequences.
      DNA sequence corresponding to the therapeutic siRNA starting at
      base 1749. The two 5' nucleotides AA are optional in MB1749.

<400> SEQUENCE: 44
aagactgtgg ctacaacatt c                                                 21

<210> SEQ ID NO 45
<211> LENGTH: 21
<212> TYPE: DNA
<213> ORGANISM: Homo sapiens
<220> FEATURE:
<221> NAME/KEY: misc_feature
<222> LOCATION: (3249)..()
<223> OTHER INFORMATION: Starting position within mouse BACE1 cDNA
      (Genbank Accession NM_011792) and corresponding human sequences.
      DNA sequence corresponding to the therapeutic siRNA starting at
      base 3249. The two 5' nucleotides AA are optional in MB3249.

<400> SEQUENCE: 45
aaggctgcct ggagaaagga t                                                 21

<210> SEQ ID NO 46
<211> LENGTH: 21
<212> TYPE: DNA
<213> ORGANISM: Homo sapiens
<220> FEATURE:
<221> NAME/KEY: misc_feature
<222> LOCATION: (0916)..()

```
<223> OTHER INFORMATION: Starting position within mouse BACE1 cDNA
      (Genbank Accession NM_011792) and corresponding human sequences.
      DNA sequence corresponding to the therapeutic siRNA starting at
      base 0916. The two 5' nucleotides CA are optional in DhMB0918.

<400> SEQUENCE: 46
cactgaatcg gacaagttct t                                            21

<210> SEQ ID NO 47
<211> LENGTH: 21
<212> TYPE: DNA
<213> ORGANISM: Homo sapiens
<220> FEATURE:
<221> NAME/KEY: misc_feature
<222> LOCATION: (1129)..()
<223> OTHER INFORMATION: Starting position within mouse BACE1 cDNA
      (Genbank Accession NM_011792) and corresponding human sequences.
      DNA sequence corresponding to the therapeutic siRNA starting at
      base 1129. The two 5' nucleotides CA are optional in DhMB1131.

<400> SEQUENCE: 47
catgatcatt ggtggtatcg a                                            21

<210> SEQ ID NO 48
<211> LENGTH: 21
<212> TYPE: DNA
<213> ORGANISM: Homo sapiens
<220> FEATURE:
<221> NAME/KEY: misc_feature
<222> LOCATION: (1231)..()
<223> OTHER INFORMATION: Starting position within mouse BACE1 cDNA
      (Genbank Accession NM_011792) and corresponding human sequences.
      DNA sequence corresponding to the therapeutic siRNA starting at
      base 1231. The two 5' nucleotides AA are optional in DhMB1233.

<400> SEQUENCE: 48
catccttcct cagcaatacc t                                            21

<210> SEQ ID NO 49
<211> LENGTH: 21
<212> TYPE: DNA
<213> ORGANISM: Homo sapiens
<220> FEATURE:
<221> NAME/KEY: misc_feature
<222> LOCATION: (0683)..()
<223> OTHER INFORMATION: Starting position within mouse BACE1 cDNA
      (Genbank Accession NM_011792) and corresponding human sequences.
      DNA sequence corresponding to the therapeutic siRNA starting at
      base 0683. The two 5' nucleotides CA are optional in SEC0683.

<400> SEQUENCE: 49
cagacgctca acatcctggt g                                            21

<210> SEQ ID NO 50
<211> LENGTH: 19
<212> TYPE: DNA
<213> ORGANISM: Homo sapiens

<400> SEQUENCE: 50
ctacgaacct gaagcctaa                                               19

<210> SEQ ID NO 51
<211> LENGTH: 19
<212> TYPE: DNA
<213> ORGANISM: Homo sapiens

<400> SEQUENCE: 51
tcaagactac gaacctgaa                                               19
```

```
<210> SEQ ID NO 52
<211> LENGTH: 19
<212> TYPE: DNA
<213> ORGANISM: Homo sapiens

<400> SEQUENCE: 52
cattagccat ggatgtatt                                               19

<210> SEQ ID NO 53
<211> LENGTH: 19
<212> TYPE: DNA
<213> ORGANISM: Homo sapiens

<400> SEQUENCE: 53
acgaacctga agcctaaga                                               19

<210> SEQ ID NO 54
<211> LENGTH: 19
<212> TYPE: DNA
<213> ORGANISM: Homo sapiens

<400> SEQUENCE: 54
gtacaagtgc tcagttcca                                               19

<210> SEQ ID NO 55
<211> LENGTH: 19
<212> TYPE: DNA
<213> ORGANISM: Homo sapiens

<400> SEQUENCE: 55
gcttcaatct acgatgtta                                               19

<210> SEQ ID NO 56
<211> LENGTH: 19
<212> TYPE: DNA
<213> ORGANISM: Homo sapiens

<400> SEQUENCE: 56
ctaagtgact accacttat                                               19

<210> SEQ ID NO 57
<211> LENGTH: 19
<212> TYPE: DNA
<213> ORGANISM: Homo sapiens

<400> SEQUENCE: 57
gttcagaagt tgttagtga                                               19

<210> SEQ ID NO 58
<211> LENGTH: 19
<212> TYPE: DNA
<213> ORGANISM: Homo sapiens

<400> SEQUENCE: 58
agttgttagt gatttgcta                                               19

<210> SEQ ID NO 59
<211> LENGTH: 19
<212> TYPE: DNA
<213> ORGANISM: Homo sapiens

<400> SEQUENCE: 59
gacgtattgt gaaatttgt                                               19
```

```
<210> SEQ ID NO 60
<211> LENGTH: 19
<212> TYPE: DNA
<213> ORGANISM: Homo sapiens

<400> SEQUENCE: 60
tcatcaattt cgagcagaa                                               19

<210> SEQ ID NO 61
<211> LENGTH: 19
<212> TYPE: DNA
<213> ORGANISM: Homo sapiens

<400> SEQUENCE: 61
tgagtttgga gataataca                                               19

<210> SEQ ID NO 62
<211> LENGTH: 19
<212> TYPE: DNA
<213> ORGANISM: Homo sapiens

<400> SEQUENCE: 62
tggccgatgt gtctattga                                               19

<210> SEQ ID NO 63
<211> LENGTH: 19
<212> TYPE: DNA
<213> ORGANISM: Homo sapiens

<400> SEQUENCE: 63
cgatgtgtct attgaagat                                               19

<210> SEQ ID NO 64
<211> LENGTH: 19
<212> TYPE: DNA
<213> ORGANISM: Homo sapiens

<400> SEQUENCE: 64
gcattaaagg actgactga                                               19

<210> SEQ ID NO 65
<211> LENGTH: 19
<212> TYPE: DNA
<213> ORGANISM: Homo sapiens

<400> SEQUENCE: 65
tcgtttggct tgtggtgta                                               19

<210> SEQ ID NO 66
<211> LENGTH: 21
<212> TYPE: DNA
<213> ORGANISM: Homo sapiens

<400> SEQUENCE: 66
aatttcgagc agaaggaaag t                                            21

<210> SEQ ID NO 67
<211> LENGTH: 21
<212> TYPE: DNA
<213> ORGANISM: Homo sapiens

<400> SEQUENCE: 67
aagcattaaa ggactgactg a                                            21
```

```
<210> SEQ ID NO 68
<211> LENGTH: 21
<212> TYPE: DNA
<213> ORGANISM: Homo sapiens

<400> SEQUENCE: 68
aatgtgactg ctgacaaaga t                                              21

<210> SEQ ID NO 69
<211> LENGTH: 21
<212> TYPE: DNA
<213> ORGANISM: Homo sapiens

<400> SEQUENCE: 69
aagattctgt gatctcactc t                                              21
```